United States Patent

Shinohata et al.

(10) Patent No.: US 9,233,918 B2
(45) Date of Patent: *Jan. 12, 2016

(54) ISOCYANATE PRODUCTION PROCESS

(75) Inventors: Masaaki Shinohata, Tokyo (JP);
Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 521 days.

This patent is subject to a terminal disclaimer.

(21) Appl. No.: 12/991,625

(22) PCT Filed: May 15, 2008

(86) PCT No.: PCT/JP2008/058952
§ 371 (c)(1),
(2), (4) Date: Nov. 8, 2010

(87) PCT Pub. No.: WO2009/139062
PCT Pub. Date: Nov. 19, 2009

(65) Prior Publication Data
US 2011/0092731 A1    Apr. 21, 2011

(51) Int. Cl.
*C07C 263/04* (2006.01)
*C07C 263/18* (2006.01)
(52) U.S. Cl.
CPC ............ *C07C 263/04* (2013.01); *C07C 263/18* (2013.01); *C07C 2101/14* (2013.01)
(58) Field of Classification Search
CPC combination set(s) only.
See application file for complete search history.

(56) References Cited

U.S. PATENT DOCUMENTS 2,692,275 A   10/1954   Bortnick
3,125,598 A    3/1964   Kuhle et al.
(Continued)

FOREIGN PATENT DOCUMENTS

CA   1166649 A1   5/1984
CN   1432563 A    7/2002
(Continued)

OTHER PUBLICATIONS

Patent Abstracts of Japan, Abstract pf JP 04-026665.*
(Continued)

*Primary Examiner* — Karl J Puttlitz
(74) *Attorney, Agent, or Firm* — Morgan, Lewis & Bockius LLP

(57) ABSTRACT

An object of the present invention is to provide a process that enables isocyanate to be produced stably over a long period of time and at high yield without encountering problems of the prior art during production of isocyanate without using phosgene. The present invention discloses a process for producing an isocyanate by subjecting a carbamic acid ester to a thermal decomposition reaction, including the steps of: recovering a low boiling point component in a form of a gaseous phase component from a thermal decomposition reaction vessel in which the thermal decomposition reaction is carried out; recovering a liquid phase component containing a carbamic acid ester from a bottom of the thermal decomposition reaction vessel; and supplying all or a portion of the liquid phase component to an upper portion of the thermal decomposition reaction vessel.

30 Claims, 11 Drawing Sheets

(56) References Cited

U.S. PATENT DOCUMENTS

| | | | |
|---|---|---|---|
| 3,382,289 A | 5/1968 | Edwards et al. | |
| 3,734,941 A | 5/1973 | Sydor | |
| 3,992,430 A | 11/1976 | Bacskai | |
| 4,081,472 A | 3/1978 | Tsumura et al. | |
| 4,097,676 A | 6/1978 | Romano | |
| 4,123,450 A * | 10/1978 | Weber, Jr. | 560/345 |
| 4,290,970 A | 9/1981 | Merger et al. | |
| 4,354,979 A | 10/1982 | Schwendemann et al. | |
| 4,386,033 A | 5/1983 | Konig et al. | |
| 4,388,238 A | 6/1983 | Heitkamper et al. | |
| 4,388,246 A | 6/1983 | Sundermann et al. | |
| 4,388,426 A | 6/1983 | Schure et al. | |
| 4,430,505 A | 2/1984 | Heitkamper et al. | |
| 4,480,110 A | 10/1984 | Heitkamper et al. | |
| 4,482,499 A | 11/1984 | Merger et al. | |
| 4,497,963 A | 2/1985 | Merger et al. | |
| 4,514,339 A | 4/1985 | Romano et al. | |
| 4,596,678 A | 6/1986 | Merger et al. | |
| 4,596,679 A | 6/1986 | Hellbach et al. | |
| 4,613,466 A | 9/1986 | Merger et al. | |
| 4,659,845 A | 4/1987 | Rivetti et al. | |
| 4,692,550 A | 9/1987 | Engbert et al. | |
| 4,925,971 A | 5/1990 | Aoki et al. | |
| 5,087,739 A | 2/1992 | Bohmholdt et al. | |
| 5,315,034 A | 5/1994 | Mizia et al. | |
| 5,386,053 A * | 1/1995 | Otterbach et al. | 560/344 |
| 5,498,319 A | 3/1996 | Ehlinger | |
| 5,502,244 A | 3/1996 | Okawa et al. | |
| 5,616,784 A | 4/1997 | Schwarz et al. | |
| 5,688,988 A | 11/1997 | Bosetti et al. | |
| 5,698,731 A | 12/1997 | Bosetti et al. | |
| 5,731,458 A * | 3/1998 | Dahmer et al. | 560/345 |
| 5,883,291 A * | 3/1999 | Schleenstein et al. | 560/345 |
| 6,034,265 A | 3/2000 | Bosetti et al. | |
| 6,143,917 A | 11/2000 | Harada et al. | |
| 6,222,065 B1 | 4/2001 | Okawa et al. | |
| 6,992,214 B2 * | 1/2006 | Cesti et al. | 560/345 |
| 7,446,218 B2 | 11/2008 | Miyake et al. | |
| 2003/0055282 A1 | 3/2003 | Bosman et al. | |
| 2003/0125579 A1 | 7/2003 | Yoshida et al. | |
| 2005/0080274 A1* | 4/2005 | Miyake et al. | 549/228 |
| 2007/0055042 A1 | 3/2007 | Miyake et al. | |
| 2008/0275262 A1 | 11/2008 | Miyake et al. | |
| 2010/0029981 A1 | 2/2010 | Shinohata et al. | |
| 2010/0069665 A1 | 3/2010 | Shinohata et al. | |
| 2011/0054211 A1 | 3/2011 | Shinohata et al. | |
| 2011/0092731 A1 | 4/2011 | Shinohata et al. | |
| 2011/0319648 A1 | 12/2011 | Shinohata et al. | |

FOREIGN PATENT DOCUMENTS

| | | |
|---|---|---|
| CN | 1419538 A | 5/2003 |
| CN | 1749241 A | 3/2006 |
| DE | 925 496 | 3/1955 |
| EP | 0 125 726 A1 | 11/1984 |
| EP | 0 320 235 A2 | 6/1989 |
| EP | 0 355 443 A2 | 2/1990 |
| EP | 0 446 514 | 9/1991 |
| EP | 0 957 073 | 11/1999 |
| EP | 1 640 357 | 3/2006 |
| EP | 2088137 A1 | 8/2009 |
| EP | 2088138 A1 | 8/2009 |
| EP | 2147909 A1 | 1/2010 |
| GB | 1217122 | 12/1970 |
| JP | 46-27593 B1 | 8/1971 |
| JP | 52-71443 | 6/1977 |
| JP | 52-136147 | 11/1977 |
| JP | 54-039002 | 3/1979 |
| JP | S57-082361 A | 5/1982 |
| JP | 59-108754 | 6/1984 |
| JP | 60-231640 | 11/1985 |
| JP | 61-183257 | 8/1986 |
| JP | 1-230550 | 9/1989 |
| JP | 4-026665 | 1/1992 |
| JP | 04-026665 * | 1/1992 |
| JP | 6-25136 | 2/1994 |
| JP | 06-056984 | 3/1994 |
| JP | 6-192204 | 7/1994 |
| JP | H07-025830 A | 1/1995 |
| JP | H07-138208 A | 5/1995 |
| JP | 07-258194 | 10/1995 |
| JP | H09-025262 A | 1/1997 |
| JP | 09-087239 | 3/1997 |
| JP | H09-100265 A | 4/1997 |
| JP | H09-249632 A | 9/1997 |
| JP | 10-316645 | 12/1998 |
| JP | 11-5774 | 1/1999 |
| JP | H11-001462 A | 1/1999 |
| JP | 2000-344730 | 12/2000 |
| JP | 2001-048855 A | 2/2001 |
| JP | 3-238201 B | 10/2001 |
| JP | 2001-323106 | 11/2001 |
| JP | 2002-500654 | 1/2002 |
| JP | 33-82289 B | 12/2002 |
| JP | 2003-055332 | 2/2003 |
| JP | 2003-201275 A | 7/2003 |
| JP | 2003-525267 | 8/2003 |
| JP | 2004-244349 | 9/2004 |
| JP | 2004-262834 | 9/2004 |
| JP | 2004-262835 | 9/2004 |
| JP | 2006-069941 | 3/2006 |
| WO | 95/23484 | 8/1995 |
| WO | 98/54128 | 12/1998 |
| WO | 03/055840 | 7/2003 |
| WO | 2004/014840 | 2/2004 |
| WO | 2005/000783 | 1/2005 |
| WO | 2005/111049 | 11/2005 |
| WO | 2009/066616 A1 | 5/2009 |

OTHER PUBLICATIONS

Machine Translation of JP 09-249632.*
Office Action issued in Chinese Patent Application No. 200880129186.3 dated Dec. 13, 2012.
Office Action issued in Japanese Patent Application No. 2010-511823 dated Feb. 6, 2013.
Office Action issued in Canadian Patent Application No. 2,721,357 dated Dec. 31, 2012.
Hofmann, Berchte der Deutechen Chemischen Gesellschaft, vol. 3, p. 653, 1870.
Dyer et al., "Thermal Degradation of Alkyl N-Phenylcarbamates" Journal of the American Chemical Society, vol. 81, p. 2138-2143, 1959.
Kosa et al., "New combined phenol-hindered amine stabilizers for polymers based on diphenylmethane-4, 4'-diisocyanate and dicyclohexylmethane-4,4'-diisocyanate", Polymer Degradation and Stability, 86(3), p. 391-400, 2004.
Habicher et al., "Synthesis and Antioxidative Properties of Novel Multifunctional Stabilizers" Journal of Vinyl & Additives Technology, vol. 7, No. 1, pp. 4-18, 2001.
Kovacic et al., "Reactions of t-Butylperoxy Isopropyl Carbonate with Aromatic Compounds under Friedel-Crafts Conditions", Journal of Organic Chemistry, vol. 31, No. 8, pp. 2459-2467, 1966.
Petersen, Polyurethans. V. Low-molecular conversion products of diisocyanates, Ann., 562, pp. 205-229, 1949.
Yamazaki et al., "The Reaction of Diphenyl Carbonate with Amines and Its Application to Polymer Synthesis", Journal of Polymer Science, Polymer Chemistry Edition, vol. 17, p. 835-841, 1979.
Tarbell et al., "Acidic and Basic Catalysis in Urethan Formation", Journal of the American Chemical Society, vol. 64 (9), p. 2229-2230, 1942.
Edited by Kagaku Dai Jiten Henshu linkai, Kagaku Dai Jiten 7, vol. 32, Kyoritsu Shuppan Co., Ltd., pp. 725-728, 1989.
Leuckart, "Ueber einige Synthesen mittelst Phenylcyanat", Journal fur Practische Chemie, vol. 41, pp. 301-329 1890, XP002542888 p. 319-320.
Ohme, "Synthesen mit Brenzacatechincarbonat", Journal fur Practische Chemie, vol. 313, pp. 626-635, 1971, XP002542889 p. 630, last paragraph p. 631, Tabelle 4.

(56) References Cited

OTHER PUBLICATIONS

STN Accession No. 127:247849 CASREACT structure diagram for Schleenstein et al. U.S. Pat. No. 5,883,291.
Xylenol Printout http://en.wikipedia.org/wiki/Xylenol.
Office Action issued in corresponding Japanese Patent Application No. 2010-511823 dated Jun. 26, 2013.
Porta et al., "Reactions of Diethyl Carbonate with Amines Catalyzed by Metal Centres," Gazzetta Chimica Italiana, 115: 275-277 (1985).
Office Action issued in related U.S. Appl. No. 12/991,586 dated Sep. 17, 2013.
Office Action issued in related Japanese Patent Application No. 2013-048033 dated Feb. 12, 2014.
Office Action issued in Taiwan Patent Application No. 097118261 dated Jul. 15, 2011.
European Search Report issued in corresponding European application No. 08752810.5 dated Sep. 15, 2015.

* cited by examiner

ISOCYANATE PRODUCTION PROCESS

RELATED APPLICATIONS

The present application is a U.S. National Phase Application of International Application No. PCT/JP2008/058952 (filed May 15, 2008) which is hereby incorporated by reference in their entirety.

TECHNICAL FIELD

The present invention relates to an isocyanate production process.

BACKGROUND ART

Isocyanates are widely used as raw materials of such products as polyurethane foam, paints, adhesives and the like. The main industrial production process of isocyanates involves reacting amine compounds with phosgene (phosgene method), and nearly the entire amount of isocyanates produced throughout the world are produced according to the phosgene method. However, the phosgene method has numerous problems.

Firstly, this method requires the use of a large amount of phosgene as the raw material. Phosgene is extremely toxic and requires special handling precautions to prevent exposure of handlers thereof, and also requires special apparatuses to detoxify waste.

Secondly, since highly corrosive hydrogen chloride is produced in large amounts as a by-product of the phosgene method, in addition to requiring a process for detoxifying the hydrogen chloride, in many cases hydrolytic chlorine is contained in the isocyanates produced. Consequently, in the case of using isocyanates produced by the phosgene method, the isocyanates may have a detrimental effect on the weather resistance and heat resistance of polyurethane products.

On the basis of this background, a process for producing isocyanate compounds has been sought that does not use phosgene. One example of a method for producing isocyanate compounds without using phosgene that has been proposed involves thermal decomposition of carbamic acid esters. Isocyanates and hydroxy compounds have long been known to be obtained by thermal decomposition of carbamic acid esters (see, for example, Non-Patent document 1). The basic reaction is illustrated by the following formula:

$$R(NHCOOR')_a \rightarrow R(NCO)_a + aR'OH \quad (1)$$

(wherein R represents an organic residue having a valence of a, R' represents a monovalent organic residue, and a represents an integer of 1 or more).

On the other hand, thermal decomposition of carbamic acid esters is susceptible to the simultaneous occurrence of various irreversible side reactions such as thermal denaturation reactions undesirable for carbamic acid esters or condensation of isocyanates formed by the thermal decomposition. Examples of these side reactions may include a reaction in which urea bonds are formed as represented by the following formula (2), a reaction in which carbodiimides are formed as represented by the following formula (3), and a reaction in which isocyanurates are formed as represented by the following formula (4) (see Non-Patent documents 1 and 2).

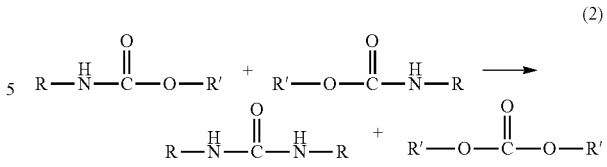

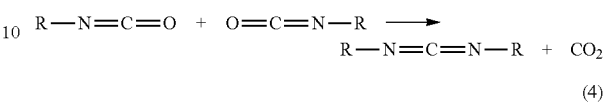

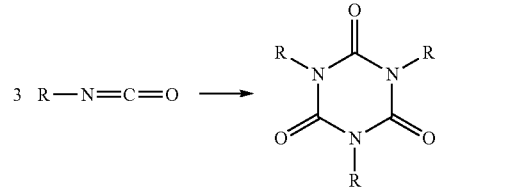

Note that in the above formulas, R and R' represent groups such as aliphatic alkyl groups or aromatic alkyl groups.

In addition to these side reactions leading to a decrease in yield and selectivity of the target isocyanate, in the production of polyisocyanates in particular, these reactions may make long-term operation difficult as a result of, for example, causing the precipitation of polymeric solids that clog the reaction vessel.

Various processes have been proposed thus far for the production of isocyanates without using phosgene.

According to the description of Patent document 1, aliphatic diurethane and/or alicyclic diurethane and/or aliphatic polyurethane and/or alicyclic polyurethane are obtained by reacting aliphatic primary diamine and/or alicyclic primary diamine and/or aliphatic primary polyamine and/or alicyclic primary polyamine in the presence of an O-alkyl carbamate and alcohol, in the presence or absence of a catalyst at a temperature of from 160 to 300° C. such that the ratio of amine $NH_2$ groups to carbamate to alcohol is 1:0.8 to 10:0.25 to 50, and by removing the ammonia formed as necessary. The resulting diurethane and/or polyurethane can be converted to the corresponding diisocyanate and/or highly functional polyisocyanate as necessary. Details of the reaction conditions of the thermal decomposition are not described in the applicable patent document.

According to Patent document 2, aromatic diisocyanates and/or polyisocyanates are produced by going through the following two steps. More specifically, in the first step, an aromatic primary amine and/or aromatic primary polyamine are reacted with an O-alkyl carbamate in the presence or absence of a catalyst and in the presence or absence of urea and alcohol to form an aryl diurethane and/or aryl polyurethane followed by removal of the ammonia formed as necessary. In the second step, an aromatic isocyanate and/or aromatic polyisocyanate are obtained by thermal decomposition of the aryl diurethane and/or aryl polyurethane.

Other publications contain descriptions relating to the partial substitution of urea and/or diamine a carbonyl-containing compound such as N-substituted carbamate and/or dialkyl carbonate, or by mono-substituted urea, di-substituted urea, mono-substituted polyurea or di-substituted polyurea (see Patent document 3, Patent document 4, Patent document 5, Patent document 6 and Patent document 7). Patent document 8 describes a process for producing aliphatic O-aryl urethane by reacting (cyclic) aliphatic polyamines with urea and aromatic hydroxy compounds.

Several processes are known for forming the corresponding isocyanate and alcohol by thermal decomposition of the (cyclic) aliphatic, and particularly the aromatic monourethanes and diurethanes, examples of which may include a process carried out at a high temperature in a gaseous phase, and a process carried out under comparatively low temperature conditions in a liquid phase. In these processes, however, since there are cases in which, for example, the reaction mixture forms precipitates, polymeric substances and closed compounds in the reaction vessel and recovery apparatus due to the occurrence of side reactions as previously described, or these substances form substances that adhere to the walls of the reaction vessel, economic efficiency is poor in the case of producing isocyanates over a long period of time.

Thus, chemical methods, such as the use of a special catalyst (see Patent document 9 and Patent document 10) or a catalyst combined with an insert solvent (see Patent document 11) are disclosed for improving yield during thermal decomposition of urethane.

For example, Patent document 12 describes a process for producing hexamethylene diisocyanate involving thermal decomposition of hexamethylene diethyl urethane in the presence of dibenzyl toluene used as a solvent and in the presence of a catalyst mixture containing methyl toluene sulfonate and diphenyl tin dichloride. However, since there is no detailed description of production of the starting components, isolation or purification and arbitrary recovery of the solvent and catalyst mixture, the economic effects of this process were unable to be assessed.

According to the process described in Patent document 13, urethane can be easily decomposed to isocyanate and alcohol in a carbon-containing fluidized bed without using a catalyst. In addition, according to the description of Patent document 14, hexamethylene dialkyl urethane can be decomposed in a gaseous phase at a temperature exceeding 300° C. in the presence or absence of a gas-permeable packaging material composed of, for example, carbon, copper, bronze, steel, zinc, aluminum, titanium, chromium, cobalt or quartz, resulting in the formation of hexamethylene diisocyanate.

According to the description of Patent document 14, the process is carried out in the presence of a hydrogen halide and/or hydrogen halide donor. However, this process is unable to achieve a yield of hexamethylene diisocyanate of 90% or more. This is because the decomposition product partially rebonds resulting in the formation of urethane bonds. Thus, purification of the hexamethylene diisocyanate by distillation is still required, and there are numerous cases in which yield loss increases.

Moreover, Patent document 15 discloses that monocarbamates can be advantageously decomposed at high yield without using a solvent under reduced pressure and/or in the presence or absence of a stabilizer and at a comparatively low temperature. The decomposition products (monoisocyanates and alcohol) are removed by distillation from a boiling reaction mixture and captured separately by fractional condensation. A method for partially removing the reaction mixture is generically described in order to remove by-products formed during thermal decomposition. Thus, although it is possible to remove by-products from the bottom of the reaction vessel, the problem of the case of substances adhering to the walls of the reaction vessel as previously described remains, and problems regarding long-term operation are unresolved. In addition, there is no description regarding the industrial use of the removed residual substances (containing large amounts of useful components).

According to the description of Patent document 16, thermal decomposition of aliphatic, alicyclic or aromatic polycarbamates is carried out at from 150 to 350° C. and from 0.001 to 20 bar, in the presence of an inert solvent, and in the presence or absence of a catalyst and assistant in the form of hydrogen chloride, organic acid chloride, alkylation agent or organic tin compound. By-products formed can be removed continuously from the reaction vessel together with the reaction solution, for example, and corresponding amounts of fresh solvent or recovered solvent are added simultaneously. Examples of disadvantages of this process may include a decrease in the space time yield of polyisocyanate due to the use of a circulating solvent, and a large energy requirement, including recovery of the solvent. Moreover, since the assistant used is volatile under the reaction conditions, contamination of the decomposition products can occur. In addition, since there is a large amount of residual substances formed relative to the polyisocyanate formed, there is some doubt regarding economic efficiency and reliability as an industrial process.

Patent document 17 describes a process for continuous thermal decomposition of a carbamate supplied along the inner walls of a tubular reaction vessel in the form of a liquid in the presence of a high boiling point solvent, an example of which may include an alicyclic diurethane in the form of 5-(ethoxycarbonylamino)-1-(ethoxycarbonylaminomethyl)-1,3,3-trimethylcyclohexane. This process has the shortcomings of low yield and low selectivity during production of (cyclic) aliphatic diisocyanates. In addition, there is no description of a continuous method accompanying recovery of rebonded or partially decomposed carbamates, nor is there any mention of post-treatment of solvent containing by-products and catalyst.

According to the description of Patent document 18, a circulating process is disclosed for producing (cyclic) aliphatic diisocyanates by conversion of the corresponding diamine to diurethane followed by thermal decomposition of the urethane. This process minimizes decreases in yield by recirculating the product of the urethane decomposition step following reaction with alcohol to an urethanation step. By-products that are unable to be recirculated are removed by separating the by-products by distilling a mixture of the urethanation products, and in this case, residues of no value are formed in the form of bottom products, and all components having a comparatively low boiling point, including diurethane, are removed from the top of the column. However, this process has the shortcoming of using a large amount of energy. This is because, in addition to requiring all diurethanes to be evaporated in the presence of a catalyst, the diurethanes must be evaporated at a temperature level within a range of the decomposition temperature of urethane. Isocyanate groups formed in useful products react with residual urethane, frequently resulting in the formation of comparatively high molecular weight by-products that decrease yield.

According to the description of Patent document 19, a process is disclosed whereby worthless by-products are partially removed outside the system prior to carrying out thermal decomposition of polyurethane. The shortcoming of this process is a decrease in the yield of isocyanate since polyurethane ends up being contained in the by-products partially removed outside the system. In addition, although components that do not undergo thermal decomposition present in a reaction mixture obtained in the thermal decomposition step of polyurethane and containing unreacted polyurethane, high boiling point oligomers, and other worthless by-products that are able to be reused are separated and continuously removed from the thermal decomposition apparatus and recirculated to the urethanation step following reaction with alcohol either directly or as necessary in an attempt to increase the yield of isocyanates, recirculated high boiling point oligomers present in the system during the urethanation step may precipitate in the urethanation reaction vessel and gradually accumulate on the walls of the reaction vessel, thereby impairing operation over a long period of time.

In addition, according to the description of Patent document 20, isocyanates are produced by continuous thermal cleavage decomposition of carbamic acid ester using a process in which a reaction medium containing carbamic acid ester is heated so that a biphasic mixture is formed having a gas volume of greater than 50%, the gaseous phase is continuously discharged from the reaction vessel, and the liquid phase is continuously discharged from the reaction vessel. In this process as well, although components that do not undergo thermal decomposition present in a reaction mixture containing unreacted polyurethane, high boiling point oligomers, and other worthless by-products that are able to be reused are separated and continuously removed from the thermal decomposition apparatus and recirculated to the urethanation step following reaction with alcohol either directly or as necessary in an attempt to increase the yield of isocyanates, similar to the process described above, recirculated high boiling point oligomers present in the system during the urethanation step may precipitate in the urethanation reaction vessel and gradually accumulate on the walls of the reaction vessel, thereby impairing operation over a long period of time.

Patent document 21 discloses a process for carrying out thermal decomposition by evaporating methyl urethane, obtained by reacting dimethyl carbonate and amine in the presence of a basic catalyst followed by introducing into a thermal decomposition reaction vessel. Although unevaporated components are removed from the bottom of the evaporator during evaporation of methyl urethane, since methyl urethane ends up being contained in the removed components, this process has the shortcoming of causing a decrease in the yield of isocyanate. In addition, thermal denaturation of methyl urethane also tends to occur easily since methyl urethane vapor is transferred at a high temperature.

Patent document 1: U.S. Pat. No. 4,497,963
Patent document 2: U.S. Pat. No. 4,290,970
Patent document 3: U.S. Pat. No. 4,388,238
Patent document 4: U.S. Pat. No. 4,430,505
Patent document 5: U.S. Pat. No. 4,480,110
Patent document 6: U.S. Pat. No. 4,596,678
Patent document 7: U.S. Pat. No. 4,596,679
Patent document 8: European Patent Publication No. 0320235
Patent document 9: U.S. Pat. No. 2,692,275
Patent document 10: U.S. Pat. No. 3,734,941
Patent document 11: U.S. Pat. No. 4,081,472
Patent document 12: U.S. Pat. No. 4,388,426
Patent document 13: U.S. Pat. No. 4,482,499
Patent document 14: U.S. Pat. No. 4,613,466
Patent document 15: U.S. Pat. No. 4,386,033
Patent document 16: U.S. Pat. No. 4,388,246
Patent document 17: U.S. Pat. No. 4,692,550
Patent document 18: European Patent No. 0355443
Patent document 19: U.S. Pat. No. 5,386,053
Patent document 20: Japanese Patent No. 3238201
Patent document 21: U.S. Pat. No. 5,315,034
Non-Patent document 1: Berchte der Deutechen Chemischen Gesellschaft, Vol. 3, p. 653, 1870
Non-Patent documents 2: Journal of American Chemical Society, Vol. 81, p. 2138, 1959

DISCLOSURE OF THE INVENTION

Problems to be Solved by the Invention

As has been described above, various studies have been conducted on processes for producing isocyanates without using toxic phosgene. However, due to the problem of long-term, continuous operation being difficult due to the formation of high boiling point by-products and the adhesion of these high boiling point by-products to the reaction vessel, hardly any of these processes have been carried out industrially.

An object of the present invention is to provide a process that allows stable production of isocyanates over a long period without using phosgene that is free of the various problems found in the prior art.

Means for Solving the Problems

As a result of conducting extensive studies to solve the above problems, the inventors of the present invention unexpectedly found that, in a process for producing isocyanates by subjecting carbamic acid ester to a thermal decomposition reaction, operation can be carried out continuously for a long period of time without causing clogging of the reaction vessel due to adhesion of by-products thereto by supplying a liquid phase component recovered from a bottom of the thermal decomposition reaction vessel to an upper portion of the thermal decomposition reaction vessel, thereby leading to completion of the present invention.

Namely, the present invention provides the following:

[1] a process for producing an isocyanate by subjecting a carbamic acid ester to a thermal decomposition reaction, comprising the steps of:
  recovering a low boiling point component in a form of a gaseous phase component from a thermal decomposition reaction vessel in which the thermal decomposition reaction is carried out;
  recovering a liquid phase component containing the carbamic acid ester from a bottom of the thermal decomposition reaction vessel; and
  supplying all or a portion of the liquid phase component to an upper portion of the thermal decomposition reaction vessel.

[2] the process according to item [1], wherein the carbamic acid ester is supplied to the thermal decomposition reaction vessel within a temperature range of from 50 to 180° C.

[3] the process according to item [1] or [2], wherein the carbamic acid ester is supplied to the thermal decomposition reaction vessel in a form of a liquid.

[4] the process according to any one of items [1] to [3], wherein the carbamic acid ester is a carbamic acid ester produced by reacting a carbonic acid ester with an amine compound.

[5] the process according to item [4], wherein the reaction vessel for producing the carbamic acid ester and the thermal decomposition reaction vessel may be the same or different, and the reaction vessel for producing the carbamic acid ester and the thermal decomposition reaction vessel are at least one reaction vessel selected from the group consisting of a column-type reaction vessel and a tank-type reaction vessel.

[6] the process according to any one of items [1] to [5], wherein the thermal decomposition reaction vessel is composed of at least one reaction vessel selected from the group consisting of an evaporator, a continuous multistage distillation column, a packed column, a thin film evaporator and a falling film evaporator.

[7] the process according to any one of items [1] to [6], wherein the thermal decomposition reaction is carried out in a liquid phase.

[8] the process according to any one items [4] to [7], wherein a mixture, in which all or a portion of a hydroxy compound and/or all or a portion of the carbonic acid ester has been separated from a mixture containing the carbamic acid ester produced by reacting a carbonic acid ester and an amine compound, is supplied to a thermal decomposition reaction apparatus.

[9] the process according to item [8], wherein the separation is carried out by distillative separation, and the distillative separation is carried out at 180° C. or lower.

[10] the process according to any one of items [1] to [9], wherein all or a portion of the liquid phase component recovered from the bottom of the thermal decomposition reaction vessel is supplied to the upper portion of the thermal decomposition reaction vessel within a temperature range of from 50 to 180° C.

[11] the process according to any one of item [4] to [10], wherein the carbonic acid ester is used at a stoichiometric ratio of 1 time or more based on amino groups constituting the amine compound.

[12] the process according to any one of items [1] to [11], further comprising cleaning a high boiling point by-product adhered to the thermal decomposition reaction vessel, with an acid.

[13] the process according to item [12], wherein the acid is an aromatic hydroxy compound.

[14] the process according to any one of items [4] to [13], wherein the carbonic acid ester is a compound represented by the following formula (1):

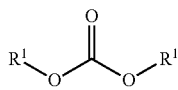

(1)

(wherein $R^1$ represents an aliphatic group having 1 to 12 carbon atoms or an aromatic group having 6 to 12 carbon atoms).

[15] the process according to item [14], wherein the carbonic acid ester contains a metal atom at from 0.001 ppm to 10%.

[16] the process according to item [15], wherein the metal atom is one type or a plurality of types of metal atoms selected from the group consisting of iron, nickel, cobalt, zinc, tin, copper and titanium atoms.

[17] the process according to any one of items [14] to [16], wherein $R^1$ in the carbonic acid ester represents an aliphatic group having 5 to 7 carbon atoms or an aromatic group having 6 to 7 carbon atoms.

[18] the process according to any one of items [4] to [17], wherein the amine compound is a compound represented by the following formula (2):

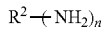

(2)

(wherein $R^2$ represents a group selected from the group consisting of an aliphatic group having 1 to 20 carbon atoms and an aromatic group having 6 to 20 carbon atoms, the above group containing an atom selected from carbon and oxygen atoms, and having a valence equal to n, and n represents an integer of from 2 to 10).

[19] the process according to item [18], wherein the amine compound is a diamine compound represented by formula (2) in which n is 2.

[20] the process according to any one of items [1] to [19], wherein a low boiling point component is supplied to a distillation column in a form of a gaseous component from the low boiling point component formed by the thermal decomposition reaction and recovered in a form of a gaseous phase component, and a hydroxy compound originating from the carbamic acid ester and an isocyanate originating from the carbamic acid ester are separated in the distillation column.

[21] the process according to any one of items [1] to [20], wherein a hydroxy compound originating from the carbamic acid ester and an isocyanate originating from the carbamic acid ester are recovered separately from a low boiling point component formed by the thermal decomposition reaction and recovered in a form of a gaseous component by a thin film evaporator.

[22] the process according to any one of items [1] to [21], wherein the isocyanate is recovered from the liquid phase component by distillative separation.

[23] the process according to any one of items [14] to [22], wherein $R^1$ in the carbonic acid ester in formula (1) represents an aliphatic group having 1 to 12 carbon atoms, and the carbonic acid ester is produced according to a process which comprises the following steps (1) and (2):

step (1): obtaining a reaction mixture containing a dialkyl carbonate by reacting an organic tin compound having a tin-oxygen-carbon bond and carbon dioxide; and step (2): obtaining a dialkyl carbonate and a residue liquid by separating the reaction mixture.

[24] the process according to any one of items [14] to [22], wherein $R^1$ in the carbonic acid ester in formula (1) represents an aromatic group having 6 to 12 carbon atoms, and the carbonic acid ester is produced according to a process which comprises the following step (3) in addition to the steps (1) and (2):

step (3): obtaining a diaryl carbonate by reacting the dialkyl carbonate separated in step (2) and an aromatic hydroxy compound A followed by recovering a by-product alcohol.

[25] the process according to item [23] or [24], wherein the carbonic acid ester is a carbonic acid ester produced by a process which comprises the following steps (4) and (5) in addition to the steps (1) and (2) or the steps (1) to (3):

step (4): forming an organic tin compound having a tin-oxygen-carbon bond and water by reacting the residue liquid obtained in step (2) with an alcohol followed by removing the water from a reaction system; and step (5): reusing the organic tin compound having the tin-oxygen-carbon bond obtained in step (4) as the organic tin compound having the tin-oxygen-carbon bond of step (1).

[26] the process according to item [25], wherein the alcohol recovered in step (3) is reused as the alcohol of step (4).

[27] the process according to item [25], wherein in the case the hydroxy compound is an alcohol, it is used as the alcohol of step (4), while in the case the hydroxy compound is an aromatic hydroxy compound, it is used as the aromatic hydroxy compound A of step (3).

[28] the process according to any one of items [8] to [27], wherein the separated carbonic acid ester is reused as a carbonic acid ester.

[29] the process according to any one of items [1] to [28], wherein the thermal decomposition reaction of the carbamic acid ester is carried out in the absence of a solvent.

[30] the process according to any one of items [4] to [29], wherein supply of the amine compound to the reaction vessel in which the carbonic acid ester and the amine compound are reacted is carried out in a liquid state.

[31] the process according to any one of items [4] to [30], wherein supply of the amine compound to the reaction vessel in which the carbonic acid ester and the amine compound are reacted is carried out in a form of a mixture with alcohol, water or carbonic acid ester.

Advantageous Effects of the Invention

According to the present invention, isocyanates can be produced without using phosgene, and continuous operation is possible over a long period of time.

Figure 7:
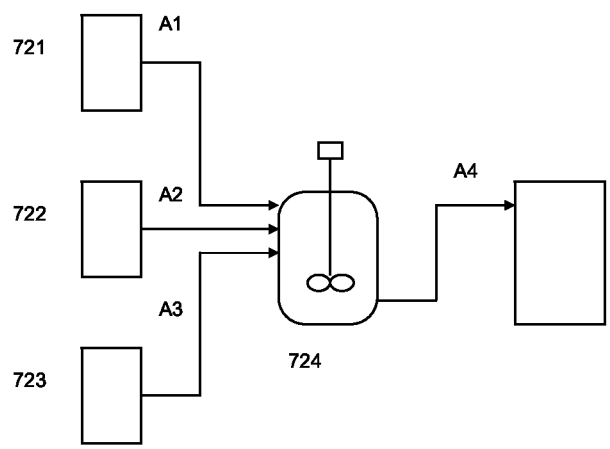
FIG. 7 is a conceptual drawing showing a carbamic acid ester production apparatus according to an embodiment of the present invention.
Figure 8:
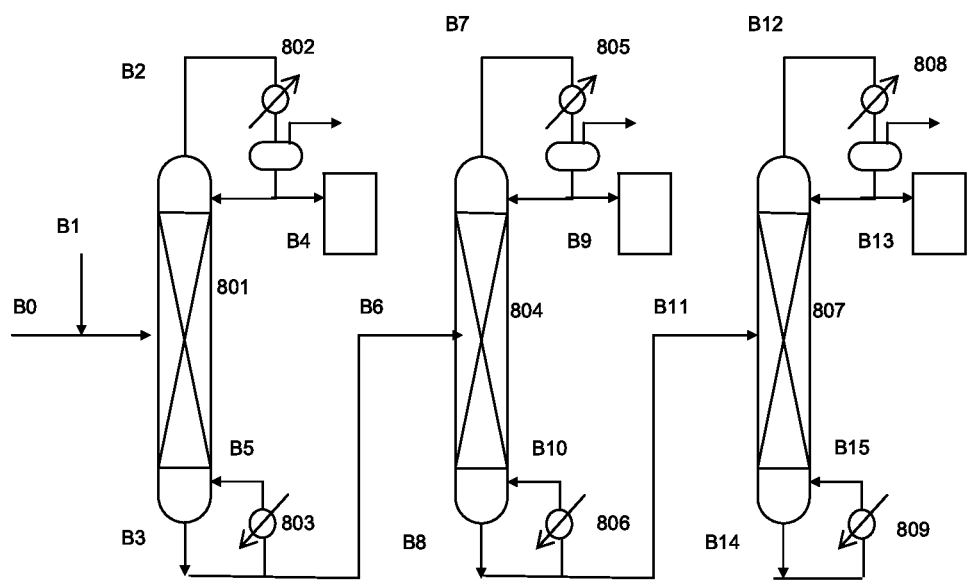
FIG. 8 is a conceptual drawing showing an isocyanate production apparatus according to an embodiment of the present invention.
Figure 10:
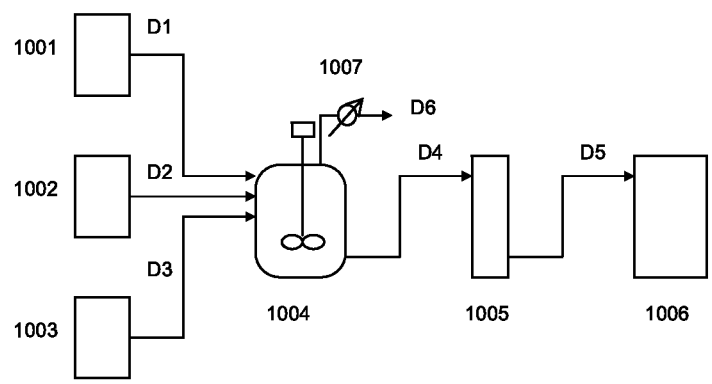
FIG. 10 is a conceptual drawing showing a carbamic acid ester production apparatus according to an embodiment of the present invention.
Figure 11:
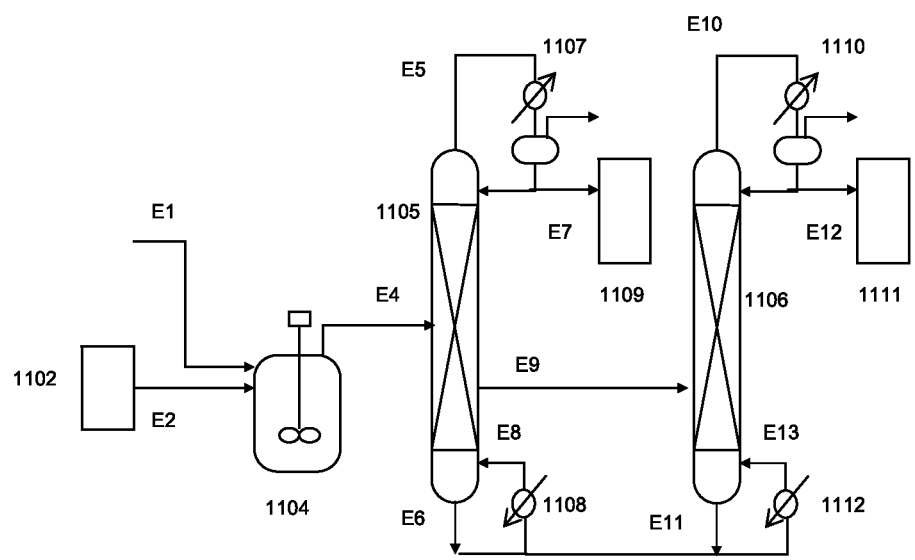
FIG. 11 is a conceptual drawing showing an isocyanate production apparatus according to an embodiment of the present invention.

DESCRIPTION OF REFERENCE NUMERALS (In FIG. 1)
101, 107: distillation column
102: column-type reaction vessel
103, 106: thin film evaporator
104: autoclave
105: decarbonization tank
111, 112, 117: reboiler
121, 123, 126, 127: condenser
1, 2, 3, 4, 5, 6, 7, 8, 9, 10, 11, 12, 13, 14, 15, 16, 17: line (In FIG. 2)
201, 202, 203, 206: storage tank
204: baffled reaction vessel
205: column
21, 22, 23, 24, 25: line
(In FIG. 3)
302: continuous multistage distillation column
305, 306: storage tank
301: preheater
303: condenser
304: reboiler
31, 32, 33, 34, 35: line
(In FIG. 4)
402: continuous multistage distillation column
405, 406: storage tank
401: preheater
403: condenser
404: reboiler
41, 42, 43, 44, 45: line
(In FIG. 5)
501: thin film evaporator
502, 505: continuous multistage distillation column
508, 509, 510: storage tank
503, 506: condenser
504, 507: reboiler
50, 51, 52, 53, 54, 55, 56, 57, 58, 59, 60, 61, 62, 63, 64: line
(In FIG. 6)
701: thin film evaporator
702, 705, 708: continuous multistage distillation column
703, 706, 709: condenser
704, 707, 710: reboiler
711: storage tank
70, 71, 72, 73, 74, 75, 76, 77, 78, 79, 80, 81, 82, 83, 84, 85, 86, 87, 88, 89: line
(In FIG. 7)
721, 722, 723, 725: storage tank
724: baffled reaction vessel
A1, A2, A3, A4: line
(In FIG. 8)
801, 804, 807: continuous multistage distillation column
802, 605, 808: condenser
803, 806, 809: reboiler
B1, B2, B3, B4, B5, B6, B7, B8, B9, B10, B11, B12, B13, B14, B15: line
(In FIG. 9)
901, 902, 903, 906: storage tank
904: baffled reaction vessel
905: column
C1, C2, C3, C4, C5, C6: line
(In FIG. 10)
1001, 1002, 1003, 1006: storage tank
1004: baffled reaction vessel
1005: column
1007: condenser
D1, D2, D3, D4, D5, D6: line
(In FIG. 11)
1102, 1409, 1411: storage tank
1104: baffled reaction vessel
1105, 1106: continuous multistage distillation column
1107, 1110: condenser
1108, 1112: reboiler
E1, E2, E3, E4, E5, E6, E7, E8, E9, E10, E11, E12, E13: line

BEST MODE FOR CARRYING OUT THE INVENTION

The following provides a detailed explanation of the best mode for carrying out the present invention (hereinafter referred to as "present embodiment"). It should be noted that the present invention is not limited to the following present embodiment, but rather can be modified in various ways within the scope of the gist thereof.

The isocyanate production process according to the present embodiment is a process for producing isocyanate by subjecting a carbamic acid ester, produced by reacting a carbonic acid ester and an amine compound, to a thermal decomposition reaction in the absence of a solvent, which comprises the steps of: recovering a low boiling point component from the thermal decomposition reaction vessel in which the thermal decomposition reaction is carried out in the form of a gaseous phase component; recovering a liquid phase component containing carbamic acid ester from a bottom of the thermal decomposition reaction vessel; and supplying all or a portion of the liquid phase component to an upper portion of the thermal decomposition reaction vessel.

<Carbamic Acid Ester>

Although there are no particular limitations on the carbamic acid ester used in the isocyanate production process according to the present embodiment, a carbamic acid ester represented by the following formula (7) is used preferably:

(7)

(wherein $R^3$ represents a group selected from the group consisting of an aliphatic group having 1 to 20 carbon atoms and an aromatic group having 6 to 20 carbon atoms, the above group containing an atom selected from carbon and oxygen atoms, and having a valence equal to n, $R^4$ represents an aliphatic group having 1 to 20 carbon atoms or aromatic group having 6 to 20 carbon atoms, the aliphatic and aromatic group containing an atom selected from carbon and oxygen atoms, and n represents an integer of from 1 to 10).

In formula (7) above, the carbamic acid ester is preferably a polycarbamic acid ester in which n is a number selected from integers of 2 or more, and more preferably a polycarbamic acid ester in which n is 2.

Examples of $R^3$ in formula (7) may include linear hydrocarbons such as methylene, dimethylene, trimethylene, tetramethylene, pentamethylene, hexamethylene or octamethylene; unsubstituted alicyclic hydrocarbons such as cyclopentane, cyclohexane, cycloheptane, cyclooctane or bis(cyclohexyl)alkane; alkyl-substituted cyclohexanes such as methylcyclopentane, ethylcyclopentane, methylcyclohexane (including isomers), ethylcyclohexane (including isomers), propylcyclohexane (including isomers), butylcyclohexane (including isomers), pentylcyclohexane (including isomers) or hexylcyclohexane (including isomers); dialkyl-substituted cyclohexanes such as dimethylcyclohexane (including isomers), diethylcyclohexane (including isomers) or dibutylcyclohexane (including isomers); trialkyl-substituted cyclohexanes such as 1,5,5-trimethylcyclohexane, 1,5,5-triethylcyclohexane, 1,5,5-tripropylcyclohexane (including isomers) or 1,5,5-tributylcyclohexane (including isomers); monoalkyl-substituted benzenes such as toluene, ethylbenzene or propylbenzene; dialkyl-substituted benzenes such as xylene, diethylbenzene or dipropylbenzene; and aromatic hydrocarbons such as diphenyalkane or benzene. In particular, hexamethylene, phenylene, diphenylmethane, toluene, cyclohexane, xylenyl, methylcyclohexane, isophorone and dicyclohexylmethane groups are used preferably.

Examples of $R^4$ in formula (7) above may include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers) or an eicosyl group (including isomers); cycloalkyl groups such as a cyclopentyl group, a cyclohexyl group, a cycloheptyl group, a cyclooctyl group, a cyclononyl group or a cyclodecyl group; alkoxyalkyl groups such as a methoxymethyl group, a methoxyethyl group (including isomers), a methoxypropyl group ((including isomers), a methoxybutyl group (including isomers), a methoxypentyl group (including isomers), a methoxyhexyl group (including isomers), a methoxyheptyl group (including isomers), a methoxyoctyl group (including isomers), a methoxynonyl group (including isomers), a methoxydecyl group (including isomers), a methoxyundecyl group (including isomers), a methoxydodecyl group (including isomers), a methoxytridecyl group (including isomers), a methoxytetradecyl group (including isomers), a methoxypentadecyl group (including isomers), a methoxyhexadecyl group (including isomers), a methoxyheptadecyl group (including isomers), a methoxyoctadecyl group (including isomers), a methoxynonadecyl group (including isomers), an ethoxymethyl group, an ethoxyethyl group (including isomers), an ethoxypropyl group (including isomers), an ethoxybutyl group (including isomers), an ethoxypentyl group (including isomers), an ethoxyhexyl group (including isomers), an ethoxyheptyl group (including isomers), an ethoxyoctyl group (including isomers), an ethoxynonyl group (including isomers), an ethoxydecyl group (including isomers), an ethoxyundecyl group (including isomers), an ethoxydodecyl group (including isomers), an ethoxytridecyl group (including isomers), an ethoxytetradecyl group (including isomers), an ethoxypentadecyl group (including isomers), an ethoxyhexadecyl group (including isomers), an ethoxyheptadecyl group (including isomers), an ethoxyoctadecyl group (including isomers), a propyloxymethyl group (including isomers), a propyloxyethyl group (including isomers), a propyloxypropyl group (including isomers), a propyloxybutyl group (including isomers), a propyloxypentyl group (including isomers), a propyloxyhexyl group (including isomers), a propyloxyheptyl group (including isomers), a propyloxyoctyl group (including isomers), a propyloxynonyl group (including isomers), a propyloxydecyl group (including isomers), a propyloxyundecyl group (including isomers), a propyloxydodecyl group (including isomers), a propyloxytridecyl group (including isomers), a propyloxytetradecyl group (including isomers), a propyloxypentadecyl group (including isomers), a propyloxyhexadecyl group (including isomers), a propyloxyheptadecyl group (including isomers), a butyloxymethyl group (including isomers), a butyloxyethyl group (including isomers), a butyloxypropyl group (including isomers), a butyloxybutyl group (including isomers), a butyloxypentyl group (including isomers), a butyloxyhexyl group (including isomers), a butyloxyheptyl group (including isomers), a butyloxyoctyl group (including isomers), a butyloxynonyl group (including isomers), a butyloxydecyl group (including isomers), a butyloxyundecyl group (including isomers), a butyloxydodecyl group (including isomers), a butyloxytridecyl group (including isomers), a butyloxytetradecyl group (including isomers), a butyloxypentadecyl group (including isomers), a butyloxyhexadecyl group (including isomers), a pentyloxymethyl group (including isomers), a pentyloxyethyl group (including isomers), a pentyloxypropyl group (including isomers), a pentyloxybutyl group (including isomers), a pentyloxypentyl group (including isomers), a pentyloxyhexyl group (including isomers), a pentyloxyheptyl group (including isomers), a pentyloxyoctyl group (including isomers), a pentyloxynonyl group (including isomers), a pentyloxydecyl group (including isomers), a pentyloxyundecyl group (including isomers), a pentyloxydodecyl group (including isomers), a pentyloxytridecyl group (including isomers), a pentyloxytetradecyl group (including isomers), a pentyloxypentadecyl group (including isomers), a hexyloxymethyl group (including isomers), a hexyloxyethyl group (including isomers), a hexyloxypropyl group (including isomers), a hexyloxybutyl group (including isomers), a hexyloxypentyl group (including isomers), a hexyloxyhexyl group (including isomers), a hexyloxyheptyl group (including isomers), a hexyloxyoctyl group (including isomers), a hexyloxynonyl group (including isomers), a hexyloxydecyl group (including isomers), a hexyloxyundecyl group (including isomers), a hexyloxydodecyl group (including isomers), a hexyloxytridecyl group (including isomers), a hexyloxytetradecyl group (including isomers), a heptyloxymethyl group (including isomers), a heptyloxyethyl group (including isomers), a heptyloxypropyl group (including isomers), a heptyloxybutyl group (including isomers), a heptyloxypentyl group (including isomers), a heptyloxyhexyl group (including isomers), a heptyloxyheptyl group (including isomers), a heptyloxyoctyl group (including isomers), a heptyloxynonyl group (including isomers), a heptyloxydecyl group (including isomers), a heptyloxyundecyl group (including isomers), a heptyloxydodecyl group (including isomers), a heptyloxytridecyl group (including isomers), an octyloxymethyl group, an octyloxyethyl group (including isomers), an octyloxypropyl group (including isomers), an octyloxybutyl group (including isomers), an octyloxypentyl group (including isomers), an octyloxyhexyl group (including isomers), an octyloxyheptyl group (including isomers), an octyloxyoctyl group (including isomers), an octyloxynonyl group (including isomers), an octyloxydecyl group (including isomers), an octyloxyundecyl group (including isomers), an octyloxydodecyl group (including isomers), a nonyloxymethyl group (including isomers), a nonyloxyethyl group (including isomers), a nonyloxypropyl group (including isomers), a nonyloxybutyl group (including isomers), a nonyloxypentyl group (including isomers), a nonyloxyhexyl group (including isomers), a nonyloxyheptyl group (including isomers), a nonyloxyoctyl group (including isomers), a nonyloxynonyl group (including isomers), a nonyloxydecyl group (including isomers), a nonyloxyundecyl group (including isomers), a decyloxymethyl group (including isomers), a decyloxyethyl group (including isomers), a decyloxypropyl group (including isomers), a decyloxybutyl group (including isomers), a decyloxypentyl group (including isomers), a decyloxyhexyl group (including isomers), a decyloxyheptyl group (including isomers), a decyloxyoctyl group (including isomers), a decyloxynonyl group (including isomers), a decyloxydecyl group (including isomers), an undecyloxymethyl group, an undecyloxyethyl group (including isomers), an undecyloxypropyl group (including isomers), an undecyloxybutyl group (including isomers), an undecyloxypentyl group (including isomers), an undecyloxyhexyl group (including isomers), an undecyloxyheptyl group (including isomers), an undecyloxyoctyl group (including isomers), an undecyloxynonyl group (including isomers), a dodecyloxymethyl group (including isomers), a dodecyloxyethyl group (including isomers), a dodecyloxypropyl group (including isomers), a dodecyloxybutyl group (including isomers), a dodecyloxypentyl group (including isomers), a dodecyloxyhexyl group (including isomers), a dodecyloxyheptyl group (including isomers), a dodecyldecyloxyoctyl group (including isomers), a tridecyloxymethyl group (including isomers), a tridecyloxyethyl group (including isomers), a tridecyloxypropyl group (including isomers), a tridecyloxybutyl group (including isomers), a tridecyloxypentyl group (including isomers), a tridecyloxyhexyl group (including isomers), a tridecyloxyheptyl group (including isomers), a tetradecyloxymethyl group (including isomers), a tetradecyloxyethyl group (including isomers), a tetradecyloxypropyl group (including isomers), a tetradecyloxybutyl group (including isomers), a tetradecyloxypentyl group (including isomers), a tetradecyloxyhexyl group (including isomers), a pentadecyloxymethyl group, a pentadecyloxyethyl group (including isomers), a pentadecyloxypropyl group (including isomers), a pentadecyloxybutyl group (including isomers), a pentadecyloxypentyl group (including isomers), a hexadecyloxymethyl group (including isomers), a hexadecyloxyethyl group (including isomers), a hexadecyloxypropyl group (including isomers), a hexadecyloxybutyl group (including isomers), a heptadecyloxymethyl group, a heptadecyloxyethyl group (including isomers), a heptadecyloxypropyl group (including isomers), an octadecyloxymethyl group (including isomers) or an octadecyloxyethyl group (including isomers); and, aromatic groups such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a dodecylphenyl group (including isomers), a phenylphenyl group (including isomers), a phenoxyphenyl group (including isomers), a cumylphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a diphenylphenyl group (including isomers), a diphenyoxyphenyl group (including isomers), a methylethylphenyl group (including isomers), a methylpropylphenyl group (including isomers), a methylbutylphenyl group (including isomers), a methylpentylphenyl group (including isomers), a methylhexylphenyl group (including isomers), a methylheptylphenyl group (including isomers), a methyloctylphenyl group (including isomers), a methylnonylphenyl group (including isomers), a methyldecylphenyl group (including isomers), a methyldodectylphenyl group (including isomers), a methylphenylphenyl group (including isomers), a methylphenoxyphenyl group (including isomers), a methylcumylphenyl group (including isomers), an ethylpropylphenyl group (including isomers), an ethylbutylphenyl group (including isomers), an ethylpentylphenyl group (including isomers), an ethylhexylphenyl group (including isomers), an ethylheptylphenyl group (including isomers), an ethyloctylphenyl group (including isomers), an ethylnonylphenyl group (including isomers), an ethyldecylphenyl group (including isomers), an ethyldodecylphenyl group (including isomers), an ethylphenylphenyl group (including isomers), an ethylphenoxyphenyl group (including isomers), an ethylcumylphenyl group (including isomers), a propylbutylphenyl group (including isomers), a propylpentylphenyl group (including isomers), a propylhexylphenyl group (including isomers), a propylheptylphenyl group (including isomers), a propyloctylphenyl group (including isomers), a propylnonylphenyl group (including isomers), a propyldecylphenyl group (including isomers), a propylphenylpheny group (including isomers), a propylphenoxyphenyl group (including isomers), a butylpentylphenyl group (including isomers), a butylhexylphenyl group (including isomers), a butylheptylphenyl group (including isomers), a butyloctylphenyl group (including isomers), a butylnonylphenyl group (including isomers), a butyldecylphenyl group (including isomers), a butylphenylphenyl group (including isomers), a butylphenoxyphenyl group (including isomers), a pentylhexylphenyl group (including isomers), a pentylheptylphenyl group (including isomers), a pentyloctylphenyl group (including isomers), a pentylnonylphenyl group (including isomers), a pentylphenylphenyl group (including isomers), a pentylphenoxyphenyl group (including isomers), a hexylheptylphenyl group (including isomers), a hexyloctylphenyl group (including isomers), a hexylphenylphenyl group (including isomers), a hexylphenoxyphenyl group (including isomers), a trimethylphenyl group (including isomers), a triethylphenyl group (including isomers), a tripropylphenyl group (including isomers), a tributylphenyl group (including isomers), a dimethylethylphenyl group (including isomers), a dimethylpropylphenyl group (including isomers), a dimethylbutylphenyl group (including isomers), a dimethylpentylphenyl group (including isomers), a dimethylhexylphenyl group (including isomers), a dimethylheptylphenyl group (including isomers), a dimethyloctylphenyl group (including isomers), a dimethylnonylphenyl group (including isomers), a dimethyldecylphenyl group (including isomers), a dimethyldodecylphenyl group (including isomers), a dimethylphenylphenyl group (including isomers), a dimethylphenoxyphenyl group (including isomers), a dimethylcumylphenyl group (including isomers), a diethylmethylphenyl group (including isomers), a diethylpropylphenyl group (including isomers), a diethylbutylphenyl group (including isomers), a diethylpentylphenyl group (including isomers), a diethylhexylphenyl group (including isomers), a diethylheptylphenyl group (including isomers), a diethyloctylphenyl group (including isomers), a diethylnonylphenyl group (including isomers), a diethyldecylphenyl group (including isomers), a diethylphenylphenyl group (including isomers), a diethylphenoxyphenyl group (including isomers), a diethylcumylphenyl group (including isomers), a dipropylmethylphenyl group (including isomers), a dipropylethylphenyl group (including isomers), a dipropylbutylphenyl group (including isomers), a dipropylpentylphenyl group (including isomers), a dipropylhexylphenyl group (including isomers), a dipropylheptylphenyl group (including isomers), a dipropylphenylphenyl group (including isomers), a dipropylphenoxyphenyl group (including isomers), a dibutylmethylphenyl group (including isomers), a dibutylethylphenyl group (including isomers), a dibutylpropylphenyl group (including isomers), a dibutylpentylphenyl group (including isomers), a dibutylhexylphenyl group (including isomers), a dibutylphenylphenyl group (including isomers), a dibutylphenoxyphenyl group (including isomers), a dipentylmethylphenyl group (including isomers), a dipentylethylphenyl group (including isomers), a dipentylpropylphenyl group (including isomers), a dipentylbutylphenyl group (including isomers), a dihexylmethylphenyl group (including isomers), a dihexylethylphenyl group (including isomers), a methylethylpropylphenyl group (including isomers), a methylethylbutylphenyl group (including isomers), a methylethylpentylphenyl group (including isomers), a methylethylhexylphenyl group (including isomers), a methylethylheptylphenyl group (including isomers), a methylethyloctylphenyl group (including isomers), a methylethylnonylphenyl group (including isomers), a methylethyldecylphenyl group (including isomers), a methylethylphenoxyphenyl group (including isomers), a methylethylcumylphenyl group (including isomers), a methylpropylbutylphenyl group (including isomers), a methylpropylpentylphenyl group (including isomers), a methylpropylhexylphenyl group (including isomers), a methylpropylheptylphenyl group (including isomers), a methylpropyloctylphenyl group (including isomers), a methylpropylnonylphenyl group (including isomers), a methylpropyldecylphenyl group (including isomers), a methylpropylphenoxyphenyl group (including isomers), a methylpropylcumylphenyl group (including isomers), a methylbutylpentylphenyl group (including isomers), a methylbutylhexylphenyl group (including isomers), a methylbutylheptylphenyl group (including isomers), a methylbutyloctylphenyl group (including isomers), a methylbutylphenoxyphenyl group (including isomers), a methylbutylcumylphenyl group (including isomers), a methylpentylhexylphenyl group (including isomers), a methylpentylheptylphenyl group (including isomers), a methylpentyloctylphenyl group (including isomers), a methylpentylphenoxyphenyl group (including isomers), a methylhexylheptylphenyl group (including isomers), an ethylpropylbutylphenyl group (including isomers), an ethylpropylpentylphenyl group (including isomers), an ethylpropylhexylphenyl group (including isomers), an ethylpropylheptylphenyl group (including isomers), an ethylpropyloctylphenyl group (including isomers), an an ethylpropylnonylphenyl group (including isomers), an ethylpropylphenoxyphenyl group (including isomers), an ethylpropylcumylphenyl group (including isomers), an ethylbutylpentylphenyl group (including isomers), an ethylbutylhexylphenyl group (including isomers), an ethylbutylheptylphenyl group (including isomers), an ethylbutyloctylphenyl group (including isomers), an ethylbutylphenoxyphenyl group (including isomers), an ethylpentylhexylphenyl group (including isomers), an ethylpentylheptylphenyl group (including isomers), an ethylpentylphenoxyphenyl group (including isomers), a propylbutylphenyl group (including isomers), a propylbutylpentylphenyl group (including isomers), a propylbutylhexylphenyl group (including isomers), a propylbutylheptylphenyl group (including isomers), a propylbutylphenoxyphenyl group (including isomers), a propylpentylhexylphenyl group (including isomers) or a propylpentylphenoxyphenyl group.

Among these groups, alkyl groups in which the number of carbon atoms constituting the group is a number selected from the group consisting of integers of from 5 to 12 or aryl groups in which the number of carbon atoms constituting the group is a number selected from the group consisting of integers of from 6 to 12 are preferable, and alkyl groups in the form of pentyl groups (including isomers), hexyl groups (including isomers), heptyl groups (including isomers) or octyl groups (including isomers), in which the number of carbon atoms constituting the group is a number selected from the group consisting of integers of from 5 to 7, and aryl groups in the form of phenyl groups or methylphenyl groups (including isomers), in which the number of carbon atoms constituting the group is a number selected from the group consisting of integers of from 5 to 7 are used more preferably. In the case of alkyl groups or aryl groups in which the number of carbon atoms is 4 or less, since the boiling point of the carbamic acid ester is not sufficiently high, under the conditions of thermal decomposition of carbamic acid esters to be described later, there are cases in which the carbamic acid ester is distilled off in the gaseous phase, thereby making it difficult to separate from isocyanates and the like. In addition, in the case of alkyl groups or aryl groups in which the number of carbon atoms is 8 or more, since the difference between the boiling point of the hydroxy compound formed in the thermal decomposition reaction and the boiling point of the isocyanate becomes small, difficulties may be encountered during separation.

Examples of such alkyl polycarbamates may include alkyl carbamates such as N,N'-hexanediyl-bis-carbamic acid dipentyl ester (including isomers), N,N'-hexanediyl-bis-carbamic acid dihexyl ester (including isomers), N,N'-hexanediyl-bis-carbamic acid diheptyl ester (including isomers), dipentyl-4,4'-methylene-dicyclohexylcarbamate (including isomers), dihexyl-4,4'-methylene-dicyclohexylcarbamate (including isomers), diheptyl-4,4'-methylene-dicyclohexylcarbamate (including isomers), 3-(pentyloxycarbonylaminomethyl)-3,5,5-trimethylcyclohexyl carbamic acid pentyl ester (including isomers), 3-(hexyloxycarbonylaminomethyl)-3,5,5-trimethylcyclohexyl carbamic acid hexyl ester (including isomers), 3-(heptyloxycarbonylaminomethyl)-3,5,5-trimethylcyclohexyl carbamic acid heptyl ester (including isomers), toluene dicarbamic acid dipentyl ester (including isomers), toluene dicarbamic acid dihexyl ester (including isomers), toluene dicarbamic acid diheptyl ester (including isomers), N,N'-(4,4'-methanediyl-diphenyl)-bis-carbamic acid dipentyl ester, N,N'-(4,4'-methanediyl-diphenyl)-biscarbamic acid dihexyl ester or N,N'-(4,4'-methanediyl-diphenyl)-biscarbamic acid diheptyl ester; and, aryl carbamates such as N,N'-hexanediyl-bis-carbamic acid diphenyl ester, N,N'-hexanediyl-bis-carbamic acid di(methylphenyl) ester (including isomers), diphenyl-4,4'-methylene-dicyclohexylcarbamate, di(methylphenyl)-4,4'-methylene-dicyclohexylcarbamate (including isomers), 3-(phenoxycarbonylaminomethyl)-3,5,5-trimethylcyclohexyl carbamic acid phenyl ester (including isomers), 3-((methylphenoxy)carbonylaminomethyl)-3,5,5-trimethylcyclohexyl carbamic acid (methylphenyl) ester (including isomers), toluene dicarbamic acid diphenyl ester (including isomers), toluene dicarbamic acid di(methylphenyl) ester (including isomers), N,N'-(4,4'-methanediyl-diphenyl)-biscarbamic acid diphenyl ester or N,N'-(4,4'-methanediyl-diphenyl)-biscarbamic acid di(methylphenyl) ester.

These carbamic acid esters can be produced using a known process, and may be produced by, for example, reacting the amine compounds, carbon monoxide, oxygen and aliphatic alcohols or aromatic hydroxy compounds. In addition, carbamic acid esters may also be produced by reacting the amine compounds, urea and the aliphatic alcohols or aromatic hydroxy compounds, or by reacting carbonic acid esters and the amine compounds. Carbamic acid esters are preferably produced by reacting the carbonic acid esters and the amine compounds.

Carbonic acid esters represented by the following formula (8) can be used for the carbonic acid ester.

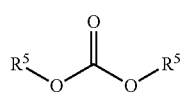

(8)

(wherein $R^5$ represents a linear or branched aliphatic group having 1 to 20 carbon atoms or an aromatic group having 6 to 20 carbon atoms).

Examples of $R^5$ may include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers) or an eicosyl group (including isomers); cycloalkyl groups such as a cyclopentyl group, a cyclohexyl group, a cycloheptyl group, a cyclooctyl group, a cyclononyl group or a cyclodecyl group; alkoxyalkyl groups such as a methoxymethyl group, a methoxyethyl group (including isomers), a methoxypropyl group ((including isomers), a methoxybutyl group (including isomers), a methoxypentyl group (including isomers), a methoxyhexyl group (including isomers), a methoxyheptyl group (including isomers), a methoxyoctyl group (including isomers), a methoxynonyl group (including isomers), a methoxydecyl group (including isomers), a methoxyundecyl group (including isomers), a methoxydodecyl group (including isomers), a methoxytridecyl group (including isomers), a methoxytetradecyl group (including isomers), a methoxypentadecyl group (including isomers), a methoxyhexadecyl group (including isomers), a methoxyheptadecyl group (including isomers), a methoxyoctadecyl group (including isomers), a methoxynonadecyl group (including isomers), an ethoxymethyl group, an ethoxyethyl group (including isomers), an ethoxypropyl group (including isomers), an ethoxybutyl group (including isomers), an ethoxypentyl group (including isomers), an ethoxyhexyl group (including isomers), an ethoxyheptyl group (including isomers), an ethoxyoctyl group (including isomers), an ethoxynonyl group (including isomers), an ethoxydecyl group (including isomers), an ethoxyundecyl group (including isomers), an ethoxydodecyl group (including isomers), an ethoxytridecyl group (including isomers), an ethoxytetradecyl group (including isomers), an ethoxypentadecyl group (including isomers), an ethoxyhexadecyl group (including isomers), an ethoxyheptadecyl group (including isomers), an ethoxyoctadecyl group (including isomers), a propyloxymethyl group (including isomers), a propyloxyethyl group (including isomers), a propyloxypropyl group (including isomers), a propyloxybutyl group (including isomers), a propyloxypentyl group (including isomers), a propyloxyhexyl group (including isomers), a propyloxyheptyl group (including isomers), a propyloxyoctyl group (including isomers), a propyloxynonyl group (including isomers), a propyloxydecyl group (including isomers), a propyloxyundecyl group (including isomers), a propyloxydodecyl group (including isomers), a propyloxytridecyl group (including isomers), a propylexytetradecyl group (including isomers), a propyloxypentadecyl group (including isomers), a propyloxyhexadecyl group (including isomers), a propylheptadecyl group (including isomers), a butyloxymethyl group (including isomers), a butyloxyethyl group (including isomers), a butyloxypropyl group (including isomers), a butyloxybutyl group (including isomers), a butyloxypentyl group (including isomers), a butyloxyhexyl group (including isomers), a butyloxyheptyl group (including isomers), a butyloxyoctyl group (including isomers), a butyloxynonyl group (including isomers), a butyloxydecyl group (including isomers), a butyloxyundecyl group (including isomers), a butyloxydodecyl (including isomers), a butyloxytridecyl group (including isomers), a butyloxytetradecyl group (including isomers), a butyloxypentadecyl group (including isomers), a butyloxyheadecyl group (including isomers), a pentyloxymethyl group (including isomers), a pentyloxyethyl group (including isomers), a pentyloxypropyl group (including isomers), a pentyloxybutyl group (including isomers), a pentyloxypentyl group (including isomers), a pentyloxyhexyl group (including isomers), a pentyloxyheptyl group (including isomers), a pentyloxyoctyl group (including isomers), a pentyloxynonyl group (including isomers), a pentyloxydecyl group (including isomers), a pentyloxyundecyl group (including isomers), a pentyloxydodecyl group (including isomers), a pentyloxytridecyl group (including isomers), a pentyloxytetradecyl group (including isomers), a pentyloxypentadecyl group (including isomers), a hexyloxymethyl group (including isomers), a hexyloxyethyl group (including isomers), a hexyloxypropyl group (including isomers), a hexyloxybutyl group (including isomers), a hexyloxypentyl group (including isomers), hexyloxyhexyl group (including isomers), a hexyloxyheptyl group (including isomers), a hexyloxyoctyl group (including isomers), a hexyloxynonyl group (including isomers), a hexyloxydecyl group (including isomers), a hexyloxyundecyl group (including isomers), a hexyloxydodecyl group (including isomers), a hexyloxytridecyl group (including isomers), a hexyloxytetradecyl group (including isomers), a heptyloxymethyl group (including isomers), a heptyloxyethyl group (including isomers), a heptyloxypropyl group (including isomers), a heptyloxybutyl group (including isomers), a heptyloxypentyl group (including isomers), a heptyloxyhexyl group (including isomers), a heptyloxyheptyl group (including isomers), a heptyloxyoctyl group (including isomers), a heptyloxynonyl group (including isomers), a heptyloxydecyl group (including isomers), a heptyloxyundecyl group (including isomers), a heptyloxydodecyl group (including isomers), a heptyloxytridecyl group (including isomers), an octyloxymethyl group, an octyloxyethyl group (including isomers), an octyloxypropyl group (including isomers), an octyloxybutyl group (including isomers), an octyloxypentyl group (including isomers), an octyloxyhexyl group (including isomers), an octyloxyheptyl group (including isomers), an octyloxyoctyl group (including isomers), an octyloxynonyl group (including isomers), an octyloxydecyl group (including isomers), an octyloxyundecyl group (including isomers), an octyloxydodecyl group (including isomers), a nonyloxymethyl group (including isomers), a nonyloxyethyl group (including isomers), a nonyloxypropyl group (including isomers), a nonyloxybutyl group (including isomers), a nonyloxypentyl group (including isomers), a nonyloxyhexyl group (including isomers), a nonyloxyheptyl group (including isomers), a nonyloxyoctyl group (including isomers), a nonyloxynonyl group (including isomers), a nonyloxydecyl group (including isomers), a nonyloxyundecyl group (including isomers), a decyloxymethyl group (including isomers), a decyloxyethyl group (including isomers), a decyloxypropyl group (including isomers), a decyloxybutyl group (including isomers), a decyloxypentyl group (including isomers), a decyloxyhexyl group (including isomers), a decyloxyheptyl group (including isomers), a decyloxyoctyl group (including isomers), a decyloxynonyl group (including isomers), a decyloxydecyl group (including isomers), an undecyloxymethyl group, an undecyloxyethyl group (including isomers), an undecyloxypropyl group (including isomers), an undecyloxybutyl group (including isomers), an undecyloxypentyl group (including isomers), an undecyloxyhexyl group (including isomers), an undecyloxyheptyl group (including isomers), an undecyloxyoctyl group (including isomers), an undecyloxynonyl group (including isomers), a dodecyloxymethyl group (including isomers), a dodecyloxyethyl group (including isomers), a dodecyloxypropyl group ((including isomers), a dodecyloxybutyl group (including isomers), a dodecyloxypentyl group (including isomers), a dodecyloxyhexyl group (including isomers), a dodecyloxyheptyl group (including isomers), a dodecyloxyoctyl group (including isomers), a tridecyloxymethyl group (including isomers), a tridecyloxyethyl group (including isomers), a tridecyloxypropyl group (including isomers), a tridecyloxybutyl group (including isomers), a tridecyloxypentyl group (including isomers), a tridecyloxyhexyl group (including isomers), a tridecyloxyheptyl group (including isomers), a tetradecyloxymethyl group (including isomers), a tetradecyloxyethyl group (including isomers), a tetradecyloxypropyl group (including isomers), a tetradecyloxybutyl group (including isomers), a tetradecyloxypentyl group (including isomers), a tetradecyloxyhexyl group (including isomers), a pentadecyloxymethyl group (including isomers), a pentadecyloxyethyl group (including isomers), a pentadecyloxypropyl group (including isomers), a pentadecyloxybutyl group (including isomers), a pentadecyloxypentyl group (including isomers), a hexadecyloxymethyl group (including isomers), a hexadecyloxyethyl group (including isomers), a hexadecyloxypropyl group (including isomers), a hexadecyloxybutyl group (including isomers), a heptadecyloxymethyl group (including isomers), a heptadecyloxyethyl group (including isomers), a heptadecyloxypropyl group (including isomers), an octadecyloxymethyl group (including isomers) or an octadecyloxyethyl group (including isomers); and, aromatic groups such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a dodecylphenyl group (including isomers), a phenylphenyl group (including isomers), a phenoxyphenyl group (including isomers), a cumylphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a diphenylphenyl group (including isomers), a diphenoxyphenyl group (including isomers), a methylethylphenyl group (including isomers), a methylpropylphenyl group (including isomers), a methylbutylphenyl group (including isomers), a methylpentylphenyl group (including isomers), a methylhexylphenyl group (including isomers), a methylheptylphenyl group (including isomers), a methyloctylphenyl group (including isomers), a methylnonylphenyl group (including isomers), a methyldecylphenyl group (including isomers), a methyldodecylphenyl group (including isomers), a methylphenylphenyl group (including isomers), a methylphenoxyphenyl group (including isomers), a methylcumylphenyl group (including isomers), an ethylpropylphenyl group (including isomers), an ethylbutylphenyl group (including isomers), an ethylpentylphenyl group (including isomers), an ethylhexylphenyl group (including isomers), an ethylheptylphenyl group (including isomers), an ethyloctylphenyl group (including isomers), an ethylnonylphenyl group (including isomers), an ethyldecylphenyl group (including isomers), an ethyldodecylphenyl group (including isomers), an ethylphenylphenyl group (including isomers), an ethylphenoxyphenyl group (including isomers), an ethylcumylphenyl group (including isomers), a propylbutylphenyl group (including isomers), a propylpentylphenyl group (including isomers), a propylhexylphenyl group (including isomers), a propylheptylphenyl group (including isomers), a propyloctylphenyl group (including isomers), a propylnonylphenyl group (including isomers), a propyldecylphenyl group (including isomers), a propylphenylphenyl group (including isomers), a propylphenoxyphenyl group (including isomers), a butylpentylphenyl group (including isomers), a butylhexylphenyl group (including isomers), a butylheptylphenyl group (including isomers), a butyloctylphenyl group (including isomers), a butylnonylphenyl group (including isomers), a butyldecylphenyl group (including isomers), a butylphenylphenyl group (including isomers), a butylphenoxyphenyl group (including isomers), a pentylhexylphenyl group (including isomers), a pentylheptylphenyl group (including isomers), a pentyloctylphenyl group (including isomers), a pentylnonylphenyl group (including isomers), a pentylphenylphenyl group (including isomers), a pentylphenoxyphenyl group (including isomers), a hexylheptylphenyl group (including isomers), a hexyloctylphenyl group (including isomers), a hexylphenylphenyl group (including isomers), a hexylphenoxyphenyl group (including isomers), a trimethylphenyl group (including isomers), a triethylphenyl group (including isomers), a tripropylphenyl group (including isomers), a tributylphenyl group (including isomers), a dimethylethylphenyl group (including isomers), a dimethylpropylphenyl group (including isomers), a dimethylbutylphenyl group (including isomers), a dimethylpentylphenyl group (including isomers), a dimethylhexylphenyl group (including isomers), a dimethylheptylphenyl group (including isomers), a dimethyloctylphenyl group (including isomers), a dimethylnonylphenyl group (including isomers), a dimethyldecylphenyl group (including isomers), a dimethyldodecylphenyl group (including isomers), a dimethylphenylphenyl group (including isomers), a dimethylphenoxyphenyl group (including isomers), a dimethylcumylphenyl group (including isomers), a diethylmethylphenyl group (including isomers), a diethylpropylphenyl group (including isomers), a diethylbutylphenyl group (including isomers), a diethylpentylphenyl group (including isomers), a diethylhexylphenyl group (including isomers), a diethylheptylphenyl group (including isomers), a diethyloctylphenyl group (including isomers), a diethylnonylphenyl group (including isomers), a diethyldecylphenyl group (including isomers), a diethylphenylphenyl group (including isomers), a diethylphenoxyphenyl group (including isomers), a diethylcumylphenyl group (including isomers), a dipropylmethylphenyl group (including isomers), a dipropylethylphenyl group (including isomers), a dipropylbutylphenyl group (including isomers), a dipropylpentylphenyl group (including isomers), a dipropylhexylphenyl group (including isomers), a dipropylheptylphenyl group (including isomers), a dipropylphenylphenyl group (including isomers), a dipropylphenoxyphenyl group (including isomers), a dibutylmethylphenyl group (including isomers), a dibutylethylphenyl group (including isomers), a dibutylpropylphenyl group (including isomers), a dibutylpentylphenyl group (including isomers), a dibutylhexylphenyl group (including isomers), a dibutylphenylphenyl group (including isomers), a dibutylphenoxyphenyl group (including isomers), a dipentylmethylphenyl group (including isomers), a dipentylethylphenyl group (including isomers), a dipentylpropylphenyl group (including isomers), a dipentylbutylphenyl group (including isomers), a dihexylmethylphenyl group (including isomers), a dihexylethylphenyl group (including isomers), a methylethylpropylphenyl group (including isomers), a methylethylbutylphenyl group (including isomers), a methylethylpentylphenyl group (including isomers), a methylethylhexylphenyl group (including isomers), a methylethylheptylphenyl group (including isomers), a methylethyloctylphenyl group (including isomers), a methylethylnonylphenyl group (including isomers), a methylethyldecylphenyl group (including isomers), a methylethylphenoxyphenyl group (including isomers), a methylethylcumylphenyl group (including isomers), a methylpropylbutylphenyl group (including isomers), a methylpropylpentylphenyl group (including isomers), a methylpropylhexylphenyl group (including isomers), a methylpropylheptylphenyl group (including isomers), a methylpropyloctylphenyl group (including isomers), a methylpropylnonylphenyl group (including isomers), a methylpropyldecylphenyl group (including isomers), a methylpropylphenoxyphenyl group (including isomers), a methylpropylcumylphenyl group (including isomers), a methylbutylpentylphenyl group (including isomers), a methylbutylhexylphenyl group (including isomers), a methylbutylheptylphenyl group (including isomers), a methylbutyloctylphenyl group (including isomers), a methylbutylphenoxyphenyl group (including isomers), a methylbutylcumylphenyl group (including isomers), a methylpentylhexylphenyl group (including isomers), a methylpentylheptylphenyl group (including isomers), a methylpentyloctylphenyl group (including isomers), a methylpentylphenoxyphenyl group (including isomers), a methylhexylheptylphenyl group (including isomers), an ethylpropylbutylphenyl group (including isomers), an ethylpropylpentylphenyl group (including isomers), an ethylpropylhexylphenyl group (including isomers), an ethylpropylheptylphenyl group (including isomers), an ethylpropyloctylphenyl group (including isomers), an ethylpropylnonylphenyl group (including isomers), an ethylpropylphenoxyphenyl group (including isomers), an ethylpropylcumylphenyl group (including isomers), an ethylbutylpentylphenyl group (including isomers), an ethylbutylhexylphenyl group (including isomers), an ethylbutylheptylphenyl group (including isomers), an ethylbutyloctylphenyl group (including isomers), an ethylbutylphenoxyphenyl group (including isomers), an ethylpentylhexylphenyl group (including isomers), an ethylpentylheptylphenyl group (including isomers), an ethylpentylphenoxyphenyl group (including isomers), a propylbutylpentylphenyl group (including isomers), a propylbutylpentylphenyl group (including isomers), a propylbutylhexylphenyl group (including isomers), a propylbutylheptylphenyl group (including isomers), a propylbutylphenoxyphenyl group (including isomers), a propylpentylhexylphenyl group (including isomers) or a propylpentylphenoxyphenyl group. Among these groups, alkyl groups in which the number of carbon atoms constituting the group is a number selected from the group of integers of from 1 to 20, such as a methyl group, an ethyl group, a propyl group (including isomers), a butyl group (including isomers), a pentyl group (including isomers), a hexyl group (including isomers), a heptyl group (including isomers) or an octyl group (including isomers), are preferable. Among these groups, alkyl groups having 1 to 12 carbon atoms or aromatic groups having 6 to 12 carbon atoms are preferable, while alkyl groups having 5 to 7 carbon atoms or aromatic groups having 5 to 7 carbon atoms are more preferable. Examples of such carbonic acid esters may include dipentyl carbonate (including isomers), dihexyl carbonate (including isomers), diheptyl carbonate (including isomers), diphenyl carbonate and di(methylphenyl)carbonate.

These carbonic acid esters contain metal atoms preferably within a range of from 0.001 ppm to 10%, more preferably within a range of from 0.001 ppm to 5%, and even more preferably within a range of from 0.002 ppm to 3%. In addition, the metal atoms may be present in the form of metal ions or in the form of individual metal atoms. The metal atoms are preferably metal atoms capable of having a valence of from 2 to 4, and one type or a plurality of types of metals selected from the group consisting of iron, cobalt, nickel, zinc, tin, copper and titanium are preferable. The inventors of the present invention unexpectedly found that when the carbonic acid esters containing metal atoms at a concentration within the above range are used, an effect is demonstrated that inhibits a denaturation reaction of the carbamic acid esters formed in the reaction between the carbonic acid esters and the amine compounds. Although the mechanism by which this effect is demonstrated is not clear, the inventors of the present invention presumed that these metal atoms coordinate to urethane bonds (—NHCOO—) of carbamic acid esters formed in the reaction, thereby stabilizing the urethane bonds and inhibiting side reactions as indicated in formula (2) above and formula (9) below, for example:

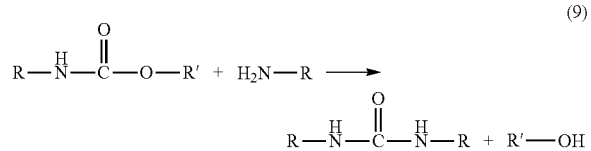

(9)

(wherein each of R and R' independently represents an alkyl group or aromatic group).

In addition, although the effect of inhibiting denaturation of carbamic acid esters by metal atoms is also observed in the transport of a reaction liquid containing carbamic acid esters to be described later, the mechanism of this effect is also presumed to be the same as that described above.

Although similar effects are expected to be obtained even if a mixture is produced by mixing carbonic acid esters and the amine compounds and the previously indicated examples of metal atoms are added to the mixture within the above range, as a result of extensive studies conducted by the inventors of the present invention, it was determined that it is difficult to obtain the above effects simply by adding metal atoms to the mixture of the carbonic acid esters and the amine compounds. Although the reason for obtaining such a result is not clear, the inventors of the present invention presumed that, in contrast to the carbonic acid esters coordinating to the metal atoms contained in the carbonic acid ester, since the interaction between the metal atoms and the amine compounds is greater than the interaction between the metal atoms and the carbonic acid esters, the metal atoms added to the mixture of the carbonic acid esters and the amine compounds strongly coordinate to the amine compounds, thereby making it difficult to coordinate to the urethane bonds of the formed carbamic acid esters.

Although the carbonic acid esters in the present embodiment are preferably produced by the process described below, in the case the previously indicated examples of metal atoms are contained in the carbonic acid esters produced according to this process within the preferable range described above, that carbonic acid ester can be used as is. In the case the amount of the metal atoms contained in the carbonic acid esters is less than the previously described range, other metal atoms can be added in the form of an organic salt such as acetates or naphthenates, chloride or acetyl acetone complex. In addition, in the case the amount of the metal atoms is greater than the previously described range, the carbonic acid esters can be used after reducing the amount of metal atoms to within the previously described range by removing by, for example, cleaning with solvent, distillative purification, crystallization or using an ion exchange resin, or removing with a chelating resin.

Note that since metal atoms contained within the above range in carbonic acid esters are not recognized to have catalytic action in reactions between carbonic acid esters and amine compounds in nearly all cases, in this sense, they are clearly distinguished from catalysts used for the production of carbamic acid esters to be described later.

Since the amount of metal components contained in the diaryl carbonate can be quantified by various known methods, such as atomic absorption analysis, inductively coupled plasma-atomic emission spectrometry, inductively coupled plasma mass spectrometry, fluorescent X-ray analysis, X-ray photoelectron spectroscopy, electron beam microanalysis or secondary ion mass spectrometry, the method can be selected in consideration of the form of the sample and the amount of metal components contained therein.

The carbonic acid esters are preferably produced according to the following steps (1) and (2) in the case the carbonic acid ester is a dialkyl carbonate, or are produced according to the following steps (1) to (3) in the case the carbonic acid ester is a diaryl carbonate, namely:

step (1): (dialkyl carbonate formation step) obtaining a reaction mixture containing a dialkyl carbonate by reacting an organic tin compound having a tin-oxygen-carbon bond and carbon dioxide, step (2): (dialkyl carbonate separation step) obtaining a residue liquid together with separating the dialkyl carbonate from the reaction mixture; and step (3): (diaryl carbonate production step) obtaining a diaryl carbonate by reacting the dialkyl carbonate separated in step (2) and an aromatic hydroxy compound A followed by recovering a by-product alcohol.

In addition, the following steps (4) and (5) can be carried out in addition to these steps (1) and (2) or steps (1) to (3), namely:

step (4): (organic tin compound regeneration step) forming an organic tin compound having a tin-oxygen-carbon bond and water by reacting the residue liquid obtained in step (2) with an alcohol followed by removing the water from the reaction system; and step (5): (recycling step) reusing the organic tin compound having the tin-oxygen-carbon bond obtained in step (4) as the organic tin compound having the tin-oxygen-carbon bond of step (1).

Dialkyl tin compounds are preferably used for the organic tin compound used in step (1). Dialkyl tin compound refers to an organic tin compound in which two alkyl groups are bonded to a single tin atom.

Examples of these dialkyl tin compounds may include compounds selected from at least one type of compound selected from the group consisting of dialkyl tin compounds represented by the following formula (10) and tetraalkyl distannoxane compounds represented by the following formula (11):

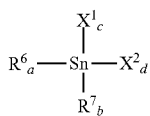
(10)

(wherein each of $R^6$ and $R^7$ independently represents a linear or branched alkyl group having 1 to 12 carbon atoms, each of $X^1$ and $X^2$ independently represents at least one type of substituent selected from the group consisting of an alkoxy group, an acyloxyl group and a halogen atom, a and b respectively represent integers of from 0 to 2, and a+b=2, and c and d respectively represent integers of from 0 to 2, and c+d=2);

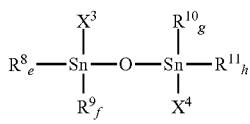
(11)

(wherein each of $R^8$, $R^9$, $R^{19}$ and $R^{11}$ independently represents a linear or branched alkyl group having 1 to 12 carbon atoms, $X^3$ and $X^4$ represent at least one type of substituent selected from the group consisting of an alkoxy group, an acyloxyl group and a halogen atom, and e, f, g and h respectively represent integers of from 0 to 2, e+f=2 and g+h=2).

Examples of $R^6$ and $R^7$ in the dialkyl tin catalyst represented by formula (10) above as well as examples of $R^8$, $R^9$, $R^{10}$ and $R^{11}$ in the tetraalkyl distannoxane compound represented by formula (11) above may include alkyl groups in the form of aliphatic hydrocarbon groups in which the number of carbon atoms constituting the group is a number selected from the group consisting of integers of from 1 to 12, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers) or a dodecyl group (including isomers). More preferable examples may include linear or branched alkyl groups in which the number of carbon atoms constituting the group is a number selected from the group consisting of integers of from 1 to 8, and although dialkyl tin compounds can be used in which the alkyl group is an alkyl group in which the number of carbon atoms constituting the group is outside the range indicated above, there are cases in which fluidity may be poor or productivity may be impaired. Moreover, an n-butyl group or n-octyl group is more preferable in consideration of ease of acquisition during industrial production.

$X^1$ and $X^2$ of the dialkyl tin compound represented by formula (10) above and $X^3$ and $X^4$ of the tetraalkyl distannoxane compound represented by formula (11) above may include at least one type of substituent selected from the group consisting of an alkoxy group, an acyloxyl group and a halogen atom, and in the case the group is an alkoxy group and/or an acyloxy group, the number of carbon atoms constituting the group is preferably a number selected from the group consisting of integers of from 0 to 12. Examples of such groups may include alkoxy groups composed of a linear or branched saturated alkyl group and an oxygen atom, such as a methoxy group, an ethoxy group, a propoxy group (including isomers), a butoxy group (including isomers), a pentyloxy group (including isomers), a hexyloxy group (including isomers), a heptyloxy group (including isomers), an octyloxy group (including isomers), a nonyloxy group (including isomers) or a decyloxy group (including isomers); acyloxyl groups composed of a linear or branched saturated alkyl group, carbonyl group and oxygen atom, such as an acetoxy group, a propionyloxy group, a butyryloxy group, a valeryloxy group or a lauroyloxy group; and halogen atoms such as a chloro group or bromo group. More preferable examples may include alkoxy groups having 4 to 8 carbon atoms in consideration of fluidity and solubility as well as use as a carbonic acid ester production catalyst.

Examples of dialkyl tin compounds represented by formula (10) may include dialkyl-dialkoxy tins such as dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dimethyl-dinonyloxy tin (including isomers), dimethyl-didecyloxy tin (including isomers), dibutyl-dimethoxy tin (including isomers), dibutyl-diethoxy tin (including isomers), dibutyl-dipropoxy tin (including isomers), dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dibutyl-dinonyloxy tin (including isomers), dibutyl-didecyloxy tin (including isomers), dioctyl-dimethoxy tin (including isomers), dioctyl-diethoxy tin (including isomers), dioctyl-dipropoxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers), dioctyl-dinonyloxy tin (including isomers) or dioctyl-didecyloxy tin (including isomers); dialkyl-diacyloxy tins such as dimethyl-diacetoxy tin, dimethyl-dipropionyloxy tin (including isomers), dimethyl-dibutyryloxy tin (including isomers), dimethyl-valeryloxy tin (including isomers), dimethyl-dilauroyloxy tin (including isomers), dibutyl-diacetoxy tin (including isomers), dibutyl-dipropionyloxy tin (including isomers), dibutyl-dibutyryloxy tin (including isomers), dibutyl-divaleryloxy tin (including isomers), dibutyl-dilauroyloxy tin (including isomers), dioctyl-diacetoxy tin (including isomers), dioctyl-dipropionyloxy tin (including isomers), dioctyl-dibutyryloxy tin (including isomers), dioctyl-valeryloxy tin (including isomers) or dioctyl-dilauroyloxy tin (including isomers); and, dialkyl-dihalide tins such as dimethyl-dichloro tin, dimethyl-dibromo tin, dibutyl-dichloro tin (including isomers), dibutyl-dibromo tin (including isomers), dioctyl-dichloro tin (including isomers) or dioctyl-dibromo tin (including isomers).

Among these, dialkyl tin dialkoxides such as dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dimethyl-dinonyloxy tin (including isomers), dimethyl-didecyloxy tin (including isomers), dibutyl-dimethoxy tin (including isomers), dibutyl-diethoxy tin (including isomers), dibutyl-dipropoxy tin (including isomers), dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dibutyl-dinonyloxy tin (including isomers), dibutyl-didecyloxy tin (including isomers), dioctyl-dimethoxy tin (including isomers), dioctyl-diethoxy tin (including isomers), dioctyl-dipropoxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers), dioctyl-dinonyloxy tin (including isomers) or dioctyl-didecyloxy tin (including isomers) are preferable, dialkyl-dialkoxy tins such as dibutyl-dipropoxy tin (including isomers), dibutyl-dibutyryloxy tin (including isomers), dibutyl-dipentyloxy tin (including isomers), dibutyl-dihexyloxy tin (including isomers), dibutyl-diheptyloxy tin (including isomers), dioctyl-dipropoxy tin (including isomers), dioctyl-dibutoxy tin (including isomers), dioctyl-dipentyloxy tin (including isomers), dioctyl-dihexyloxy tin (including isomers) or dioctyl-diheptyloxy tin (including isomers) are more preferable, and dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers) or dioctyl-dioctyloxy tin (including isomers) is even more preferable.

Although the monomer structure is shown for the dialkyl tin compounds represented by the formula (10), this may be a polymer structure or an associate.

Examples of tetraalkyl dialkoxy distannoxanes represented by the formula (11) may include 1,1,3,3-tetraalkyl-1,3-dialkoxy distannoxanes such as 1,1,3,3-tetramethyl-1,3-dimethoxy distannoxane, 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetramethyl-1,3-dinonyloxy distannoxane (including isomers), 1,1,3,3-tetramethyl-1,3-didecyloxydistannoxane (including isomers), 1,1,3,3-tetrabutyl-1,3-dimethoxy distannoxane (including isomers), 1,1,3,3-tetrabutyl-1,3-diethoxy distannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetrabutyl-1,3-dinonyloxy distannoxane (including isomers), 1,1,3,3-tetrabutyl-1,3-didecyloxy distannoxane (including isomers), 1,1,3,3-tetraoctyl-1,3-dimethoxy distannoxane (including isomers), 1,1,3,3-tetraocyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers), 1,1,3,3-tetraoctyl-1,3-dioctyloxy distannoxane (including isomers), 1,1,3,3-tetraoctyl-1,3-dinonyloxy distannoxane (including isomers) or 1,1,3,3-tetraoctyl-1,3-didecyloxy distannoxane (including isomers); 1,1,3,3-tetraalkyl-1,3-diacyloxy distannoxanes such as 1,1,3,3-tetramethyl-1,3-diacetoxy distannoxane, 1,1,3,3-tetramethyl-1,3-dipropionyloxy distannoxane (including isomers), 1,1,3,3-tetramethyl-1,3-dibutyryloxy distannoxane (including isomers), 1,1,3,3-tetramethyl-1,3-divaleryloxy distannoxane (including isomers), 1,1,3,3-tetramethyl-1,3-dilauroyloxy distannoxane (including isomers), 1,1,3,3-tetrabutyl-1,3-diacetoxy distannoxane (including isomers), 1,1,3,3-tetrabutyl-1,3-dipropionyloxy distannoxane (including isomers), 1,1,3,3-tetrabutyl-1,3-dibutyryloxy distannoxane (including isomers), 1,1,3,3-tetrabutyl-1,3-divaleryloxy distannoxane (including isomers), 1,1,3,3-tetrabutyl-1,3-dilauroyloxy distannoxane (including isomers), 1,1,3,3-tetraoctyl-1,3-diacetoxy distannoxane (including isomers), 1,1,3,3-tetraoctyl-1,3-dipropionyloxy distannoxane (including isomers), 1,1,3,3-tetraoctyl-1,3-dibutyryloxy distannoxane (including isomers), 1,1,3,3-tetraoctyl-1,3-divaleryloxy distannoxane (including isomers) or 1,1,3,3-tetraoctyl-1,3-dilauroyloxy distannoxane (including isomers); and, 1,1,3,3-tetraalkyl-1,3-dihalide distannoxanes such as 1,1,3,3-tetramethyl-1,3-dichloro distannoxane, 1,1,3,3-tetramethyl-1,3-dibromo distannoxane, 1,1,3,3-tetrabutyl-1,3-dichloro distannoxane (including isomers), 1,1,3,3-tetrabutyl-1,3-dibromo distannoxane (including isomers), 1,1,3,3-tetraocyl-1,3-dichloro distannoxane (including isomers) or 1,1,3,3-tetraocyl-1,3-dibromo distannoxane (including isomers).

Among these, 1,1,3,3-tetraalkyl-1,3-dialkoxy distannoxanes such as 1,1,3,3-tetramethyl-1,3-dimethoxy distannoxane, 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetramethyl-1,3-dinonyloxy distannoxane (including isomers), 1,1,3,3-tetramethyl-1,3-didecyloxy distannoxane (including isomers), 1,1,3,3-tetrabutyl-1,3-dimethoxy distannoxane (including isomers), 1,1,3,3-tetrabutyl-1,3-diethoxy distannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetrabutyl-1,3-dinonyloxy distannoxane (including isomers), 1,1,3,3-tetrabutyl-1,3-didecyloxy distannoxane (including isomers), 1,1,3,3-tetraoctyl-1,3-dimethoxy distannoxane (including isomers), 1,1,3,3-tetraocyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers), 1,1,3,3-tetraoctyl-1,3-dioctyloxy distannoxane (including isomers), 1,1,3,3-tetraoctyl-1,3-dinonyloxy distannoxane (including isomers) or 1,1,3,3-tetraoctyl-1,3-didecyloxy distannoxane (including isomers) are preferable, and 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers) or 1,1,3,3-tetraoctyl-1,3-dioctyloxy distannoxane (including isomers) is more preferable.

Although the monomer structure is shown for the tetraalkyl dialkoxy distannoxanes represented by formula (11) above, this may also be a polymer structure or an associate.

In general, organic tin compounds easily adopt an associated structure, and although, for example, dialkyl tin dialkoxy tin is known to form a dimer structure, and tetraalkyl dialkoxy distannoxanes are known to be present by forming a ladder structure in which two or three molecules are associated, even in cases in which there are changes in this associated state, the representation of a compound in the form of a monomer structure is common for a person with ordinary skill in the art.

In addition, the previously indicated dialkyl tin compound may be used alone or two or more types may be used as a mixture.

A previously disclosed production process (such as that disclosed in WO 2005/111049) can preferably be used as the process for producing the dialkyl tin compounds. This process is a process for producing the dialkyl tin compounds from dialkyl tin oxides and alcohols Examples of alcohols used in the present embodiment may lude alcohols such as methanol, ethanol, propanol (including isomers), butanol (including isomers), pentanol (including isomers), hexanol (including isomers), heptanol (including isomers), octanol (including isomers), nonanol (including isomers) or decanol (including isomers), and an alcohol is preferably used in which the number of carbon atoms constituting is a number selected from the group consisting of integers of from 1 to 12.

Dialkyl tin oxides represented by the following formula (12) are used for the dialkyl tin oxides used in the alkyl tin alkoxide synthesis process:

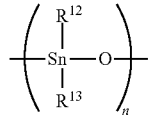

(12)

(wherein each of $R^{12}$ and $R^{13}$ independently represents a linear or branched alkyl group having 1 to 12 carbon atoms).

Examples of $R^{12}$ and $R^{13}$ may include alkyl groups in the form of aliphatic hydrocarbon groups having 1 to 12 carbon atoms, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers) or a dodecyl group (including isomers). More preferable examples may include linear or branched saturated alkyl groups having 1 to 8 carbon atoms, while even more preferable examples may include an n-butyl group and an n-octyl group.

Tetraalkyl dialkoxy distannoxanes and/or dialkyl tin dialkoxides are obtained by dehydration reaction of the alcohols and the dialkyl tin oxides while removing the water formed from the system. The temperature at which the reaction is carried out is, for example, within a range of from 80 to 180° C., and in order to distill off the water formed from the system, although varying according to the reaction pressure, a temperature of from 100 to 180° C. is preferable. Although a high temperature is preferable for the reaction temperature to accelerate the reaction rate, since undesirable reactions such as decomposition may also occur at high temperatures thereby decreasing yield, the reaction temperature is more preferably within a range of from 100 to 160° C. The reaction pressure is a pressure that allows water formed to be removed from the system, and the reaction is carried out at a pressure of from 20 to $1 \times 10^6$ Pa, although varying according to the reaction temperature. There are no particular limitations on the reaction time of the dehydration reaction, and is generally from 0.001 to 50 hours, preferably from 0.01 to 10 hours and more preferably from 0.1 to 2 hours. The reaction may be terminated once the desired alkyl tin alkoxide composition has been obtained. Progression of the reaction is also determined by measuring the amount of water extracted outside the system, and can also be determined by a method using $^{119}$Sn-NMR by sampling the reaction liquid. In order to produce the mixture of the present embodiment in step (1), the reaction is terminated after confirming the obtaining of a composition in which the molar ratio of tetraalkyl dialkoxy distannoxane and dialkyl tin dialkoxide contained in the alkyl tin alkoxide composition obtained in the above reaction, when expressed as the combined molar percentage of both, is within a range of from 0:100 to 80:20 and more preferably within a range of from 10:90 to 70:30. The alcohol used may be used while still present in the reaction system, and the alcohol may also be used by distilling off the alcohol depending on the case. Since there is the advantage of being able to reduce the size of the reaction vessels of the other steps, it is preferable to remove as much of the alcohol as possible. Removal by known distillation is preferable for the removal method, and known distillation equipment can be used for the distiller used for distillation. A thin film distillation apparatus is preferably used for the distillation apparatus since the alcohol can be removed in a short period of time. There are no particular limitations on the type of reaction vessel of the dehydration reaction, and a known tank type or a column type reaction vessel can be used. A low boiling point reaction mixture containing water is extracted in gaseous form from the reaction vessel by distillation, while a high boiling point reaction mixture containing a produced alkyl tin alkoxide or alkyl tin alkoxide mixture is extracted in the form of a liquid from a lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a column-type reactor are preferable from the viewpoint of efficiently shifting the equilibrium to the products side, while a structure having a large gas-liquid contact area is preferable for being able to rapidly transfer the water formed to the gaseous phase. Although continuous methods using a multitubular reactor, a multistage distillation column or a packed column packed with a packing can also be used, since the dialkyl tin oxide used in this step is generally a solid, it is preferable to employ a method in which the reaction is first carried out in a tank-type reaction vessel followed by increasing the content of dialkyl tin dialkoxide in a column-type reaction vessel. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Step (1) is a step for producing carbonic acid esters by reacting dialkyl tin compounds produced according to the process described above with gaseous carbon dioxide. A previously disclosed carbonic acid ester production process (such as that disclosed in WO 03/055840 or WO 04/014840) is preferably used in this step.

The alkyl tin compounds supplied to this step may be supplied from an alkyl tin alkoxide synthesis step at the start of production, or from a dialkyl tin compound production step of step (4) to be described later through step (5) during continuous production.

In step (1), the above-mentioned dialkyl tin alkoxide and gaseous carbon dioxide are absorbed and undergo a chemical reaction to obtain a mixture containing a carbon dioxide-bonded form of the dialkyl tin alkoxide. During this chemical reaction, the dialkyl tin alkoxide is reacted in a liquid form. The dialkyl tin alkoxide is preferably put into liquid form by heating to obtain the dialkyl tin alkoxide in the liquid form in the case the dialkyl tin alkoxide is in a solid form. In addition, it may also be put into liquid form by a solvent and the like. Although varying according to the reaction temperature, the reaction pressure is preferably within a range of from normal pressure to 1 MPa and more preferably within a range of from normal pressure to 0.6 MPa. Although varying according to the reaction pressure, the reaction temperature is preferably within a range of from −40 to 80° C., and in consideration of fluidity during transfer, more preferably from 0 to 80° C. and most preferably within a range of from normal temperature (e.g., 20° C.) to 80° C. The reaction time may be within a range of from several seconds to 100 hours, and in consideration of productivity and the like, is preferably from several minutes to 10 hours. A known tank type reaction vessel or a column type reaction vessel can be used for the reaction vessel. In addition, a plurality of reaction vessels may be used in combination. Since the reaction is a reaction between carbon dioxide gas (gas) and an alkyl tin alkoxide composition (liquid), in order to carry out the reaction efficiently, it is preferable to increase the contact surface area between the gas and liquid by increasing the gas-liquid interface. Known findings can be used for the method for reacting while increasing the gas-liquid interface in this manner, and examples of preferable methods thereof may include increasing the stirring speed or generating bubbles in the liquid in the case of a tank type reaction vessel, and using a packed column or using a plate column in the case of a column type reaction vessel. Examples of such column type reaction vessels may include plate column types using a tray such as a bubble tray, a porous plate tray, a valve tray or a counter-current tray, and packed column types packed with various types of packing materials such as a raschig ring, a lessing ring, a pole ring, a Berl saddle, an Interlock saddle, a Dixon packing, a McMahon packing, Helipak, a Sulzer packing or Mellapak. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Since the reaction is normally an exothermic reaction, the reaction vessel may be cooled or it may be cooled by dissipation of heat there from. Alternatively, the reaction vessel may also be heated if the purpose is combining with a carbonic acid esterification reaction. A known method such as a method using a heat jacket or a method using an internal coil can be used to heat and cool the reaction vessel. The carbon dioxide gas and alkyl tin alkoxide composition supplied to the reaction vessel may be supplied separately to the reaction vessel or they may be mixed prior to supplying to the reaction vessel. These components may also be supplied from a plurality of locations in the reaction vessel. Completion of the reaction can be determined by, for example, $^{119}$Sn-NMR analysis.

Next, a reaction liquid containing carbonic acid ester is obtained from the carbon dioxide-bonded form of the dialkyl tin alkoxide obtained in the above manner according to the method described below.

Although the reaction temperature is within a range of from 110 to 200° C., and a high temperature is preferable for the reaction temperature in order to accelerate the reaction rate, since undesirable reactions such as decomposition also occur at high temperatures thereby decreasing yield, the reaction temperature is more preferably within a range of from 120 to 180° C., the reaction time is preferably within a range of from 0.1 to 10 hours, and the reaction pressure is within a range of from 1.5 to 20 MPa and preferably from 2.0 to 10 MPa. The reaction is terminated after the desired carbonic acid ester has formed in the reaction vessel. Progression of the reaction can be confirmed by, for example, sampling the reaction liquid in the reaction vessel, and analyzing the carbonic acid ester formed by a method such as $^1$H-NMR or gas chromatography. For example, the reaction may be terminated after the carbonic acid ester has been formed at a molar ratio of 10% or more of the dialkyl tin alkoxide and/or carbon dioxide-bonded form of the dialkyl tin alkoxide contained in the dialkyl tin alkoxide and/or carbon dioxide-bonded form of the dialkyl tin alkoxide, and in the case of desiring to increase the yield of the carbonic acid ester, the reaction may be terminated after allowing to continue until the value reaches 90% or more. A known reaction vessel can be used for the reaction vessel, and a column type reaction vessel or a tank type reaction vessel can be used preferably. Although known materials may be used for the materials of the reaction vessel and lines provided they do not have a detrimental effect, materials such as SUS304, SUS316 or SUS316L are inexpensive and can be used preferably. Known process apparatuses such as a flow meter, thermometer and other measuring instruments or a reboiler, a pump or a condenser and the like may be added as necessary, a known method such as steam or a heater may be used for heating, and a known method such as air cooling, cooling water or brine can be used for cooling.

Step (2) in the present embodiment is a step for obtaining a residue liquid from the reaction liquid containing carbonic acid ester obtained in step (1) above together with separating and recovering the carbonic acid ester. A known method or apparatus can be preferably used for the separation method, and a preferable method is distillation.

Carbonic acid ester and the residue liquid are obtained by batch, semi-batch or continuous distillation of the reaction liquid transferred from step (1) above. A preferable example of a distillation method may include supplying the reaction liquid to a distiller, separating the carbonic acid ester in the form of a gaseous phase component from a top of the distiller outside the system, and extracting the residue liquid in the form of a liquid component from a bottom of the distiller. Although varying according to the boiling point of the carbonic acid ester and pressure, the temperature in this step is within a range of from normal temperature (e.g., 20° C.) to 200° C., and since there are cases in which denaturation of tin compounds in the residue liquid may occur or the amount of carbonic acid ester may decrease due to a reverse reaction at high temperatures, the reaction temperature is preferably within a range of from normal temperature (e.g. 20° C.) to 150° C. Although varying according to the type of carbonic acid ester and temperature at which the reaction is carried out, the reaction is generally carried out at normal pressure to reduced pressure conditions, and in consideration of productivity, the pressure is more preferably within a range of from 100 Pa to 80 KPa and most preferably within a range of from 100 Pa to 50 KPa. The reaction can be carried out a reaction time within a range of from 0.01 to 10 hours, and since there are cases in which tin compounds contained in the reaction liquid are denatured and cases in which the amount of carbonic acid ester decreases due to a reverse reaction when the reaction is carried out for a long period of time at high temperatures, the reaction time is preferably within a range of from 0.01 to 0.5 hours and most preferably within a range of from 0.01 to 0.3 hours. A known distiller can be used for the distiller, a column type distiller or a tank type distiller can be used preferably, or a plurality of types can be used in combination. More preferable examplesa of the distillers may include a thin film evaporator and a thin film distiller, and a thin film evaporator provided with a distillation column or a thin film distiller is most preferable. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Step (3) is a step for obtaining a diaryl carbonate by reacting the dialkyl carbonate separated in step (2) and an aromatic hydroxy compound A followed by recovering a by-product alcohol. Aromatic hydroxy compound as mentioned here refers to a compound corresponding to a compound $R^1OH$ in which a hydrogen atom is added to a group $R^1O$ (wherein $R^1$ represents an aromatic group as previously defined, and O represents an oxygen atom) constituting the diaryl carbonate represented by formula (8) above. Specific examples of preferably used aromatic hydroxy compound A may include phenol, mono-substituted phenols such as methylphenol (including isomers), ethylphenol (including isomers), propylphenol (including isomers), butylphenol (including isomers), pentylphenol (including isomers) or hexylphenol (including isomers); di-substituted phenols such as dimethylphenol (including isomers), diethylphenol (including isomers), dipropylphenol (including isomers), methylethylphenol (including isomers), methylpropylphenol (including isomers), methylbutylphenol (including isomers), methylpentylphenol (including isomers), ethylpropylphenol (including isomers) or ethylbutylphenol (including isomers); tri-substituted phenols such as trimethylphenol (including isomers), triethylphenol (including isomers), dimethylethylphenol (including isomers), dimethylpropylphenol (including isomers) or dimethylbutylphenol (including isomers); and naphthol (including isomers).

Step (3) in the present embodiment is a step for obtaining diaryl carbonate by reacting a component mainly containing carbonic acid ester separated in step (2) and the aromatic hydroxy compound A. Numerous processes for obtaining alkyl aryl carbonates and diaryl carbonates from dialkyl carbonates and aromatic hydroxy compounds have been previously proposed, and these technologies can be preferably applied in the present embodiment as well.

The reaction of step (3) comprises a transesterification reaction between the carbonic acid ester and the aromatic hydroxy compound, and a disproportionation reaction of the dialkyl aryl carbonate obtained in the transesterification reaction.

The transesterification reaction is an equilibrium reaction and in order to allow the reaction to proceed advantageously, it is preferable to carry out the reaction while extracting the alcohol formed by elimination in the transesterification reaction, and in this case, the boiling point of the aromatic hydroxy compound used in step (3) is preferably higher than the boiling point of the alkyl alcohol constituting the alkyl carbonate obtained in step (2). In particular, in the case of carrying out steps (1) to (3) continuously by repeating one or more times, the boiling point of the alkyl alcohol is preferably lower than the standard boiling point of the aromatic hydroxy compound, and the difference between the boiling points thereof is preferably 2° C. and more preferably 10° C. in consideration of ease of separation.

Examples of dialkyl carbonates used in step (3) may include dimethyl carbonate, diethyl carbonate, dipropyl carbonate (including isomers), dibutyl carbonate (including isomers), dipentyl carbonate (including isomers), dihexyl carbonate (including isomers), diheptyl carbonate (including isomers), dioctyl carbonate (including isomers), dinonyl carbonate (including isomers), didecyl carbonate (including isomers), dicyclopentyl carbonate (including isomers), dicyclohexyl carbonate (including isomers), dicycloheptyl carbonate (including isomers), dibenzyl carbonate, diphenethyl carbonate (including isomers), di(phenylpropyl)carbonate (including isomers), di(phenylbutyl)carbonate (including isomers), di(chlorobenzyl)carbonate (including isomers), di(methoxybenzyl)carbonate (including isomers), di(methoxymethyl)carbonate (including isomers), di(methoxyethyl)carbonate (including isomers), di(chloroethyl)carbonate (including isomers), di(cyanoethyl)carbonate (including isomers), methylethyl carbonate, methylpropyl carbonate (including isomers), methylbutyl carbonate (including isomers), ethylpropyl carbonate (including isomers), ethylbutyl carbonate (including isomers), ethylene carbonate and propylene carbonate. The carbonic acid ester used may be one type or a mixture.

Among these dialkyl carbonates, those dialkyl carbonates that are used preferably in the present embodiment are alcohols in which the standard boiling point of the alcohol constituting the carbonic acid ester is higher than the standard boiling point of water in the form of alkyl alcohols having an alkyl group having 4 to 12 carbon atoms, alkenyl alcohols having a linear or branched alkenyl group having 4 to 12 carbon atoms, cycloalkyl alcohols and aralkyl alcohols. In order to allow the reaction carried out in step (3) to proceed advantageously, an alcohol having a standard boiling point lower than the standard boiling point of the aromatic hydroxy compound used in step (3) is more preferable in consideration of removing the alcohol formed in the reaction of step (3).

Namely, a dialkyl carbonate is preferable that is composed of an alcohol having a standard boiling point higher than the standard boiling point of water but lower than the standard boiling point of the aromatic hydroxy compound.

The amount of the aromatic hydroxy compound used in step (3) can be within a range of a stoichiometric ratio of from 0.1 to 10000 times the amount of dialkyl carbonate separated in step (2) and used in step (3). Since the reaction of step (3) is mainly an equilibrium reaction, although a large amount of the aromatic hydroxy compound is advantageous, since an increase in the amount used results in the need for a larger reaction vessel as well as a large distillation column for subsequently separating the product, the amount of the aromatic hydroxy compound is preferably within a range of from 1 to 1000 times and more preferably within a range of from 1 to 100 times the amount of the dialkyl carbonate.

Although the compounds supplied to step (3) mainly contains dialkyl carbonate, aromatic hydroxy compound and, as necessary, a catalyst, impurities may be present provided they do not have a particularly detrimental effect on the reaction.

Although products in the form of alcohol, alkyl aryl carbonate and diaryl carbonate and the like may be contained among these supplied raw materials, since the reaction is reversible, the reaction rate of the raw materials decreases in the case the concentrations of these products are excessively high, thereby making this undesirable. Although able to be varied according to the type and amount of catalyst and the reaction conditions, the weight ratio of the supplied dialkyl carbonate and aromatic hydroxy compound is generally such that the aromatic hydroxy compound is preferably supplied at a molar ratio within a range of from 0.01 to 1000 times the dialkyl carbonate in the supplied raw materials.

Although varying according to the reaction conditions and type and internal structure of the reaction vessel, the reaction time of the transesterification reaction of step (3) is generally from 0.001 to 50 hours, preferably from 0.01 to 10 hours and more preferably from 0.05 to 5 hours. The reaction temperature refers to the temperature within the reaction vessel, and although varying according to the types of raw materials used in the form of the dialkyl carbonate and the aromatic hydroxy compound, is generally within a range of from 50 to 350° C. and preferably from 100 to 280° C. In addition, although varying according to the types of raw material compounds used, the reaction temperature and the like, the reaction pressure may be decreased pressure, normal pressure or increased pressure, and the reaction is generally carried out within a range of from 10 Pa to 20 MPa.

Although the use of a solvent is not necessarily required in the present embodiment, a suitable inert solvent can be used as a reaction solvent for the purpose of, for example, facilitating the reaction procedure, examples of which may include ethers, aliphatic hydrocarbons, aromatic hydrocarbons, aliphatic hydrocarbon halides and aromatic hydrocarbon halides. In addition, an inert gas such as nitrogen, helium or argon may also be present in the reaction system as an inert substance in the reaction, and the above inert gases and low boiling point organic compounds inactive in the reaction may be introduced in gaseous form from the lower portion of a continuous multistage distillation column for the purpose of accelerating the removal of low boiling point by-products formed by distillation.

A catalyst may be added when carrying out the transesterification reaction of step (3). Although alkyl aryl carbonate and diaryl carbonate are obtained from carbonic acid ester by transesterification as previously described, since the equilibrium of this transesterification reaction is biased towards the reactants and since the reaction rate is slow, when producing diaryl carbonate by this process, several proposals have been made to improve these, and a known process can be preferably used in the present embodiment.

Although varying according to the type of catalyst used, the type of reaction vessel, the types and weight ratio of the carbonic acid ester and aromatic hydroxy compound and reaction conditions such as the reaction temperature and reaction pressure, the amount of catalyst in the case of using a catalyst in the present embodiment is generally from 0.0001 to 50% by weight when expressed as the ratio to the total amount of supplied raw materials in the form of the carbonic acid ester and aromatic hydroxy compound. In addition, in the case of using a solid catalyst, the catalyst is preferably used at an amount of from 0.01 to 75% by volume based on the volume of the empty column of the reaction vessel.

Numerous metal-containing catalysts are known in proposals relating to catalysts for increasing reaction rate, and known transesterification reaction catalysts can be used in the present embodiment as well. In a process for producing alkyl aryl carbonate and/or a mixture of alkyl aryl carbonate and diaryl carbonate by reacting the carbonic acid esters and the aromatic hydroxy compounds, Lewis acids such as transition metal hydrides or compounds that purify Lewis acids, tin compounds such as organic tin alkoxides or organic tin oxides, salts and alkoxides of alkaline earth metals or alkaline metals, lead compounds, metal complexes such as those of copper, iron or zirconium, titanic acid esters, mixtures of Lewis acids and protic acids, Sc, Mo, Mn, Bi or Te compounds, and ferric acetate have been proposed as examples of such catalysts. Although formation of diaryl carbonate can occur by the transesterification reaction only, it is also formed by a disproportionation reaction of the alkyl aryl carbonate formed in the transesterification reaction. Here, a disproportionation reaction refers to a reaction in which dialkyl carbonate and diaryl carbonate are formed from two molecules of alkyl aryl carbonate. Although the alkyl aryl carbonate further reacts with the aromatic hydroxy compound to become a diaryl carbonate, since the disproportionation reaction is faster, in the case of desiring to obtain a diaryl carbonate, diaryl carbonate is obtained by disproportionating the alkyl aryl carbonate. Both of these reactions are equilibrium reactions. It is advantageous to allow the reaction to proceed while extracting alkyl alcohol in the transesterification reaction for producing alkyl aryl carbonate, and advantageous to allow the reaction to proceed while extracting dialkyl carbonate in the disproportionation step. Thus, the preferable reaction conditions differ in each stage. Although it is necessary to carry out the reaction by dividing into two stages in the case of carrying out the reaction continuously, in the case of carrying out the reaction in batches, the reaction can also be carried out sequentially within the same reaction vessel.

Thus, a catalyst that catalyzes the disproportionation reaction may also be present with the previously described transesterification catalyst. Numerous examples of such catalysts have been proposed, examples of which may include Lewis acids and transition metal compounds capable of generating Lewis acids, polymeric tin compounds, compounds represented by the general formula R—X(=O)OH (wherein X is selected from the group consisting of Sn and Ti, while R is selected from the group consisting of monovalent hydrocarbon groups), mixtures of Lewis acids and protic acids, lead catalysts, titanium and zirconium compounds, tin compounds and Sc, Mo, Mn, Bi or Te compounds.

The disproportionation step is a step in which dialkyl carbonate and diaryl carbonate are obtained by disproportionating the alkyl aryl carbonate obtained in the transesterification step. As was previously described, a disproportionation catalyst may be added when carrying out the transesterification reaction to carry out the transesterification reaction and disproportionation reaction simultaneously, or the transesterification reaction and disproportionation reaction may be carried out separately and continuously or in batches. In addition, although there are cases in which diaryl carbonate is obtained simultaneous to alkyl aryl carbonate in the transesterification reaction as well in the case of carrying out the transesterification reaction and disproportionation reaction separately, in this case as well, the disproportionation reaction can be carried out as is. As was previously indicated, the disproportionation reaction is a step in which alkyl aryl carbonate is obtained by a transesterification reaction between the dialkyl carbonate and the aromatic hydroxy compound, and in order to allow this equilibrium reaction to proceed advantageously, it is advantageous to employ a method that allows the reaction to proceed while extracting alcohol. Since the disproportionation reaction is also subjected to the restriction of equilibrium, if attempting to allow the reaction to proceed advantageously, a method that allows the reaction to proceed while extracting either the dialkyl carbonate or diaryl carbonate formed in the disproportionation reaction outside the system is advantageous. In the present embodiment, it is preferable to carry out the disproportionation reaction while extracting the dialkyl carbonate outside the system by selecting the respective alkoxy groups and aryl groups so that the dialkyl carbonate of the products boils at a lower temperature than the diaryl carbonate. The extracted dialkyl carbonate may be used by returning to a step prior to the disproportionation reaction. If the amount of diaryl carbonate produced is to be increased, it is preferable to use the extracted dialkyl carbonate by returning to the transesterification step.

A catalyst of a disproportionation reaction may be used in the disproportionation reaction. Numerous examples of such catalysts have been proposed. Examples of such catalysts that have been proposed may include Lewis acids and transition metal compounds capable of generating Lewis acids, polymeric tin compounds, compounds represented by the general formula R—X(=O)OH (wherein X is selected from the group consisting of Sn and Ti, while R is selected from the group consisting of monovalent hydrocarbon groups), mixtures of Lewis acids and protic acids, lead catalysts, titanium and zirconium compounds, tin compounds and Sc, Mo, Mn, Bi or Te compounds.

The same catalysts as the transesterification catalysts used in the transesterification step can be used for the disproportionation reaction catalyst in the present embodiment.

The alkyl aryl carbonate used in the disproportionation step is an alkyl aryl carbonic acid ester. Examples of alkyl aryl carbonates may include methylphenyl carbonate, ethylphenyl carbonate, propylphenyl carbonate (including isomers), butylphenyl carbonate (including isomers), allylphenyl carbonate (including isomers), pentylphenyl carbonate (including isomers), hexylphenyl carbonate (including isomers), heptylphenyl carbonate (including isomers), octyltolyl carbonate (including isomers), nonyl(ethylphenyl)carbonate (including isomers), decyl(butylphenyl) carbonate (including isomers), methyltolyl carbonate (including isomers), ethyltolyl carbonate (including isomers), propyltolyl carbonate (including isomers), butyltolyl carbonate (including isomers), allyltolyl carbonate (including isomers), methylxylyl carbonate (including isomers), methyl(trimethylphenyl)carbonate (including isomers), methyl(chlorophenyl)carbonate (including isomers), methyl(nitrophenyl)carbonate (including isomers), methyl(methoxyphenyl)carbonate (including isomers), methyl(pyridyl)carbonate (including isomers), ethylcumyl carbonate (including isomers), methyl(benzoylphenyl)carbonate (including isomers), ethylxylyl carbonate (including isomers) and benzylxylyl carbonate (including isomers). These alkyl aryl carbonates may be of one type or a mixture of two or more types.

Among these alkyl aryl carbonates, those which are preferably used in the present embodiment are those in which the alcohol constituting the alkyl aryl carbonate is an alcohol having a boiling point higher than that of water, the boiling point of the alcohol constituting the alkyl aryl carbonate is lower than the boiling point of the aromatic hydroxy compound constotuting the alkyl aryl carbonate, is selected from, for example, alkyl alcohols having a linear or branched alkyl group having 4 to 12 carbon atoms, alkenyl alcohols having a linear or branched alkenyl group having 4 to 12 carbon atoms, cycloalkyl alcohols and aralkyl alcohols, and when considering the removal of dialkyl carbonate formed in the disproportionation reaction, is preferably a dialkyl carbonate having a boiling point lower than that of the diaryl carbonate obtained in the disproportionation reaction to enable the disproportionation reaction to proceed advantageously. As examples of such optimum combinations, the alcohol, the alcohol corresponding to the alkoxy group of a metal compound having a metal-carbon-oxygen bond represented by the previously mentioned formulas (9) and (10), and the alcohol constituting the dialkyl carbonate are alcohols selected from the group consisting of pentanol (including isomers), hexanol (including isomers) and heptanol (including isomers), while the aromatic hydroxy compound is an aromatic hydroxy compound selected from phenol and cresol.

Although compounds supplied to the disproportionation reaction mainly contain alkyl aryl carbonate and a catalyst as necessary, impurities may also be present provided they do not have a particularly detrimental effect on the reaction.

Although varying according to the type of catalyst used, the type of reaction vessel, the type and amount of the alkyl aryl carbonate and reaction conditions such as the reaction temperature and reaction pressure, the amount of catalyst in the case of using a catalyst in the present embodiment is generally from 0.0001 to 50% by weight when expressed as the ratio to the total amount of supplied raw materials in the form of the alkyl aryl carbonate. In addition, in the case of using a solid catalyst, the catalyst is preferably used at an amount of from 0.01 to 75% by volume based on the volume of the empty column of the reaction vessel.

Although alcohol, aromatic hydroxy compound and diaryl carbonate and the like may be contained among these supplied raw materials, since the reaction is reversible, the reaction rate of the raw materials decreases in the case the concentrations of these components are excessively high, thereby making this undesirable.

Although varying according to the reaction conditions and type and internal structure of the reaction vessel, the reaction time of the disproportionation reaction is generally from 0.001 to 50 hours, preferably from 0.01 to 10 hours and more preferably from 0.05 to 5 hours. Although varying according to the type of alkyl aryl carbonate used, the reaction temperature is generally within a range of from 50 to 350° C. and preferably from 100 to 280° C. In addition, although varying according to the types of raw material compounds used, the reaction temperature and the like, the reaction pressure may be decreased pressure, normal pressure or increased pressure, and the reaction is generally carried out within a range of from 10 Pa to 20 MPa.

Although the use of a solvent is not necessarily required in the disproportionation step of the present embodiment, a suitable inert solvent can be used as a reaction solvent for the purpose of, for example, facilitating the reaction procedure, examples of which may include ethers, aliphatic hydrocarbons, aromatic hydrocarbons, aliphatic hydrocarbon halides and aromatic hydrocarbon halides. In addition, an inert gas such as nitrogen, helium or argon may also be present in the reaction system as an inert substance in the reaction, and the above inert gases and low boiling point organic compounds inactive in the reaction may be introduced in gaseous form from the lower portion of a continuous multistage distillation column for the purpose of accelerating the distillation of low boiling point by-products formed.

Following completion of the disproportionation reaction, diaryl carbonate is obtained by removing the catalyst, alkyl aryl carbonate, aromatic hydroxy compound and alcohol by known methods.

There are no particular limitations on the type of reaction vessel used in the transesterification and disproportionation steps, and various known methods are used, examples of which may include types using a stirring tank, a multistage stirring tank or a multistage distillation column and combinations thereof. Batch type or continuous type reaction vessels can be used for these reaction vessels. Methods using a multistage distillation column are preferable from the viewpoint of efficiently shifting the equilibrium to the products side, and a continuous method using a multistage distillation column is particularly preferable. A multistage distillation column refers to a distillation column having multiple stages in which the number of theoretical plates of distillation is 2 or more, and any multistage distillation column may be used provided it allows continuous distillation. Any multistage distillation column can be used for the multistage distillation column provided it is ordinarily used as a multistage distillation column, examples of which may include tray column types using a bubble tray, a porous plate tray, a valve tray or a counter-current tray, and packed column types packed with various types of packing materials such as a raschig ring, a lessing ring, a pole ring, a Berl saddle, an Interlock saddle, a Dixon packing, a McMahon packing, Helipak, a Sulzer packing or Mellapak. Moreover, a combination tray-packed column type is also used preferably that combines a tray portion with a portion packed with a packing material. In the case of carrying out a continuous method using a multistage distillation column, the starting substances and reactants are continuously supplied to a continuous multistage distillation column, and simultaneous to carrying out the transesterification reaction and/or disproportionation reaction between both substances in the liquid phase or gas-liquid phase in the presence of a metal-containing catalyst within the distillation column, a high boiling point reaction mixture containing the alkyl aryl carbonate and/or diaryl carbonate produced is extracted in liquid form from the lower portion of the distillation column, while a low boiling point reaction mixture containing by-products formed is continuously extracted in a gaseous state from the upper portion of the distillation column by distillation, thereby resulting in the production of diaryl carbonate.

Although the preceding description has indicated a production example of dialkyl carbonate and diaryl carbonate using a dialkyl tin compound, the following steps (4) and (5) can be carried out in addition to the above-mentioned steps (1) to (3), the steps (4) and (5) comprising the steps of:

step (4): forming an organic tin compound having a tin-oxygen-carbon bond and water by reacting the residue liquid obtained in step (2) with an alcohol followed by removing the water from the reaction system; and step (5): reusing the organic tin compound having the tin-oxygen-carbon bond obtained in step (4) as the organic tin compound having the tin-oxygen-carbon bond of step (1).

Step (4) is a step for regenerating a dialkyl tin compound by reacting the distillation residue obtained in step (2) with an alcohol.

Examples of alcohols used in this step may include alcohols such as methanol, ethanol, propanol (including isomers), butanol (including isomers), pentanol (including isomers), hexanol (including isomers), heptanol (including isomers), octanol (including isomers), nonanol (including isomers) or decanol (including isomers), and although an alcohol is preferably used in which the number of carbon atoms constituting the alcohol is a number selected from the group consisting of integers of 1 to 12, more preferably an alcohol is used that is the same as the alcohol used in the previously described alkyl tin alkoxide synthesis step.

The conditions of the dehydration reaction are preferably the same as the conditions of the above-mentioned alkyl tin alkoxide synthesis step. The reaction may be terminated once the desired alkyl tin alkoxide composition has been obtained. Progression of the reaction is also determined by measuring the amount of water extracted outside the system, and can also be determined by a method using $^{119}$Sn-NMR by sampling the reaction liquid. In order to produce the mixture of the present embodiment in step (1), the reaction is terminated after confirming the obtaining of a composition in which the molar ratio of tetraalkyl dialkoxy distannoxane and dialkyl tin dialkoxide contained in the alkyl tin alkoxide composition obtained in the above reaction, when expressed as the combined molar ratio of both, is within a range of from 0:100 to 80:20 and more preferably within a range of from 10:90 to 70:30. The alcohol used may be used while still present in the reaction system, and the alcohol may also be used by distilling off the alcohol depending on the case. Since there is the advantage of being able to reduce the size of the reaction vessels of the other steps, it is preferable to remove as much of the alcohol as possible. Removal by known distillation is preferable for the removal method, and known distillation equipment can be used for the distiller used for distillation. A thin film distillation apparatus is preferably used for the distillation apparatus since the alcohol can be removed in a short period of time. Differing from the alkyl tin alkoxide synthesis step, since dialkyl tin oxide normally in a solid state is not used in this step, there are few restrictions on the reaction vessel. Namely, there are no particular limitations on the type of reaction vessel of the dehydration reaction, and a known tank type or a column type reaction vessel can be used. A low boiling point reaction mixture containing water is extracted in gaseous form from the reaction vessel by distillation, while a high boiling point reaction mixture containing a produced alkyl tin alkoxide or alkyl tin alkoxide mixture is extracted in the form of a liquid from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a columnar reactor are preferable from the viewpoint of efficiently shifting the equilibrium to the products side, while a structure having a large gas-liquid contact area is preferable for being able to rapidly transfer the water formed to the gaseous phase. Continuous methods using a multitubular reactor, a multistage distillation column or a packed column packed with a packing are particularly preferable. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

The dialkyl tin compound produced in step (4) as described above is reused in the form of the dialkyl tin compound used in step (1) according to the next step (5) (recycling step) in which the organic tin compound having the tin-oxygen-carbon bond obtained in step (4) is reused as the organic tin compound having a tin-oxygen-carbon bond of step (1).

An amine compound represented by the following formula (13) is used for the amine compound used in the production process of the present embodiment:

(wherein $R^{14}$ represents a group selected from the group consisting of an aliphatic group having 1 to 20 carbon atoms and an aromatic group having 6 to 20 carbon atoms, the above group containing an atom selected from carbon and oxygen atoms, and having a valence equal to n, and n represents an integer of 1 to 10).

In formula (13) above, a polyamine compound in which n is 1 to 3 is used preferably, while a polyamine compound in which n is 2 is used more preferably.

Examples of such polyamine compounds may include aliphatic diamines such as hexamethylene diamine, 4,4'-methylenebis(cyclohexylamine) (including isomers), cyclohexane diamine (including isomers) or 3-aminomethyl-3,5,5-trimethylcyclohexyl amine (including isomers); and aromatic diamines such as phenylene diamine (including isomers), toluene diamine (including isomers) or 4,4'-methylene dianiline. Among these, aliphatic diamines such as hexamethylene diamine, 4,4'-methylenebis(cyclohexylamine) (including isomers), cyclohexane diamine (including isomers) and 3-aminomethyl-3,5,5-trimethylcyclohexyl amine (including isomers) are used preferably, while hexamethylene diamine, 4,4'-methylenebis(cyclohexylamine) and 3-aminomethyl-3,5,5-trimethylcyclohexyl amine are used more preferably.

The amine compound is preferably supplied in a liquid state to the reaction vessel in which production of carbamic acid ester is carried out. In general, the amine compound as exemplified above is frequently a solid at normal temperature (e.g., 20° C.), and in such cases, although the amine compound can be supplied in a liquid state by heating to a temperature equal to or higher than the melting point of the amine compound, if the amine compound is supplied at an excessively high temperature, since there are cases in which side-reactions such as thermal denaturation reactions caused by heating may occur, the amine compound is preferably supplied in a liquid state at a comparatively low temperature in the form of a mixture with an alcohol, water or carbonic acid ester.

Although varying according to the reacted compounds, the reaction conditions under which the reaction between the carbonic acid ester and amine compound is carried out are such that the stoichiometric ratio of the carbonic acid ester to the amino groups of the amine compound is within a range of from 1.1 to 1000 times, and although the carbonic acid ester is preferably in excess with respect to the amino groups of the amine compound in order to complete the reaction quickly by increasing the reaction rate, in consideration of the size of the reaction vessel, the stoichiometric ratio is preferably within a range of from 2 to 100 times and more preferably within a range of from 2.5 to 30 times. The reaction temperature is generally within a range of from normal temperature (e.g., 20° C.) to 200° C. Although a high temperature is preferable for increasing the reaction rate, on the other hand, since undesirable reactions also occur at high temperatures, the reaction temperature is preferably within a range of from 50 to 150° C. A known cooling apparatus or a heating apparatus may be installed in the reaction vessel to maintain a constant reaction temperature. In addition, although varying according to the types of compounds used and the reaction temperature, the reaction pressure may be decreased pressure, normal pressure or increased pressure, and the reaction is generally carried out within a range of from 20 to $1 \times 10^6$ Pa. There are no particular limitations on the reaction time (residence time in the case of a continuous process), and is generally from 0.001 to 50 hours, preferably from 0.01 to 10 hours and more preferably from 0.1 to 5 hours. In addition, the reaction can also be terminated by confirming that a desired amount of carbamic acid ester has been formed by, for example, liquid chromatography after sampling the reaction liquid. In the present embodiment, a catalyst can be used as necessary, and examples of catalysts that can be used may include organic metal compounds and inorganic metal compounds of tin, lead, copper or titanium, and basic catalysts such as alcoholates of alkaline metals or alkaline earth metals in the form of methylates, ethylates and butyrates (including isomers) of lithium, sodium, potassium, calcium or barium. Although it is not necessarily required to use a reaction solvent in the present embodiment, a suitable solvent is preferably used as a reaction solvent for the purpose of facilitating the reaction procedure, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; alcohols such as methanol, ethanol, propanol (including isomers), butanol (including isomers), pentanol (including isomers), hexanol (including isomers), heptanol (including isomers), octanol (including isomers) or nonanol (including isomers); aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aromatic hydroxy compounds such as phenol, methylphenol (including isomers), ethylphenol (including isomers), butylphenol (including isomers), pentylphenol (including isomers), dimethylphenol (including isomers), diethylphenol (including isomers), dibutylphenol (including isomers) or dipentylphenol (including isomers); aliphatic hydrocarbons such as cyclohexane, cyclopentane, cyclooctane or ethylcyclohexane; alicyclic alcohols such as cyclohexanol, cyclopentanol or cyclooctanol; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; and sulfoxides such as dimethylsulfoxide or diphenylsulfoxide. These solvents can be used alone or two or more types can be used as a mixture. In addition, carbonic acid ester used in excess with respect to amino groups of the amine compound is also preferably used as a solvent in the reaction.

There are no particular limitations on the reaction apparatus used when carrying out this reaction, and a known reaction vessel can be used. For example, conventionally known reaction vessels can be suitably combined, such as a stirring tank, a pressurized stirring tank, a depressurized stirring tank, a column type reaction vessel, a distillation column, a packed column or a thin film distiller. There are no particular limitations on the material of the reaction vessel, and known materials can be used, examples of which may include glass, stainless steel, carbon steel, Hastelloy, glass-lined base materials and Teflon (registered trademark) coated materials.

<Removal of Hydroxy Compound>

The reaction liquid containing carbamic acid ester produced by reacting with carbonic acid ester and amine compound as indicated above may be supplied directly to the reaction vessel in which thermal decomposition of carbamic acid ester is carried out (hereinafter referred to as "thermal decomposition reaction vessel"), or may be supplied to the thermal decomposition reaction vessel after having purified the carbamic acid ester from the reaction liquid. However, since isocyanate formed by thermal decomposition of the carbamic acid ester forms carbamic acid ester by reacting with a hydroxy compound (alcohol and/or aromatic hydroxy compound), in order to increase the reaction efficiency of the thermal decomposition reaction, it is preferable to remove the hydroxy compound (alcohol and/or aromatic hydroxy compound) from the reaction liquid in advance prior to carrying out the thermal decomposition reaction.

In the present embodiment, carbamic acid ester can be purified and supplied to the thermal decomposition reaction vessel by a known method such as a method in which a low boiling point component such as the reaction solvent is distilled from the reaction liquid by distillation in the case of using a hydroxy compound and/or carbonic acid ester and/or reaction solvent, a method in which the carbamic acid ester is cleaned by a solvent that is inert and has low solubility in carbamic acid ester, or a method involving purification by crystallization. Among these methods, a method in which a low boiling point component such as the reaction solvent is distilled off by distillation in the case of using a hydroxy compound and/or carbonic acid ester and/or reaction solvent is preferably carried out in consideration of the ease of the procedure and so forth.

A known distillation apparatus can be used for the apparatus for separating the hydroxy compound and carbonic acid ester from the reaction liquid by distillation. For example, methods using an apparatus such as a distillation column, a multistage distillation column, a multitubular reactor, a continuous multistage distillation column, a packed column, a thin film evaporator, a falling film evaporator or a falling drop evaporator, and methods using a combination thereof are used. Although varying according to the types of compounds contained in the reaction liquid, the conditions under which the distillative separation is carried out are such that the temperature is preferably within a range of from normal temperature (e.g., 20° C.) to 180° C., and since there are cases in which undesirable reactions occur at high temperatures, the temperature is preferably within a range of from 50 to 150° C. A known cooling apparatus or a heating apparatus may be installed in the reaction vessel to maintain a constant temperature. In addition, although varying according to the types of compounds contained in the reaction liquid and the temperature, the pressure may be decreased pressure, normal pressure or increased pressure, and distillative separation is normally carried out within a range of from 20 to $1 \times 10^6$ Pa. In the case of carrying out the procedure for a long period of time at high temperatures, particularly in the case of distillative separation, since carbamic acid ester contained in the reaction liquid may undergo thermal denaturation resulting in a decrease in the yield of the carbamic acid ester, distillative separation is carried out under a reduced pressure at a pressure that is as close as possible to the degree of depressurization able to be achieved by the distillation apparatus, and a temperature is preferably selected that is within an adequate temperature range for distilling off the compound desired to be removed from the reaction liquid in the gaseous phase, and is as low as possible within the temperature range that allows the carbamic acid ester, or a mixture containing the carbamic acid ester following distillative separation, to be present as a liquid. Although the primary objective of distillative separation is to separate hydroxy compound (alcohol and/or aromatic hydroxy compound) from the reaction liquid, in the case of using carbonic acid ester and reaction solvent contained in the reaction liquid, it is preferable to also separate the reaction solvent. If the subsequently described thermal decomposition reaction is carried out while carbonic acid ester and/or reaction solvent are still contained in the reaction liquid, a step is required for separating the formed isocyanate or hydroxy compound, thereby resulting in a complex procedure.

The hydroxy compound and/or carbonic acid ester separated and recovered in the reaction, and a solvent in the case the reaction liquid contains a solvent, are each preferably reused. The hydroxy compound is reused as a hydroxy compound (alcohol and/or aromatic hydroxy compound) in the carbonic acid ester production step, the carbonic acid ester is reused as carbonic acid ester in the production carbamic acid ester, and the solvent is reused as solvent in the production of carbamic acid ester.

In the case a catalyst is used in the production of carbamic acid ester and a catalyst or catalyst residue is contained in the reaction liquid, the catalyst contained in the reaction liquid or carbamic acid ester can be used directly as a catalyst for the thermal decomposition reaction, or the catalyst may be removed from the reaction liquid or carbamic acid ester. In the case of using a basic catalyst in particular, since reactions attributable to the catalyst may occur during the thermal decomposition reaction causing a decrease in yield, it is preferable in such cases to carry out the thermal decomposition reaction after first removing the catalyst. Known methods can be used to remove the catalyst. An example of a preferable method for removing the catalyst may involve neutralization by treating with an organic acid or inorganic acid in a homogeneous phase or heterogeneous phase. A mono- or dicarboxylic acid, alkyl or aryl sulfonate or phosphate, ion exchange resin or activated charcoal and the like are used to remove the catalyst. The catalyst is removed within a range of from normal temperature (e.g., 20° C.) to 180° C. since carbamic acid ester may solidify at low temperatures, while thermal denaturation may occur at high temperatures. Preferably, removal of catalyst is carried out in continuation after having carried out the step for producing carbamic acid ester while maintaining the temperature at a temperature at which the formed carbamic acid ester does not precipitate from the reaction liquid of the carbamic acid ester production step. In the case of separating solvent and/or hydroxy compound and/or carbonic acid ester from the reaction liquid of the carbamic acid ester production step, the previously described separation procedure is preferably carried out after having removed the catalyst from the reaction liquid.

<Transfer of Carbamic Acid Ester>

The reactant containing carbamic acid ester produced according to the reaction between carbonic acid ester and amine compound (hereinafter referred to as "reactant"), or a mixture containing carbamic acid ester in which hydroxy compound has been removed from the reaction liquid according to the method described above (hereinafter referred to as "residue liquid"), is supplied to a thermal decomposition reaction vessel.

Since carbamic acid esters easily form hydrogen bonds between molecules by ester groups constituting the carbamic acid ester, they frequency have a high melting point. In the transfer of carbamic acid esters having a high melting point, the carbamic acid ester is transferred after having converted to a vehicle by, for example, crushing or forming into pellets, or the carbamic acid ester is heated to a temperature higher than the melting point thereof and transferred in a liquid state. However, in the case of transferring solid carbamic acid ester that has been converted to a vehicle, there is a frequently the need for a complex apparatus to ensure stable transfer of a fixed amount of carbamic acid ester, or the need for a process for maintaining the form of the carbamic acid ester within a certain range in cases of the risk of clogging of the transfer line or frequent fluctuations in the form of the carbamic acid ester. Thus, the reactant or the residue liquid is preferably supplied to the thermal decomposition reaction vessel in liquid form.

In the case of transferring the reactant or the residue liquid in the liquid form, although it is preferable to heat to a high temperature in consideration of preventing solidification during transfer, if transferred at an excessively high temperature, since there are many case in which the carbamic acid ester contained in the reactant or the residue liquid undergoes thermal denaturation, the reactant or the residue liquid is preferably transferred within a temperature range of from 30 to 200° C., more preferably from 50 to 180° C. and even more preferably from 80 to 150° C.

<Carbamic Acid Ester Thermal Decomposition Reaction>

Next, an explanation is provided of the production of isocyanate by carrying out a thermal decomposition reaction on the carbamic acid ester.

The thermal decomposition reaction in the present embodiment is a reaction in which the corresponding isocyanate and hydroxy compound (alcohol or aromatic hydroxy compound) are formed from the carbamic acid ester.

The reaction temperature is generally within a range of from 100 to 350° C., and although a high temperature is preferable for increasing the reaction rate, since side reactions as described above may be conversely caused by the carbamic acid ester and/or the reaction product in the form of the isocyanate at high temperatures, the reaction temperature is preferably within a range of from 150 to 300° C. A known cooling apparatus or a heating apparatus may be installed in the reaction vessel to maintain a constant reaction temperature. In addition, although varying according to the types of compounds used and reaction temperature, the reaction pressure may be decreased pressure, normal pressure or increased pressure, and the reaction is generally carried out at a pressure within a range of from 20 to $1 \times 10^6$ Pa. There are no particular limitations on the reaction time (residence time in the case of a continuous method) and is generally from 0.001 to 100 hours, preferably from 0.005 to 50 hours and more preferably from 0.01 to 10 hours.

There are cases in which side reactions as described above may occur in cases of holding the carbamic acid ester at high temperatures for an extended period of time. In addition, isocyanates formed by the thermal decomposition reaction may also cause such side reactions. Thus, the time during which the carbamic acid ester and the isocyanate are held at a high temperature is preferably as short as possible, and the thermal decomposition reaction is preferably carried out by a continuous process. A continuous process refers to a process in which a mixture containing the carbamic acid ester is continuously supplied to a reaction vessel and subjected to the thermal decomposition reaction followed by continuously extracting the isocyanate and hydroxy compound formed from the thermal decomposition reaction vessel. In this continuous process, a low boiling point component formed by thermal decomposition of the carbamic acid ester is preferably recovered from the upper portion of the thermal decomposition reaction vessel in the form of a gaseous phase component, while the remainder is recovered from the bottom of the thermal decomposition reaction vessel in the form of a liquid phase component. Although all compounds present in the thermal decomposition reaction vessel can be recovered in the form of gaseous phase components, by allowing liquid phase components to remain in the thermal decomposition reaction vessel, polymeric compounds formed by side reactions caused by the carbamic acid ester and/or isocyanate are dissolved, thereby demonstrating the effect of preventing the polymeric compounds from adhering to and accumulating in the thermal decomposition reaction vessel. Although isocyanate and hydroxy compound are formed by thermal decomposition of carbamic acid ester, at least one of these compounds is recovered in the form of a gaseous phase component. Which of these compounds is recovered in the form of a gaseous phase component depends on the conditions of the thermal decomposition reaction.

Here, although the term "low boiling point component formed by thermal decomposition of carbamic acid ester" used in the present embodiment corresponds to the hydroxy compound and/or isocyanate formed by thermal decomposition of the carbamic acid ester, it particularly refers to compounds able to exist as a gas under the conditions under which the thermal decomposition reaction is carried out.

A method can be employed by which the isocyanate and hydroxy compound formed by the thermal decomposition reaction are recovered in the form of a gaseous phase component, while a liquid phase component is recovered containing the carbamic acid ester and/or carbonic acid ester. In this method, the isocyanate and hydroxy compound may be recovered separately in the thermal decomposition reaction vessel. The recovered gaseous phase component containing isocyanate is preferably supplied in the gaseous phase to a distillation apparatus for separation and purification of the isocyanate. On the other hand, the liquid phase component containing the carbamic acid ester and/or carbonic acid ester is recovered from the bottom of the thermal decomposition reaction vessel, all or a portion of the liquid phase component is supplied to the upper portion of the thermal decomposition reaction vessel, and the carbamic acid ester is again subjected to the thermal decomposition reaction. The upper portion of the thermal decomposition reaction vessel as referred to here refers to, for example, to the second plate and beyond from the bottom in terms of the number of theoretical plates in the case the thermal decomposition reaction vessel is a distillation column, or refers to the portion higher than the heated conductive surface in the case the thermal decomposition reaction vessel is a thin film distiller. When supplying all or a portion of the liquid phase component to the thermal decomposition reaction vessel, the liquid phase component is preferably transferred while holding at a temperature of from 50 to 180° C., more preferably from 70 to 170° C. and even more preferably from 100 to 150° C. In the case the liquid phase component contains carbonic acid ester, the liquid phase component may be supplied to the thermal decomposition reaction vessel after having separated and recovered the carbonic acid ester from the liquid phase component. The separated and recovered carbonic acid ester is preferably reused.

Although previously mentioned, in the thermal decomposition reaction, the liquid phase component is preferably recovered from the bottom of the thermal decomposition reaction vessel. This is because, as a result of having the liquid phase component present in the thermal decomposition reaction vessel, polymeric by-products formed by side reactions caused by carbamic acid ester and/or isocyanate are dissolved and are able to be discharged from the thermal decomposition reaction vessel in the form of a liquid phase component, thereby having the effect of reducing adhesion and accumulation of these polymeric compounds in the thermal decomposition reaction vessel.

Although all or a portion of the liquid phase component is supplied to the upper portion of the thermal decomposition reaction vessel and the carbamic acid ester is re-subjected to the thermal decomposition reaction, there are cases in which polymeric by-products accumulate in the liquid phase component if this step is repeated. In such cases, all or a portion of the liquid phase component can be removed from the reaction system to reduce the accumulation of polymeric by-products or maintain at a constant concentration.

The hydroxy compound and/or carbonic acid ester contained in the gaseous phase component and/or liquid phase component obtained in the thermal decomposition reaction as described above can each be separated and recovered for reuse. More specifically, the hydroxy compound can be reused as the hydroxy compound of step (3) for production of carbonic acid ester, and the carbonic acid ester can be reused as a raw material for the production of carbamic acid ester.

Although there are no particular limitations on the type of thermal decomposition reaction vessel, a known distillation apparatus is used preferably to efficiently recover the gaseous phase component. Various known methods are used, examples of which may include a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator and types using combinations thereof. From the viewpoint of rapidly removing low boiling point components from the reaction system, a tubular reactor is preferable, while a reaction vessel such as a tubular thin film evaporator, a tubular falling film evaporator is used more preferably, and structures having a large gas-liquid contact area are preferable for being able to rapidly transfer low boiling point components formed to the gaseous phase.

Although known materials may be used for the thermal decomposition reaction vessel and lines provided they do not have a detrimental effect on the carbamic acid ester or products in the form of the hydroxy compound, isocyanate and the like, SUS304, SUS316 or SUS316L and the like can be used preferably since they are inexpensive.

<Cleaning the Thermal Decomposition Reaction Vessel>

In the present embodiment, although polymeric by-products originating from side reactions as represented by the previously indicated formulas (2), (3) and (4) are formed accompanying thermal decomposition of carbamic acid ester, there are cases in which these thermal decomposition reaction by-products may adhere to the thermal decomposition reaction vessel when operating for an extended period of time even in case of carrying out the thermal decomposition reaction according to the method described above. If these compounds adhering to the thermal decomposition reaction vessel accumulate to a certain degree, operation of the thermal decomposition reaction vessel becomes impaired, and since there are frequently cases in which this makes long-term operation difficult, it was necessary to perform work consisting of disassembling and cleaning the thermal decomposition reaction vessel.

The inventors of the present invention unexpectedly found that compounds adhered to the thermal decomposition reaction vessel easily dissolve in acids. On the basis of these findings, in the case high boiling point substances have become adhered to the thermal decomposition reaction vessel, the inventors of the present invention conceived and perfected a method for keeping the inside of the thermal decomposition reaction vessel (and particularly the walls thereof) clean by cleaning the walls of the thermal decomposition reaction vessel with the acids to dissolve these high boiling point substances and remove them from the thermal decomposition reaction vessel. Since this method enables the walls of the thermal decomposition reaction vessel to be cleaned without having to disassemble and separately clean the thermal decomposition reaction vessel, the down time of the thermal decomposition reaction vessel can be shortened considerably, thereby resulting in high isocyanate production efficiency.

There are no particular limitations on the acids used for cleaning provided it is able to dissolve the polymeric by-products, and organic acids or inorganic acids may be used, although organic acids are used preferably. Although examples of organic acids used may include carbonic acid, sulfonic acid, sulfinic acid, phenols, enols, thiophenols, imides, oximes and aromatic sulfonamides, carbonic acid and phenols are used preferably. Examples of such compounds may include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (including isomers), octanoic acid (including isomers), nonanoic acid (including isomers), decanoic acid (including isomers), undecanoic acid (including isomers), dodecanoic acid (including isomers), tetradecanoic acid (including isomers), hexadecanoic acid (including isomers), acrylic acid, crotonic acid, isocrotonic acid, vinyl acetate, methacrylic acid, angelic acid, tiglic acid, allyl acetate or undecenoic acid (including isomers); saturated or unsaturated aliphatic dicarboxylic acids such as oxalic acid, malonic acid, succinic acid, glutaric acid, adipic acid, heptanedioic acid (including isomers), octanedioic acid (including isomers), nonanedioic acid (including isomers), decanedioic acid (including isomers), maleic acid, fumaric acid, methylmaleic acid, methylfumaric acid, pentenedioic acid (including isomers), itaconic acid or allylmalonic acid; saturated or unsaturated aliphatic tricarboxylic acid compounds such as 1,2,3-propanetricarboxylic acid, 1,2,3-propenetricarboxylic acid or 2,3-dimethylbutane-1,2,3-tricarboxylic acid; aromatic monocarboxylic acid compounds such as benzoic acid, methylbenzoic acid (including isomers), ethylbenzoic acid (including isomers), propylbenzoic acid (including isomers), dimethylbenzoic acid (including isomers) or trimethylbenzoic acid (including isomers); aromatic dicarboxylic acid compounds such as phthalic acid, isophthalic acid, terephthalic acid or methylisophthalic acid (including isomers); aromatic tricarboxylic acid compounds such as hemimellitic acid, trimellitic acid or trimesinic acid; mono-substituted phenols such as phenol, methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers) or cumylphenol (including isomers); di-substituted phenols such as dimethylphenol (including isomers), diethylphenol (including isomers), dipropylphenol (including isomers), dibutylphenol (including isomers), dipentylphenol (including isomers), dihexylphenol (including isomers), diheptylphenol (including isomers), dioctylphenol (including isomers), dinonylphenol (including isomers), didecylphenol (including isomers), didodecylphenol (including isomers), diphenylphenol (including isomers), diphenoxyphenol (including isomers), dicumylphenol (including isomers), methylethylphenol (including isomers), methylpropylphenol (including isomers), methylbutylphenol (including isomers), methylpentylphenol (including isomers), methylhexylphenol (including isomers), methylheptylphenol (including isomers), methyloctylphenol (including isomers), methylnonylphenol (including isomers), methyldecylphenol (including isomers), methyldodecylphenol (including isomers), methylphenylphenol (including isomers), methylphenoxyphenol (including isomers), methylcumylphenol (including isomers), ethylpropylphenol (including isomers), ethylbutylphenol (including isomers), ethylpentylphenol (including isomers), ethylhexylphenol (including isomers), ethylheptylphenol (including isomers), ethyloctylphenol (including isomers), ethylnonylphenol (including isomers), ethyldecylphenol (including isomers), ethyldodecylphenol (including isomers), ethylphenylphenol (including isomers), ethylphenoxyphenol (including isomers), ethylcumylphenol (including isomers), propylbutylphenol (including isomers), propylpentylphenol (including isomers), propylhexylphenol (including isomers), propylheptylphenol (including isomers), propyloctylphenol (including isomers), propylnonylphenol (including isomers), propyldecylphenol (including isomers), propyldodecylphenol (including isomers), propylphenylphenol (including isomers), propylphenoxyphenol (including isomers), propylcumylphenol (including isomers), butylpentylphenol (including isomers), butylhexylphenol (including isomers), butylheptylphenol (including isomers), butyloctylphenol (including isomers), butylnonylphenol (including isomers), butyldecylphenol (including isomers), butyldodecylphenol (including isomers), butylphenylphenol (including isomers), butylphenoxyphenol (including isomers), butylcumylphenol (including isomers), pentylhexylphenol (including isomers), pentylheptylphenol (including isomers), pentyloctylphenol (including isomers), pentylnonylphenol (including isomers), pentyldecylphenol (including isomers), pentyldodecylphenol (including isomers), pentylphenylphenol (including isomers), pentylphenoxyphenol (including isomers), pentylcumylphenol (including isomers), hexylheptylphenol (including isomers), hexyloctylphenol (including isomers), hexylnonylphenol (including isomers), hexyldecylphenol (including isomers), hexyldodecylphenol (including isomers), hexylphenylphenol (including isomers), hexylphenoxyphenol (including isomers), hexylcumylphenol (including isomers), heptyloctylphenol (including isomers), heptylnonylphenol (including isomers), heptyldecylphenol (including isomers), heptyldodecylphenol (including isomers), heptylphenylphenol (including isomers), heptylphenoxyphenol (including isomers), heptylcumylphenol (including isomers), octylnonylphenol (including isomers), octyldecylphenol (including isomers), octyldodecylphenol (including isomers), octylphenylphenol (including isomers), octylphenoxyphenol (including isomers), octylcumylphenol (including isomers), nonyldecylphenol (including isomers), nonyldodecylphenol (including isomers), nonylphenylphenol (including isomers), nonylphenoxyphenol (including isomers), nonylcumylphenol (including isomers), dodecylphenylphenol (including isomers), dodecylphenoxyphenol (including isomers) or dodecylcumylphenol (including isomers); and, tri-substituted phenols such as trimethylphenol (including isomers), triethylphenol (including isomers), tripropylphenol (including isomers), tributylphenol (including isomers), tripentylphenol (including isomers), trihexylphenol (including isomers), triheptylphenol (including isomers), trioctylphenol (including isomers), trinonylphenol (including isomers), tridecylphenol (including isomers), tridodecylphenol (including isomers), triphenylphenol (including isomers), triphenoxyphenol (including isomers), tricumylphenol (including isomers), dimethylethylphenol (including isomers), dimethylpropylphenol (including isomers), dimethylbutylphenol (including isomers), dimethylpentylphenol (including isomers), dimethylhexylphenol (including isomers), dimethylheptylphenol (including isomers), dimethyloctylphenol (including isomers), dimethylnonylphenol (including isomers), dimethyldecylphenol (including isomers), dimethyldodecylphenol (including isomers), dimethylphenylphenol (including isomers), dimethylphenoxyphenol (including isomers), dimethylcumylphenol (including isomers), diethylmethylphenol (including isomers), diethylpropylphenol (including isomers), diethylbutylphenol (including isomers), diethylpentylphenol (including isomers), diethylhexylphenol (including isomers), diethylheptylphenol (including isomers), diethyloctylphenol (including isomers), diethylnonylphenol (including isomers), diethyldecylphenol (including isomers), diethyldodecylphenol (including isomers), diethylphenylphenol (including isomers), diethylphenoxyphenol (including isomers), diethylcumylphenol (including isomers), dipropylmethylphenol (including isomers), dipropylethylphenol (including isomers), dipropylbutylphenol (including isomers), dipropylpentylphenol (including isomers), dipropylhexylphenol (including isomers), dipropylheptylphenol (including isomers), dipropyloctylphenol (including isomers), dipropylnonylphenol (including isomers), dipropyldecylphenol (including isomers), dipropyldodecylphenol (including isomers), dipropylphenylphenol (including isomers), dipropylphenoxyphenol (including isomers), dipropylcumylphenol (including isomers), dibutylmethylphenol (including isomers), dibutylethylphenol (including isomers), dibutylpropylphenol (including isomers), dibutylpentylphenol (including isomers), dibutylhexylphenol (including isomers), dibutylheptylphenol (including isomers), dibutyloctylphenol (including isomers), dibutylnonylphenol (including isomers), dibutyldecylphenol (including isomers), dibutyldodecylphenol (including isomers), dibutylphenylphenol (including isomers), dibutylphenoxyphenol (including isomers), dibutylcumylphenol (including isomers), dipentylmethylphenol (including isomers), dipentylethylphenol (including isomers), dipentylpropylphenol (including isomers), dipentylbutylphenol (including isomers), dipentylhexylphenol (including isomers), dipentylheptylphenol (including isomers), dipentyloctylphenol (including isomers), dipentylnonylphenol (including isomers), dipentyldecylphenol (including isomers), dipentyldodecylphenol (including isomers), dipentylphenylphenol (including isomers), dipentylphenoxyphenol (including isomers), dipentylcumylphenol (including isomers), dihexylmethylphenol (including isomers), dihexylethylphenol (including isomers), dihexylpropylphenol (including isomers), dihexylbutylphenol (including isomers), dihexylpentylphenol (including isomers), dihexylheptylphenol (including isomers), dihexyloctylphenol (including isomers), dihexylnonylphenol (including isomers), dihexyldecylphenol (including isomers), dihexyldodecylphenol (including isomers), dihexylphenylphenol (including isomers), dihexylphenoxyphenol (including isomers), dihexylcumylphenol (including isomers), diheptylmethylphenol (including isomers), diheptylethylphenol (including isomers), diheptylpropylphenol (including isomers), diheptylbutylphenol (including isomers), diheptylpentylphenol (including isomers), diheptylhexylphenol (including isomers), diheptyloctylphenol (including isomers), diheptylnonylphenol (including isomers), diheptyldecylphenol (including isomers), diheptyldodecylphenol (including isomers), diheptylphenylphenol (including isomers), diheptylphenoxyphenol (including isomers), diheptylcumylphenol (including isomers), dioctylmethylphenol (including isomers), dioctylethylphenol (including isomers), dioctylpropylphenol (including isomers), dioctylbutylphenol (including isomers), dioctylpentylphenol (including isomers), dioctylhexylphenol (including isomers), dioctylheptylphenol (including isomers), dioctylnonylphenol (including isomers), dioctyldecylphenol (including isomers), dioctyldodecylphenol (including isomers), dioctylphenylphenol (including isomers), dioctylphenoxyphenol (including isomers), dioctylcumylphenol (including isomers), dinonylmethylphenol (including isomers), dinonylethylphenol (including isomers), dinonylpropylphenol (including isomers), dinonylbutylphenol (including isomers), dinonylpentylphenol (including isomers), dinonylhexylphenol (including isomers), dinonylheptylphenol (including isomers), dinonyloctylphenol (including isomers), dinonyldecylphenol (including isomers), dinonyldodecylphenol (including isomers), dinonylphenylphenol (including isomers), dinonylphenoxyphenol (including isomers), dinonylcumylphenol (including isomers), didecylmethylphenol (including isomers), didecylethylphenol (including isomers), didecylpropylphenol (including isomers), didecylbutylphenol (including isomers), didecylpentylphenol (including isomers), didecylhexylphenol (including isomers), didecylheptylphenol (including isomers), didecyloctylphenol (including isomers), didecylnonylphenol (including isomers), didecyldodecylphenol (including isomers), didecylphenylphenol (including isomers), didecylphenoxyphenol (including isomers), didecylcumylphenol (including isomers), didodecylmethylphenol (including isomers), didodecylethylphenol (including isomers), didodecylpropylphenol (including isomers), didodecylbutylphenol (including isomers), didodecylpentylphenol (including isomers), didodecylhexylphenol (including isomers), didodecylheptylphenol (including isomers), didodecyloctylphenol (including isomers), didodecylnonylphenol (including isomers), didodecyldecylphenol (including isomers), didodecyldodecylphenol (including isomers), didodecylphenylphenol (including isomers), didodecylphenoxyphenol (including isomers), didodecylcumylphenol (including isomers), diphenylmethylphenol (including isomers), diphenylethylphenol (including isomers), diphenylpropylphenol (including isomers), diphenylbutylphenol (including isomers), diphenylpentylphenol (including isomers), diphenylhexylphenol (including isomers), diphenylheptylphenol (including isomers), diphenyloctylphenol (including isomers), diphenylnonylphenol (including isomers), diphenyldecylphenol (including isomers), diphenyldodecylphenol (including isomers), diphenylphenoxyphenol (including isomers), diphenylcumylphenol (including isomers), diphenoxymethylphenol (including isomers), diphenoxyethylphenol (including isomers), diphenoxypropylphenol (including isomers), diphenoxybutylphenol (including isomers), diphenoxypentylphenol (including isomers), diphenoxyhexylphenol (including isomers), diphenoxyheptylphenol (including isomers), diphenoxyoctylphenol (including isomers), diphenoxynonylphenol (including isomers), diphenoxydecylphenol (including isomers), diphenoxydodecylphenol (including isomers), diphenoxyphenylphenol (including isomers), diphenoxycumylphenol (including isomers), dicumylmethylphenol (including isomers), dicumylethylphenol (including isomers), dicumylpropylphenol (including isomers), dicumylbutylphenol (including isomers), dicumylpentylphenol (including isomers), dicumylhexylphenol (including isomers), dicumylheptylphenol (including isomers), dicumyloctylphenol (including isomers), dicumylnonylphenol (including isomers), dicumyldecylphenol (including isomers), dicumyldodecylphenol (including isomers), dicumylphenylphenol (including isomers), dicumylphenoxyphenol (including isomers), methylethylpropylphenol (including isomers), methylethylbutylphenol (including isomers), methylethylpentylphenol (including isomers), methylethylhexylphenol (including isomers), methylethylheptylphenol (including isomers), methylethyloctylphenol (including isomers), methylethylnonylphenol (including isomers), methylethyldecylphenol (including isomers), methylethyldodecylphenol (including isomers), methylethylphenylphenol (including isomers), methylethylphenoxyphenol (including isomers), methylethylcumylphenol (including isomers), methylpropylbutylphenol (including isomers), methylpropylpentylphenol (including isomers), methylpropylhexylphenol (including isomers), methylpropylheptylphenol (including isomers), methylpropyloctylphenol (including isomers), methylpropylnonylphenol (including isomers), methylpropyldecylphenol (including isomers), methylpropyldodecylphenol (including isomers), methylpropylphenylphenol (including isomers), methylpropylphenoxyphenol (including isomers), methylpropylcumylphenol (including isomers), methylbutylpentylphenol (including isomers), methylbutylhexylphenol (including isomers), methylbutylheptylphenol (including isomers), methylbutyloctylphenol (including isomers), methylbutylnonylphenol (including isomers), methylbutyldecylphenol (including isomers), methylbutyldodecylphenol (including isomers), methylbutylphenylphenol (including isomers), methylbutylphenoxyphenol (including isomers), methylbutylcumylphenol (including isomers), methylpentylhexylphenol (including isomers), methylpentylheptylphenol (including isomers), methylpentyloctylphenol (including isomers), methylpentylnonylphenol (including isomers), methylpentyldecylphenol (including isomers), methylpentyldodecylphenol (including isomers), methylpentylphenylphenol (including isomers), methylpentylphenoxyphenol (including isomers), methylpentylcumylphenol (including isomers), methylhexylheptylphenol (including isomers), methylhexyloctylphenol (including isomers), methylhexylnonylphenol (including isomers), methylhexyldecylphenol (including isomers), methylhexyldodecylphenol (including isomers), methylhexylphenylphenol (including isomers), methylhexylphenoxyphenol (including isomers), methylhexylcumylphenol (including isomers), ethylpropylbutylphenol (including isomers), ethylpropylpentylphenol (including isomers), ethylpropylhexylphenol (including isomers), ethylpropylheptylphenol (including isomers), ethylpropyloctylphenol (including isomers), ethylpropylnonylphenol (including isomers), ethylpropyldecylphenol (including isomers), ethylpropyldodecylphenol (including isomers), ethylpropylphenylphenol (including isomers), ethylpropylphenoxyphenol (including isomers), ethylpropylcumylphenol (including isomers), ethylbutylhexylphenol (including isomers), ethylbutylpentylphenol (including isomers), ethylbutylhexylphenol (including isomers), ethylbutylheptylphenol (including isomers), ethylbutyloctylphenol (including isomers), ethylbutylnonylphenol (including isomers), ethylbutyldecylphenol (including isomers), ethylbutyldodecylphenol (including isomers), ethylbutylphenylphenol (including isomers), ethylbutylphenoxyphenol (including isomers), ethylbutylcumylphenol (including isomers), ethylpentylhexylphenol (including isomers), ethylpentylheptylphenol (including isomers), ethylpentyloctylphenol (including isomers), ethylpentylnonylphenol (including isomers), ethylpentyldecylphenol (including isomers), ethylpentyldodecylphenol (including isomers), ethylpentylphenylphenol (including isomers), ethylpentylphenoxyphenol (including isomers), ethylpentylcumylphenol (including isomers), ethylhexylheptylphenol (including isomers), ethylhexyloctylphenol (including isomers), ethylhexylnonylphenol (including isomers), ethylhexyldecylphenol (including isomers), ethylhexyldodecylphenol (including isomers), ethylhexylphenylphenol (including isomers), ethylhexylphenoxyphenol (including isomers), ethylhexylcumylphenol (including isomers), ethylheptyloctylphenol (including isomers), ethylheptylnonylphenol (including isomers), ethylheptyldecylphenol (including isomers), ethylheptyldodecylphenol (including isomers), ethylheptylphenylphenol (including isomers), ethylheptylphenoxyphenol (including isomers), ethylheptylcumylphenol (including isomers), ethyloctylphenol (including isomers), ethyloctylnonylphenol (including isomers), ethylocyldecylphenol (including isomers), ethyloctyldodecylphenol (including isomers), ethyloctylphenylphenol (including isomers), ethyloctylphenoxyphenol (including isomers), ethyloctylcumylphenol (including isomers), ethylnonyldecylphenol (including isomers), ethylnonyldodecylphenol (including isomers), ethylnonylphenylphenol (including isomers), ethylnonylphenoxyphenol (including isomers), ethylnonylcumylphenol (including isomers), ethyldecyldodecylphenol (including isomers), ethyldecylphenylphenol (including isomers), ethyldecylphenoxyphenol (including isomers), ethyldecylcumylphenol (including isomers), ethyldodecylphenylphenol (including isomers), ethyldodecylphenoxyphenol (including isomers), ethyldodecylcumylphenol (including isomers), ethylphenylphenoxyphenol (including isomers), ethylphenylcumylphenol (including isomers), propylbutylphenol (including isomers), propylbutylpentylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpentylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propylhexylphenol (including isomers), propylhexylheptylphenol (including isomers), propylhexyloctylphenol (including isomers), propylhexylnonylphenol (including isomers), propylhexyldecylphenol (including isomers), propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptyldecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), porpyloctylphenoxyphenol (including isomers), propyloctylcumylphenol, (including isomers), propylnonyldecylphenol (including isomers), propylnonyldodecylphenol (including isomers), propylnonylphenylphenol (including isomers), propylnonylphenoxylphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propyldodecylphenoxyphenol (including isomers), propyldodecylcumylphenol (including isomers), methylphenol (including isomers), ethylphenol (including isomers), propylphenol (including isomers), butylphenol (including isomers), entylphenol (including isomers), hexylpohenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers), cumylphenol (including isomers), propylphenylphenoxyphenol (including isomers), propylphenylcumylphenol (including isomers), propylphenoxycumylphenol (including isomers), propylbutylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpenylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propylhexylheptylphenol (including isomers), propylhexyloctylphenol (including isomers), propylhexylnonylphenol (including isomers), propylhexyldecylphenol (including (including propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptydecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), propoyloctylphenoxyphenol (including isomers), propyloctylcumylphenol (including isomers), propylnonyldecylphenol (including isomers), propylnonyldodecylphenol (including isomers), propylnonylphenylphenol (including isomers), propylnonylphenoxyphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propoyldodecylphenoxyphenol (including isomers), cumylphenol (including isomers), propylphenylphenoxyphenol (including isomers), propylphenylcumylphenol (including isomers), butylpentylhexylphenol (including isomers), butylpoentylheptylphenol (including isomers), butylpentyloctylphenol (including isomers), butylpentylnonylphenol (including isomers), butylpentyldecylphenol (including isomers), butylpentyldodecylphenol (including isomers), butylpentylphenylphenol (including isomers), butylpentylphenoxyphenol (including isomers), butylpentylcumylphenol (including isomers), butylhexylheptyphenol (including isomers), butylhexyloctylphenol (including isomers), butylhexylnonylphenol (including isomers), butylhexyldecylphenol (including isomers), butylhexyldodecylphenol (including isomers), butylhexylphenylphenol (including isomers), butylhexylphenoxyphenol (including isomers), butylhexylcumylphenol (including isomers), butylheptyloctylphenol (including isomers), butylheptylnonylphenol (including isomers), butylheptyldecylphenol (including isomers), butylheptyldodecylphenol (including isomers), butylheptylphenylphenol (including isomers), butylheptylphenoxyphenol (including isomers), butylheptylcumylphenol (including isomers), butyloctylnonylphenol (including isomers), butyloctyldecylphenol (including isomers), butyloctyldodecylphenol (including isomers), butyloctylphenylphenol (including isomers), butyloctylphenoxyphenol (including isomers), butyloctylcumylphenol (including isomers), butylnonyldecylphenol (including isomers), butylnonyldodecylphenol (including isomers), butylnonylphenylphenol (including isomers), butylnonylphenoxyphenol (including isomers), butylnonylcumylphenol (including isomers), butyldecyldodecylphenol (including isomers), butyldecylphenylphenol (including isomers), butyldecylphenoxyphenol (including isomers), butyldecylcumylphenol (including isomers), butyldodecylphenol (including isomers), butyldodecylphenylphenol (including isomers), butyldodecylphenoxyphenol (including isomers), butyldodecylcumylphenol (including isomers), butylphenylphenol (including isomers), butylphenylphenoxyphenol (including isomers), butylphenylcumylphenol (including isomers), pentylhexylheptylphenol (including isomers), pentylhexyloctylphenol (including isomers), pentylhexylnonylphenol (including isomers), pentylhexyldecylphenol (including isomers), pentylhexyldodecylphenol (including isomers), pentylhexylphenylphenol (including isomers), pentylhexylphenoxyphenol (including isomers), pentylhexylcumylphenol (including isomers), pentylhetpyloctylphenol (including isomers), pentylheptylnonylphenol (including isomers), pentylheptyldecylphenol (including isomers), pentylheptylodecylphenol (including isomers), pentylheptylphenylphenol (including isomers), pentylheptylphenoxyphenol (including isomers), pentylheptylcumylphenol (including isomers), pentyloctylnonylphenol (including isomers), pentyloctyldecylphenol (including isomers), pentyloctyldodecylphenol (including isomers), pentyloctylphenylphenol (including isomers), pentyloctylphenoxyphenol (including isomers), pentyloctylcumylphenol (including isomers), pentylnonyldecylphenol (including isomers), pentylnonyldodecylphenol (including isomers), pentylnonylphenylphenol (including isomers), pentylnonylphenoxyphenol (including isomers), pentylnonylcumylphenol (including isomers), pentyldecyldodecylphenol (including isomers), pentyldecylphenylphenol (including isomers), pentyldecylphenoxyphenol (including isomers), pentyldecylcumylphenol (including isomers), pentyldodecylphenylphenol (including isomers), pentyldodecylphenoxyphenol (including isomers), pentyldodecylcumylphenol (including isomers), pentylphenylphenoxyphenol (including isomers), pentylphenylcumylphenol (including isomers), hexylheptyloctylphenol (including isomers), hexylheptylnonylphenol (including isomers), hexylheptyldecylphenol (including isomers), hexylheptyldodecylphenol (including isomers), hexylheptylphenylphenol, (including isomers), hexylheptylphenoxyphenol (including isomers), hexylheptylcumylphenol (including isomers), hexyloctylnonylphenol (including isomers), hexyloctyldecylphenol (including isomers), hexyloctyldodecylphenol (including isomers), hexyloctylphenylphenol (including isomers), hexyloctylphenoxyphenol (including isomers), hexyloctylcumylphenol (including isomers), hexylnonyldecylphenol (including isomers), hexylnonyldodecylphenol (including isomers), hexylnonylphenylphenol (including isomers), hexylnonylphenoxyphenol (including isomers), hexylnonylcumylphenol (including isomers), hexyldecyldodecylphenol (including isomers), hexyldecylphenylphenol (including isomers), hexyldecylphenoxyphenol (including isomers), hexyldecylcumylphenol (including isomers), hexyldodecylphenylphenol (including isomers), hexyldodecylphenoxyphenol (including isomers), hexyldodecylcumylphenol (including isomers), hexylphenylphenoxyphenol (including isomers), hexylphenylcumylphenol (including isomers), heptyloctylnonylphenol (including isomers), heptyloctyldecylphenol (including isomers), heptyloctyldodecylphenol (including isomers), heptyloctylphenylphenol (including isomers), heptyloctylphenoxyphenol (including isomers), heptyloctylcumylphenol (including isomers), heptylnonyldecylphenol (including isomers), heptylnonyldodecylphenol (including isomers), heptylnonylphenylphenol (including isomers), heptylnonylphenoxyphenol (including isomers), heptylnonylcumylphenol (including isomers), heptyldecyldodecylphenol (including isomers), heptyldecylphenylphenol (including isomers), heptyldecylphenoxyphenol (including isomers), heptyldecylcumylphenol (including isomers), heptyldodecylphenylphenol (including isomers), heptyldodecylphenoxyphenol (including isomers), heptyldodecylcumylphenol (including isomers), heptylphenylphenoxyphenol (including isomers), heptylphenylcumylphenol (including isomers), octylnonyldecylphenol (including isomers), octylnonyldodecylphenol (including isomers), octylnonylphenylphenol (including isomers), octylnonylphenoxyphenol (including isomers), octylnonylcumylphenol (including isomers), octyldecyldodecylphenol (including isomers), octyldecylphenylphenol (including isomers), octyldecylphenoxyphenol (including isomers), octyldecylcumylphenol (including isomers), octyldodecylphenylphenol (including isomers), octyldodecylphenoxyphenol (including isomers), octyldodecylcumylphenol (including isomers), octylphenylphenoxyphenol (including isomers), octylphenylcumylphenol (including isomers), nonyldecyldodecylphenol (including isomers), nonyldecylphenylphenol (including isomers), nonyldecylphenoxyphenol (including isomers), nonyldecylcumylphenol (including isomers), nonyldodecylphenylphenol (including isomers), nonyldodecylphenoxyphenol (including isomers), nonyldodecylcumylphenol (including isomers), nonylphenylphenoxyphenol (including isomers), nonylphenylcumylphenol (including isomers), decyldodecylphenylphenol (including isomers), decyldodecylphenoxyphenol (including isomers), decyldodecylcumylphenol (including isomers), decylphenylphenoxyphenol (including isomers), decylphenylcumylphenol (including isomers), dodecylphenylphenoxyphenol (including isomers), dodecylphenylcumylphenol (including isomers) or phenylphenoxycumylphenol (including isomers). Among these organic acids, in consideration of separation of isocyanate formed in the thermal decomposition reaction in the case of organic acid remaining in the thermal decomposition reaction vessel, an organic acid is preferably selected for which the difference between the boiling point thereof and the standard boiling point of the isocyanate is 10° C. or more.

Various methods can be used to clean the thermal decomposition reaction vessel using the above cleaning solvent, examples of which may include cleaning the thermal decomposition reaction vessel by introducing the cleaning solvent from the upper portion of the thermal decomposition reaction vessel, and cleaning the inside of the thermal decomposition reaction vessel by introducing the cleaning solvent from the bottom of the thermal decomposition reaction vessel and boiling it inside the thermal decomposition reaction vessel.

It is not necessary to carry out the cleaning procedure each time the thermal decomposition reaction is carried out, but rather the cleaning frequency can be arbitrarily determined according to the compounds used, operating rate and so forth, and the cleaning procedure is preferably carried out once every 1 to 20000 hours of operation, more preferably once per one day to one year of operating time, and even more preferably once per one month to one year of operating time. The thermal decomposition reaction vessel may be provided with a line for introducing the cleaning solvent.

In addition, when carrying out thermal decomposition of carbamic acid ester for the purpose of cleaning the thermal decomposition reaction vessel, the cleaning solvent can also be present in the conditions of the thermal decomposition reaction. This differs from the inert solvent as referred to in the prior art (see, for example, U.S. Pat. No. 4,081,472). For example, according to this patent document, although an inert solvent refers to a compound that does not react with isocyanate formed by thermal decomposition of carbamic acid ester, in contrast thereto, as stated in the literature (Journal of the American Chemical Society, Vol. 64, p. 2229, 1942), for example, that urethane is formed by a reaction between an aromatic hydroxy compound and phenyl isocyanate, aromatic hydroxy compounds are able to react with isocyanates. The aromatic hydroxy compound may be supplied to the thermal decomposition reaction vessel after mixing with a reaction mixture or a distillation residue when transferring the reaction mixture obtained by reaction of carbonic acid ester and amine compound, or the distillation residue in which hydroxy compound and/or carbonic acid ester and/or reaction solvent has been separated from the reaction mixture, to the thermal decomposition reaction vessel, or the aromatic hydroxy compound may be supplied by providing a line for supplying the aromatic hydroxy compound separate from the line for supplying the reaction mixture.

Isocyanates obtained by the production process of the present embodiment can be preferably used as production raw materials of polyurethane foam, paints, adhesives and the like. In addition, since isocyanates can be produced according to the production process of the present embodiment in good yield without using toxic phosgene, the present invention is industrially extremely important.

EXAMPLES

Although the following provides a detailed explanation of the present invention based on examples thereof, the scope of the present invention is not limited by these examples.

<Analytical Methods>
1) NMR Analysis
   Apparatus: JNM-A400 FT-NMR system, JEOL Ltd., Japan
(1) Preparation of $^1$H- and $^{13}$C-NMR Analysis Samples
   About 0.3 g of sample solution were weighed followed by the addition of about 0.7 g of heavy chloroform (99.8%, Aldrich Corp., USA) and about 0.05 g of internal standard in the form of tetramethyl tin (guaranteed reagent, Wako Pure Chemical Industries, Ltd., Japan) and mixing to uniformity to obtain solutions used as NMR analysis samples.
(2) Quantitative Analysis
   Analyses were performed for each standard and quantitative analyses were performed on the analysis sample solutions based on the resulting calibration curve.
2) Liquid Chromatography
   Apparatus: LC-10AT system, Shimadzu Corp., Japan
   Column: Silica-60 column, Tosoh Corp., Japan, two columns connected in series
   Developing solvent: Mixed liquid of hexane/tetrahydrofuran (80/20) (v/v)
   Solvent flow rate: 2 mL/min
   Column temperature: 35° C.
   Detector: R.I. (refractometer)
(1) Liquid Chromatography Analysis Samples
   About 0.1 g of sample were weighed followed by the addition of about 1 g of tetrahydrofuran (dehydrated, Wako Pure Chemical Industries, Ltd., Japan) and about 0.02 g of internal standard in the form of bisphenol A (guaranteed reagent, Wako Pure Chemical Industries, Ltd., Japan) and mixing to uniformity to obtain solutions used as liquid chromatography analysis samples.
(2) Quantitative Analysis
   Analyses were performed for each standard and quantitative analyses were performed on the analysis sample solutions based on the resulting calibration curve.
3) Gas Chromatography
   Apparatus: GC-2010, Shimadzu Corp., Japan
   Column: DB-1 column, Agilent Technologies Corp., USA, length: 30 m, inner diameter: 0.250 mm, film thickness: 1.00 μm
   Column temperature: Held at 50° C. for 5 minutes followed by increasing at the rate of 10° C./min to 200° C.; held at 200° C. for 5 minutes followed by increasing at the rate of 10° C./min to 300° C.
   Detector: FID
(1) Gas Chromatography Analysis Samples
   About 0.05 g of sample were weighed followed by the addition of about 1 g of acetone (dehydrated, Wako Pure Chemical Industries, Ltd., Japan) and about 0.02 g of internal standard in the form of toluene (dehydrated, Wako Pure Chemical Industries, Ltd., Japan) and mixing to uniformity to obtain solutions used as gas chromatography analysis samples.
(2) Quantitative Analysis
   Analyses were performed for each standard and quantitative analyses were performed on the analysis sample solutions based on the resulting calibration curve.
4) Inductively Coupled Plasma Mass Spectrometry
   Apparatus: SPQ-8000, Seiko Epson Corp., Japan
(1) Inductively Coupled Plasma Mass Spectrometry Analysis Samples
   About 0.15 g of sample were ashed with dilute sulfuric acid followed by dissolving in dilute nitric acid.

(2) Quantitative Analysis

Analyses were performed for each standard and quantitative analyses were performed on the analysis sample solutions based on the resulting calibration curve.

Reference Example 1

Production of Bis(3-methylbutyl)Carbonate

Step (I-1): Production of Dialkyl Tin Catalyst 625 g (2.7 mol) of di-n-butyl tin oxide (Sankyo Organic Chemicals Co., Ltd., Japan) and 2020 g (22.7 mol) of 3-methyl-1-butanol (Wako Pure Chemical Industries, Ltd., Japan) were placed in a 5000 mL volumetric pear-shaped flask. The flask was connected to an evaporator (R-144, Shibata Co., Ltd., Japan) to which was connected an oil bath (OBH-24, Masuda Corp., Japan) equipped with a temperature controller, a vacuum pump (G-50A, Ulvac Inc., Japan) and a vacuum controller (VC-10S, Okano Seisakusho Co., Ltd.). The purge valve outlet of this evaporator was connected to a line containing nitrogen gas flowing at a normal pressure. After closing the purge valve of the evaporator to a reduce pressure inside the system, the purge valve was opened gradually to allow nitrogen to flow into the system and return to the normal pressure. The oil bath temperature was set to be about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at from 74 to 35 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 886 g of reaction liquid were obtained in the flask. Based on the results of $^{119}$Sn-, $^1$H- and $^{13}$C-NMR analyses, 1,1,3,3-tetra-n-butyl-1,3-bis(3-methylbutyloxy) distannoxane was confirmed to have been obtained at a yield of 99% based on di-n-butyl tin oxide. The same procedure was then repeated 12 times to obtain a total of 10635 g of 1,1,3,3-tetra-n-butyl-1,3-bis(3-methylbutyloxy)distannoxane.

Step (I-2): Production of Bis(3-methylbutyl)Carbonate

Figure 1:
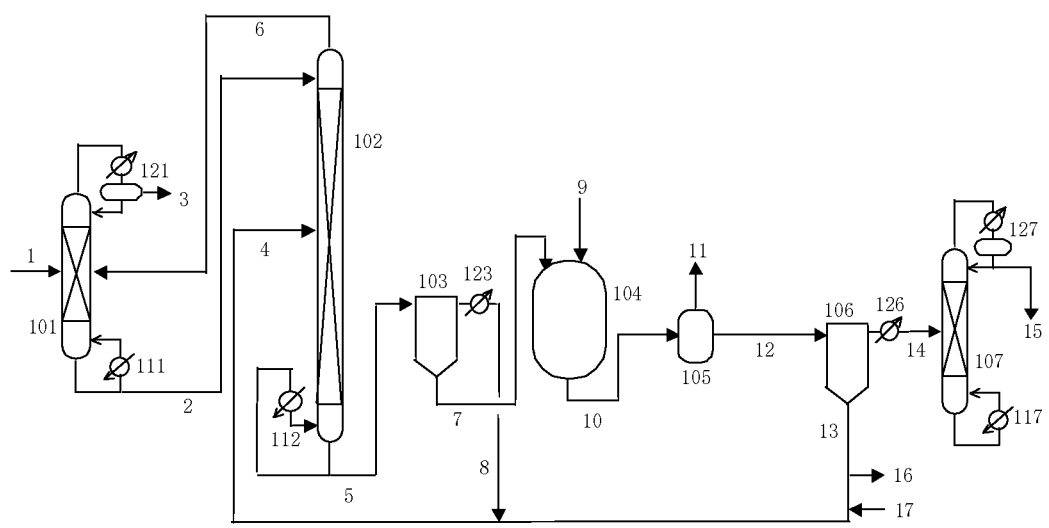
FIG. 1 is a conceptual drawing showing a continuous production apparatus for producing carbonic acid ester according to an embodiment of the present invention.

Bis(3-methylbutyl)carbonate was produced in a continuous production apparatus like that shown in FIG. 1. 1,1,3,3-Tetra-n-butyl-1,3-bis(3-methylbutyloxy)distannoxane produced in the manner described above was supplied at the rate of 4388 g/hr from a line 4 into column-type reaction vessel 102 packed with Metal Gauze CY Packing (Sulzer Chemtech Ltd., Switzerland) and having an inner diameter of 151 mm and effective length of 5040 mm, and 3-methyl-1-butanol purified with continuous multistage distillation column 101 was supplied at the rate of 14953 g/hr from line 2. The liquid temperature inside reaction vessel 102 was controlled to 160° C. by a heater and reboiler 112, and the pressure was adjusted to be about 120 kPa-G with a pressure control valve. The residence time in the reaction vessel was about 17 minutes. 3-methyl-1-butanol containing water at the rate of 15037 g/hr from a top of the reaction vessel via line 6, and 3-methyl-1-butanol at the rate of 825 g/hr via line 1, were pumped to distillation column 101 packed with Metal Gauze CY Packing and provided with reboiler 111 and condenser 121 to carry out distillative purification. In the top of distillation column 101, a fraction containing a high concentration of water was condensed by condenser 121 and recovered from line 3. Purified 3-methyl-1-butanol was pumped to column-type reaction vessel 102 via line 2 located in the lower portion of distillation column 101. An alkyl tin alkoxide catalyst composition containing di-n-butyl-bis(3-methylbutyloxy)tin and 1,1,3,3-tetra-n-butyl-1,3-bis(3-methylbutyloxy)distannoxane was obtained from the lower portion of column-type reaction vessel 102, and supplied to thin film evaporator 103 (Kobelco Eco-Solutions Co., Ltd., Japan) via line 5. The 3-methyl-1-butanol was distilled off in thin film evaporator 103 and returned to column-type reaction vessel 102 via condenser 123, line 8 and line 4. The alkyl tin alkoxide catalyst composition was pumped from the lower portion of thin film evaporator 103 via line 7 and supplied to autoclave 104 while adjusting the flow rate of di-n-butyl-bis(3-methylbutyloxy) tin and 1,1,3,3-tetra-n-butyl-1,3-bis(3-methylbutyloxy)distannoxane to about 5130 g/hr. Carbon dioxide was supplied to autoclave 104 by line 9 at the rate of 973 g/hr, and the pressure inside autoclave 104 was maintained at 4 MPa-G. The temperature inside autoclave 104 was set to be 120° C., the residence time was adjusted to about 4 hours, and a reaction between the carbon dioxide and the alkyl tin alkoxide catalyst composition was carried out to obtain a reaction liquid containing bis(3-methylbutyl)carbonate. This reaction liquid was transferred to a decarbonization tank 105 via line 10 and a control valve to remove residual carbon dioxide, and the carbon dioxide was recovered from line 11. Subsequently, the reaction liquid was transferred to thin film evaporator 106 (Kobelco Eco-Solutions Co., Ltd., Japan) set to be about 142° C. and about 0.5 kPa via line 12, and supplied while adjusting the flow rate of 1,1,3,3-tetra-n-butyl-1,3-bis(3-methylbutyloxy)distannoxane to about 4388 g/hr to obtain a fraction containing bis(3-methylbutyl)carbonate. On the other hand, the evaporation residue was circulated to column-type reaction vessel 102 via line 13 and line 4 while adjusting the flow rate of 1,1,3,3-tetra-n-butyl-1,3-bis(3-methylbutyloxy)distannoxane to about 4388 g/hr. The fraction containing bis(3-methylbutyl)carbonate was supplied to a distillation column 107 packed with Metal Gauze CY packing and equipped with reboiler 117 and condenser 127 via condenser 126 and transfer line 14 at the rate of 959 g/hr followed by distillative purification to obtain 99 wt % bis(3-methylbutyl)carbonate from recovery line 15 at the rate of 944 g/hr. When the alkyl tin alkoxide catalyst composition of transfer line 13 was analyzed by $^{119}$Sn-, $^1$H- and $^{13}$C-NMR analysis, it was found to contain 1,1,3,3-tetra-n-butyl-1,3-bis(3-methylbutyloxy) distannoxane but not contain di-n-butyl-bis(3-methylbutyloxy)tin. After carrying out the above-mentioned continuous operation for about 240 hours, alkyl tin alkoxide catalyst composition was extracted from extraction line 16 at the rate of 18 g/hr, while 1,1,3,3-tetra-n-butyl-1,3-bis(3-methylbutyloxy)distannoxane produced according to the above process was supplied from line 17 at the rate of 18 g/hr. The resulting bis(3-methylbutyl)carbonate contained 23 ppm of metal atoms in the form of iron.

Reference Example 2

Production of Dibutyl Carbonate

Step (II-1): Production of Dialkyl Tin Catalyst 692 g (2.78 mol) of di-n-butyl tin oxide and 2001 g (27 mol) of 1-butanol (Wako Pure Chemical Industries, Ltd., Japan) were placed in a 3000 mL volumetric pear-shaped flask. The flask containing a mixture in the form of a white slurry was connected to an evaporator to which was connected an oil bath equipped with a temperature controller, a vacuum pump and a vacuum controller. The purge valve outlet of the evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to be 126° C., the flask was immersed in the oil bath and rotation of the evaporator was started. After heating for about 30 minutes at a normal pressure with the purge valve of the evaporator left open, the mixture boiled and distillation of a low boiling point component began. After maintaining in this state for 8 hours, the purge valve was closed, pressure inside the system was gradually reduced, and residual low boiling point component was distilled with the pressure inside the system at from 76 to 54 kPa. After the low boiling point component no longer appeared, the flask was taken out of the oil bath. The reaction liquid was in the form of a clear liquid. Subsequently, the flask was taken out of the oil bath, the purge valve was opened gradually and the pressure inside the system was returned to normal pressure. 847 g of reaction liquid were obtained in the flask. Based on the results of $^{119}$Sn-, $^1$H- and $^{13}$C-NMR analyses, 1,1,3,3-tetra-n-butyl-1,3-di(n-butyloxy)distannoxane was obtained at a yield of 99% based on di-n-butyl tin oxide. The same procedure was then repeated 12 times to obtain a total of 10180 g of 1,1,3,3-tetra-n-butyl-1,3-di(n-butyloxy)distannoxane.

Step (II-2): Production of Dibutyl Carbonate

Carbonic acid ester was produced in a continuous production apparatus like that shown in FIG. 1. 1,1,3,3-Tetra-n-butyl-1,3-di(n-butyloxy)distannoxane produced in Step (II-1) was supplied at the rate of 4201 g/hr from feed line 4 into a column-type reaction vessel packed with Mellapak 750Y packing (Sulzer Chemtech Ltd., Switzerland) and having an inner diameter of 151 mm and effective length of 5040 mm, and 1-butanol purified with continuous multistage distillation column 101 was supplied to column-type reaction vessel 102 at the rate of 24717 g/hr from line 2. The liquid temperature inside reaction vessel 102 was adjusted to 160° C. by heater and reboiler 112, and the pressure was adjusted to be about 120 kPa-G with a pressure control valve. The residence time in the reaction vessel was about 10 minutes. 1-butanol containing water at the rate of 24715 g/hr from a top of the reaction vessel via line 6, and 1-butanol at the rate of 824 g/hr via feed line 1, were pumped to continuous multistage distillation column 101 packed with Metal Gauze CY Packing (Sulzer Chemtech Ltd., Switzerland) and provided with reboiler 111 and condenser 121 to carry out distillative purification. In the top of continuous multistage distillation column 101, a fraction containing a high concentration of water was condensed by condenser 121 and recovered from transfer line 3. Purified 1-butanol was pumped via line 2 located in the lower portion of continuous multistage distillation column 101. An alkyl tin alkoxide catalyst composition containing di-n-butyl tin-di-n-butyloxide and 1,1,3,3-tetra-n-butyl-1,3-di(n-butyloxy)distannoxane was obtained from the lower portion of column-type reaction vessel 102, and supplied to thin film evaporator 103 (Kobelco Eco-Solutions Co., Ltd., Japan) via line 5. The 1-butanol was distilled off in thin film evaporator 103 and returned to column-type reaction vessel 102 via condenser 123, transfer line 8 and transfer line 4. The alkyl tin alkoxide catalyst composition was pumped from the lower portion of thin film evaporator 103 via line 7 and supplied to autoclave 104 while adjusting the flow rate of the active components in the form of di-n-butyl tin-di-n-butyloxide and 1,1,3,3-tetra-n-butyl-1,3-di(n-butyloxy)distannoxane to about 4812 g/hr. Carbon dioxide was supplied to autoclave 104 by feed line 9 at the rate of 973 g/hr, and the pressure inside autoclave 104 was maintained at 4 MPa-G. The temperature inside the autoclave was set to be 120° C., the residence time was adjusted to about 4 hours, and a reaction between the carbon dioxide and the alkyl tin alkoxide catalyst composition was carried out to obtain a reaction liquid containing dibutyl carbonate. This reaction liquid was transferred to decarbonization tank 105 via line 10 and a control valve to remove residual carbon dioxide, and the carbon dioxide was recovered from line 11. Subsequently, the reaction liquid was pumped to thin film evaporator 106 (Kobelco Eco-Solutions Co., Ltd., Japan) set to be 140° C. and about 1.4 kPa via line 12, and supplied while adjusting the flow rate of 1,1,3,3-tetra-n-butyl-1,3-di(n-butyloxy)distannoxane to about 4201 g/hr to obtain a fraction containing dibutyl carbonate. On the other hand, the evaporation residue was circulated to column-type reaction vessel 102 via line 13 and line 4 while adjusting the flow rate of 1,1,3,3-tetra-n-butyl-1,3-di(n-butyloxy)distannoxane to about 4201 g/hr. The fraction containing dibutyl carbonate was supplied to distillation column 107 packed with Metal Gauze CY packing (Sulzer Chemtech Ltd., Switzerland) and equipped with reboiler 117 and condenser 127 via condenser 126 and line 14 at the rate of 830 g/hr followed by distillative purification to obtain 99 wt % dibutyl carbonate from transfer line 15 at the rate of 814 g/hr. When the alkyl tin alkoxide catalyst composition of transfer line 13 was analyzed by $^{119}$Sn-, $^1$H- and $^{13}$C-NMR analysis, it was found to contain 1,1,3,3-tetra-n-butyl-1,3-di(n-butyloxy)distannoxane but not contain di-n-butyl tin-di-n-butyloxide. After carrying out the above-mentioned continuous operation for about 600 hours, alkyl tin alkoxide catalyst composition was extracted from extraction line 16 at the rate of 16 g/hr, while 1,1,3,3-tetra-n-butyl-1,3-di(n-butyloxy)distannoxane produced in step (II-1) was supplied from line 17 at the rate of 16 g/hr. The resulting dibutyl carbonate contained 0.3 ppm of metal atoms in the form of iron.

Reference Example 3

Production of Bis(2-ethylbutyl)Carbonate

Step (III-1): Production of Dialkyl Tin Catalyst 893 g (2.48 mol) of di-n-octyl tin oxide (Sankyo Organic Chemicals Co., Ltd., Japan) and 2403 g (23.6 mol) of 2-ethyl-1-butanol were placed in a 5000 mL volumetric pear-shaped flask. The flask was connected to an evaporator to which was connected an oil bath equipped with a temperature controller, a vacuum pump and a vacuum controller. The purge valve outlet of the evaporator was connected to a line containing nitrogen gas flowing at a normal pressure. After closing the purge valve of the evaporator to reduce pressure inside the system, the purge valve was opened gradually to allow nitrogen to flow into the system and return to the normal pressure. The oil bath temperature was set to be about 165° C., the flask was immersed in the oil bath and rotation of the evaporator was started. After heating for about 40 minutes in the presence of nitrogen at atmospheric pressure with the purge valve of the evaporator left open, distillation of 2-ethyl-1-butanol containing water began. After maintaining in this state for 7 hours, the purge valve was closed, pressure inside the system was gradually reduced, and residual 2-ethyl-1-butanol was distilled with the pressure inside the system at from 74 to 25 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1125 g of reaction liquid were obtained in the flask. Based on the results of $^{119}$Sn-, $^1$H- and $^{13}$C-NMR analyses, 1,1,3,3-tetra-n-octyl-1,3-bis(2-ethylbutyloxy)distannoxane was confirmed to have been obtained at a yield of 99% based on di-n-octyl tin oxide. The same procedure was then repeated 12 times to obtain a total of 13510 g of 1,1,3,3-tetra-n-octyl-1,3-bis(2-ethylbutyloxy)distannoxane.

Step (III-2): Production of Carbonic Acid Ester and Recovery of Deactivated Composition of Dialkyl Tin Catalyst Carbonic acid ester was produced in a continuous production apparatus like that shown in FIG. 1. 1,1,3,3-Tetra-n-octyl-1,3-bis(2-ethylbutyloxy)distannoxane produced in the manner described above was supplied at the rate of 6074 g/hr from line 4 into column-type reaction vessel 102 packed with Metal Gauze CY packing and having an inner diameter of 151 mm and effective length of 5040 mm, and 2-ethyl-1-butanol purified with continuous multistage distillation column 101 was supplied at the rate of 12260 g/hr from line 2. The liquid temperature inside reaction vessel 102 was adjusted to 160° C. by a heater and reboiler 112, and the pressure was adjusted to about 120 kPa-G with a pressure control valve. The residence time in the reaction vessel was about 17 minutes. 2-ethyl-1-butanol containing water at the rate of 12344 g/hr from the top of the reaction vessel via line 6, and 2-ethyl-1-butanol at the rate of 958 g/hr via line 1, were pumped to continuous multistage distillation column 101 packed with Metal Gauze CY Packing and provided with reboiler 111 and condenser 121 to carry out distillative purification. In the top of continuous multistage distillation column 101, a fraction containing a high concentration of water was condensed by condenser 121 and recovered from recovery line 3. Purified 2-ethyl-1-butanol was pumped column-type reaction vessel 102 via line 2 located in the lower portion of continuous multistage distillation column 101. An alkyl tin alkoxide catalyst composition containing di-n-octyl-bis(2-ethylbutyloxy) tin and 1,1,3,3-tetra-n-octyl-1,3-bis(2-ethylbutyloxy)distannoxane was obtained from the lower portion of column-type reaction vessel 102, and supplied to thin film evaporator 103 via line 5. The 2-ethyl-1-butanol was distilled off in thin film evaporator 103 and returned to column-type reaction vessel 102 via condenser 123, line 8 and line 4. The alkyl tin alkoxide catalyst composition was pumped from the lower portion of thin film evaporator 103 via line 7 and supplied to autoclave 104 while adjusting the flow rate of di-n-octyl-bis(2-ethylbutyloxy)tin and 1,1,3,3-tetra-n-octyl-1,3-bis(2-ethylbutyloxy)distannoxane to about 6945 g/hr. Carbon dioxide was supplied to autoclave 104 by line 9 at the rate of 973 g/hr, and the pressure inside autoclave 104 was maintained at 4 MPa-G. The temperature inside the autoclave was set to be 120° C., the residence time was adjusted to about 4 hours, and a reaction between the carbon dioxide and the alkyl tin alkoxide catalyst composition was carried out to obtain a reaction liquid containing bis(2-ethylbutyl)carbonate. This reaction liquid was transferred to decarbonization tank 105 via line 10 and a control valve to remove residual carbon dioxide, and the carbon dioxide was recovered from line 11. Subsequently, the reaction liquid was transferred to thin film evaporator 106 set to about 142° C. and about 0.5 kPa via line 12, and supplied while adjusting the flow rate of 1,1,3,3-tetra-n-octyl-1,3-bis(2-ethylbutyloxy)distannoxane to about 6074 g/hr to obtain a fraction containing bis(2-ethylbutyl)carbonate. On the other hand, the evaporation residue was circulated to column-type reaction vessel 102 via line 13 and line 4 while adjusting the flow rate of 1,1,3,3-tetra-n-octyl-1,3-bis(2-ethylbutyloxy) distannoxane to about 6704 g/hr. The fraction containing bis(2-ethylbutyl)carbonate was supplied to distillation column 107 packed with Metal Gauze CY packing and equipped with reboiler 117 and condenser 127 via condenser 126 and line 14 at the rate of 959 g/hr followed by distillative purification to obtain 99 wt % bis(2-ethylbutyl)carbonate from recovery line 15 at the rate of 1075 g/hr. When the alkyl tin alkoxide catalyst composition of line 13 was analyzed by $^{119}$Sn-, $^1$H- and $^{13}$C-NMR analysis, it was found to contain 1,1,3,3-tetra-n-octyl-1,3-bis(2-ethylbutyloxy)distannoxane but not contain di-n-octyl-bis(2-ethylbutyloxy)tin. After carrying out the above-mentioned continuous operation for about 220 hours, alkyl tin alkoxide catalyst composition was supplied from extraction line 16 at the rate of 18 g/hr, 1,1,3,3-tetra-n-octyl-1,3-bis(2-ethylbutyloxy)distannoxane produced in the manner described above was supplied from line 17 at the rate of 18 g/hr, and 180 g of a deactivated catalyst composition of 1,1,3,3-tetra-n-octyl-1,3-bis(2-ethylbutyloxy)distannoxane was extracted from extraction line 16. The resulting bis(2-ethylbutyl)carbonate contained 4.8 ppm of metal atoms in the form of iron.

Reference Example 4

Production of Diheptyl Carbonate

Step (IV-1): Production of Dialkyl Tin Catalyst 692 g (2.78 mol) of di-n-butyl tin oxide and 3137 g (27 mol) of 1-heptanol (Wako Pure Chemical Industries, Ltd., Japan) were placed in a 3000 mL volumetric pear-shaped flask. The flask containing a mixture in the form of a white slurry was attached to an evaporator to which was connected an oil bath equipped with a temperature controller, a vacuum pump and a vacuum controller. The purge valve outlet of the evaporator was connected to a line containing nitrogen gas flowing at normal pressure. After closing the purge valve of the evaporator to reduce pressure inside the system, the purge valve was opened gradually to allow nitrogen to flow into the system and reach a pressure of 39 kPa. The oil bath temperature was set to be 150° C., the flask was immersed in the oil bath and rotation of the evaporator was started. After heating for about 30 minutes at a normal pressure with the purge valve of the evaporator left open, the mixture boiled and distillation of a low boiling point component began. After maintaining in this state for 8 hours, the purge valve was closed, pressure inside the system was gradually reduced, and residual low boiling point component was distilled with the pressure inside the system at from 39 to 10 kPa. After the low boiling point component no longer appeared, the flask was taken out of the oil bath. The reaction liquid was in the form of a clear liquid. Subsequently, the flask was taken out of the oil bath, the purge valve was opened gradually and the pressure inside the system was returned to the normal pressure. 952 g of reaction liquid were obtained in the flask. Based on the results of $^{119}$Sn-, $^1$H- and $^{13}$C-NMR analyses, 1,1,3,3-tetra-n-butyl-1,3-diheptyloxy distannoxane was obtained at a yield of 99% based on di-n-butyl tin oxide. The same procedure was then repeated 12 times to obtain a total of 11431 g of 1,1,3,3-tetra-n-butyl-1,3-diheptyloxy distannoxane.

Step (IV-2): Production of Diheptyl Carbonate

Carbonic acid ester was produced in a continuous production apparatus like that shown in FIG. 1. 1,1,3,3-Tetra-n-butyl-1,3-di-n-heptyloxy distannoxane produced in Step (IV-1) was supplied at the rate of 4757 g/hr from line 4 into a column-type reaction vessel packed with Mellapak 750Y packing (Sulzer Chemtech Ltd., Switzerland) and having an inner diameter of 151 mm and effective length of 5040 mm, and 1-heptanol purified with continuous multistage distillation column 101 was supplied to column-type reaction vessel 102 at the rate of 13967 g/hr from line 2. The liquid temperature inside the reaction vessel was adjusted to 170° C. by a heater and reboiler 112, and the pressure was adjusted to be about 120 kPa-G with a pressure control valve. The residence time in the reaction vessel was about 10 minutes. 1-heptanol containing water at the rate of 14051 g/hr from the top of the reaction vessel via line 6, and 1-heptanol at the rate of 1086 g/hr via line 1, were pumped to continuous multistage distillation column 101 packed with Metal Gauze CY Packing (Sulzer Chemtech Ltd., Switzerland) and provided with reboiler 111 and condenser 121 to carry out distillative purification. In the top of continuous multistage distillation column 101, a fraction containing a high concentration of water was condensed by condenser 121 and recovered from line 3. Purified 1-heptanol was pumped via transfer line 2 located in the lower portion of continuous multistage distillation column 101. An alkyl tin alkoxide catalyst composition containing di-n-butyl tin-di-n-heptyloxide and 1,1,3,3-tetra-n-butyl-1,3-di-n-heptyloxy distannoxane was obtained from the lower portion of column-type reaction vessel 102, and supplied to thin film evaporator 103 (Kobelco Eco-Solutions Co., Ltd., Japan) via line 5. The 1-heptanol was distilled off in thin film evaporator 103 and returned to column-type reaction vessel 102 via condenser 123, line 8 and line 4. The alkyl tin alkoxide catalyst composition was pumped from the lower portion of thin film evaporator 103 via line 7 and supplied to autoclave 104 while adjusting the flow rate of the active components in the form of di-n-butyl tin-di-n-heptyloxide and 1,1,3,3-tetra-n-butyl-1,3-di-n-heptyloxy distannoxane to about 5764 g/hr. Carbon dioxide was supplied to autoclave 104 by line 9 at the rate of 973 g/hr, and the pressure inside autoclave 104 was maintained at 4 MPa-G. The temperature inside the autoclave was set to be 120° C., the residence time was adjusted to about 4 hours, and a reaction between the carbon dioxide and the alkyl tin alkoxide catalyst composition was carried out to obtain a reaction liquid containing diheptyl carbonate. The reaction liquid was transferred to decarbonization tank 105 via line 10 and a control valve to remove residual carbon dioxide, and the carbon dioxide was recovered from line 11. Subsequently, the reaction liquid was pumped to thin film evaporator 106 (Kobelco Eco-Solutions Co., Ltd., Japan) set to be 140° C. and about 1.4 kPa via line 12, and supplied while adjusting the flow rate of 1,1,3,3-tetra-n-butyl-1,3-di-n-heptyloxy distannoxane to about 4757 g/hr to obtain a fraction containing dibutyl carbonate. On the other hand, the evaporation residue was circulated to column-type reaction vessel 102 via line 13 and line 4 while adjusting the flow rate of 1,1,3,3-tetra-n-butyl-1,3-di-n-heptyloxy distannoxane to be about 5764 g/hr. The fraction containing diheptyl carbonate was supplied to distillation column 107 packed with Metal Gauze CY packing (Sulzer Chemtech Ltd., Switzerland) and equipped with reboiler 117 and condenser 127 via condenser 126 and line 14 at the rate of 1223 g/hr followed by distillative purification to obtain 99 wt % diheptyl carbonate from line 15 at the rate of 1208 g/hr. When the alkyl tin alkoxide catalyst composition of line 13 was analyzed by $^{119}$Sn, $^1$H- and $^{13}$C-NMR analysis, it was found to contain 1,1,3,3-tetra-n-butyl-1,3-di-n-heptyloxy distannoxane but not contain di-n-butyl tin-di-n-heptyloxide. After carrying out the above-mentioned continuous operation for about 600 hours, alkyl tin alkoxide catalyst composition was extracted from extraction line 16 at the rate of 22 g/hr, while 1,1,3,3-tetra-n-butyl-1,3-di-n-heptyloxy distannoxane produced in step (IV-1) was supplied from feed line 17 at the rate of 22 g/hr. The resulting diheptyl carbonate contained 26 ppm of metal atoms in the form of iron.

Reference Example 5

Production of Bis(2-ethylhexyl)Carbonate

Step (V-1): Production Dialkyl Tin Catalyst 692 g (2.78 mol) of di-n-butyl tin oxide and 3516 g (27 mol) of 2-ethyl-1-hexanol (Wako Pure Chemical Industries, Ltd., Japan) were placed in a 3000 mL volumetric pear-shaped flask. The flask containing a mixture in the form of a white slurry was attached to an evaporator to which was connected an oil bath equipped with a temperature controller, a vacuum pump and a vacuum controller. The purge valve outlet of the evaporator was connected to a line containing nitrogen gas flowing at a normal pressure. After closing the purge valve of the evaporator to reduce pressure inside the system, the purge valve was opened gradually to allow nitrogen to flow into the system and reach a pressure of about 26 kPa. The oil bath temperature was set to be 150° C., the flask was immersed in the oil bath and rotation of the evaporator was started. After heating for about 30 minutes at the normal pressure with the purge valve of the evaporator left open, the mixture boiled and distillation of a low boiling point component began. After maintaining in this state for 8 hours, the purge valve was closed, pressure inside the system was gradually reduced, and residual low boiling point component was distilled with the pressure inside the system at 26 to 10 kPa. After the low boiling point component no longer appeared, the flask was taken out of the oil bath. The reaction liquid was in the form of a clear liquid. Subsequently, the flask was taken out of the oil bath, the purge valve was opened gradually and the pressure inside the system was returned to the normal pressure. 990 g of reaction liquid were obtained in the flask. Based on the results of $^{119}$Sn-, $^1$H- and $^{13}$C-NMR analyses, 1,1,3,3-tetra-n-butyl-1,3-bis(2-ethylhexyloxy)distannoxane was obtained at a yield of 99% based on di-n-butyl tin oxide. The same procedure was then repeated 12 times to obtain a total of 11880 g of 1,1,3,3-tetra-n-butyl-1,3-bis(2-ethylhexyloxy)distannoxane.

Step (V-2): Production of Bis(2-ethylhexyl)Carbonate

Carbonic acid ester was produced in a continuous production apparatus like that shown in FIG. 1. 1,1,3,3-Tetra-n-butyl-1,3-bis(2-ethylhexyloxy)distannoxane produced in Step (V-1) was supplied at the rate of 4943 g/hr from line 4 into a column-type reaction vessel packed with Mellapak 750Y packing (Sulzer Chemtech Ltd., Switzerland) and having an inner diameter of 151 mm and effective length of 5040 mm, and 2-ethyl-1-hexanol purified with continuous multistage distillation column 101 was supplied to column-type reaction vessel 102 at the rate of 15653 g/hr from line 2. The liquid temperature inside the reaction vessel was adjusted to be 170° C. by a heater and reboiler 112, and the pressure was adjusted to be about 120 kPa-G with a pressure control valve. The residence time in the reaction vessel was about 10 minutes. 2-Ethyl-1-hexanol containing water at the rate of 15737 g/hr from the top of the reaction vessel via line 6, and 2-ethyl-1-hexanol at the rate of 1217 g/hr via line 1, were pumped to continuous multistage distillation column 101 packed with Metal Gauze CY Packing (Sulzer Chemtech Ltd., Switzerland) and provided with reboiler 111 and condenser 121 to carry out distillative purification. In the top of continuous multistage distillation column 101, a fraction containing a high concentration of water was condensed by condenser 121 and recovered from line 3. Purified 2-ethyl-1-hexanol was pumped via line 2 located in the lower portion of continuous multistage distillation column 101. An alkyl tin alkoxide catalyst composition containing di-n-butyl tin-bis(2-ethylhexyloxide) and 1,1,3,3-tetra-n-butyl-1,3-bis(2-ethylhexyloxy)distannoxane was obtained from the lower portion of column-type reaction vessel 102, and supplied to thin film evaporator 103 (Kobelco Eco-Solutions Co., Ltd., Japan) via line 5. The 2-ethyl-1-hexanol was distilled off in thin film evaporator 103 and returned to column-type reaction vessel 102 via condenser 123, line 8 and line 4. The alkyl tin alkoxide catalyst composition was pumped from the lower portion of thin film evaporator 103 via line 7 and supplied to autoclave 104 while adjusting the flow rate of the active components in the form of di-n-butyl tin-bis(2-ethylhexyloxide) and 1,1,3,3-tetra-n-butyl-1,3-bis(2-ethylhexyloxy)distannoxane to about 6083 g/hr. Carbon dioxide was supplied to the autoclave by line 9 at the rate of 973 g/hr, and the pressure inside the autoclave was maintained at 4 MPa-G. The temperature inside the autoclave was set to be 120° C., the residence time was adjusted to about 4 hours, and a reaction between the carbon dioxide and the alkyl tin alkoxide catalyst composition was carried out to obtain a reaction liquid containing bis(2-ethylhexyl)carbonate. This reaction liquid was transferred to decarbonization tank 105 via line 10 and a control valve to remove residual carbon dioxide, and the carbon dioxide was recovered from line 11. Subsequently, the reaction liquid was pumped to thin film evaporator 106 (Kobelco Eco-Solutions Co., Ltd., Japan) set to 140° C. and about 1.4 kPa via line 12, and supplied while adjusting the flow rate of 1,1,3,3-tetra-n-butyl-1,3-bis(2-ethylhexyloxy)distannoxane to about 4943 g/hr to obtain a fraction containing dibutyl carbonate. On the other hand, the evaporation residue was circulated to column-type reaction vessel 102 via transfer line 13 and transfer line 4 while adjusting the flow rate of 1,1,3,3-tetra-n-butyl-1,3-bis(2-ethylhexyloxy)distannoxane to about 4943 g/hr. The fraction containing dibutyl carbonate was supplied to distillation column 107 packed with Metal Gauze CY packing (Sulzer Chemtech Ltd., Switzerland) and equipped with reboiler 117 and condenser 127 via condenser 126 and line 14 at the rate of 1354 g/hr followed by distillative purification to obtain 99 wt % bis(2-ethylhexyl)carbonate from transfer line 15 at the rate of 1339 g/hr. When the alkyl tin alkoxide catalyst composition of line 13 was analyzed by $^{119}$Sn-, $^{1}$H- and $^{13}$C-NMR analysis, it was found to contain 1,1,3,3-tetra-n-butyl-1,3-bis(2-ethylhexyloxy)distannoxane but not contain di-n-butyl tin-bis(2-ethylhexyloxide). After carrying out the above-mentioned continuous operation for about 600 hours, alkyl tin alkoxide catalyst composition was extracted from extraction line 16 at the rate of 23 g/hr, while 1,1,3,3-tetra-n-butyl-1,3-bis(2-ethylhexyloxy)distannoxane produced in step (V-1) was supplied from feed line 17 at the rate of 23 g/hr. The resulting bis(2-ethylhexyl)carbonate contained 30 ppm of metal atoms in the form of iron.

Reference Example 6

Production of Diphenyl Carbonate

Diphenyl carbonate was produced using the dibutyl carbonate obtained in Reference Example 2.

Step (VI-1): Production of Aromatic Carbonic Acid Ester

[Preparation of Catalyst]

79 g of phenol and 32 g of lead monoxide were heated for 10 hours at 180° C. after which the water formed was distilled off together with phenol. About 2.5 g of water were extracted in 10 hours. Subsequently, phenol was distilled off from an upper portion of the reaction vessel to prepare a catalyst.

[Production of Aromatic Carbonic Acid Ester]

Figure 2:
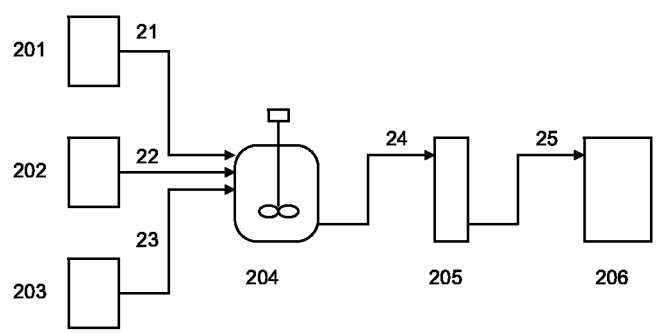
FIG. 2 is a conceptual drawing showing a carbamic acid ester production apparatus according to an embodiment of the present invention.

An apparatus like that shown in FIG. 2 was used.

A mixture comprising the dibutyl carbonate obtained in step (I-2), phenol and the catalyst prepared above (adjusted so that the weight ratio of dibutyl carbonate and phenol in the mixture was about 65/35 and the lead concentration was about 1% by weight) was continuously fed in a liquid state through preheater 201 to the middle stage of continuous multistage distillation column 202 packed with Dickson packing (diameter: 6 mm) and having an inner diameter of about 5 cm and column length of 2 m from line 21 at the rate of about 270 g/hr and allowed to react. The amount of heat required for the reaction and distillation was supplied by circulating the liquid in the bottom of the column through line 23 and reboiler 204. The liquid temperature in the bottom of continuous multistage distillation column 202 was 238° C., the pressure at the top of the column was about 250 kPa, and the reflux ratio was set to be about 2. Gas distilled from the top of continuous multistage distillation column 202 was extracted from line 22, and continuously extracted into storage tank 205 through condenser 203 from line 24 at the rate of about 67 g/hr. Liquid was continuously extracted from the bottom of the column through line 23 into storage tank 206 at the rate of about 204 g/hr.

The composition of the liquid extracted from line 24 consisted of about 33% by weight of 1-butanol, about 65% by weight of phenol and about 2% by weight of dibutyl carbonate. The composition of the liquid extracted to storage tank 206 consisted of about 11% by weight of phenol, about 60% by weight of dibutyl carbonate, about 26% by weight of butylphenyl carbonate, and about 1.6% by weight of diphenyl carbonate, and the lead concentration was about 1% by weight.

Figure 3:
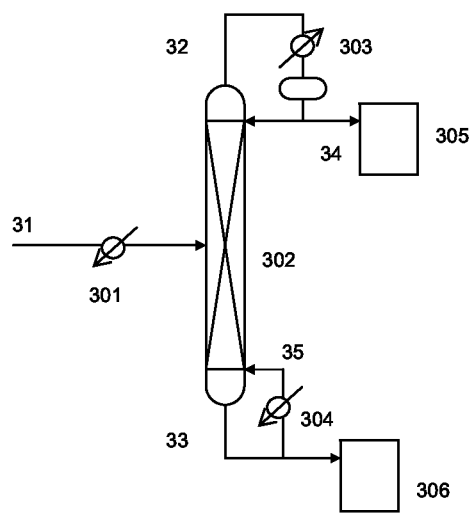
FIG. 3 is a conceptual drawing showing a low boiling point component distillation apparatus according to an embodiment of the present invention.

Next, an apparatus like that shown in FIG. 3 was used.

Liquid extracted into storage tank 206 was continuously fed in a liquid state through preheater 301 to the middle stage of continuous multistage distillation column 302 packed with Dickson packing (diameter: 6 mm) and having an inner diameter of 5 cm and column length of 2 m from line 31 at the rate of about 203 g/hr. The amount of heat required for the reaction and distillation was supplied by circulating the liquid in the bottom of the column through line 33 and reboiler 304. The liquid temperature in the bottom of continuous multistage distillation column 302 was 240° C., the pressure at the top of the column was about 27 kPa, and the reflux ratio was set to about 2. Gas distilled from the top of continuous multistage distillation column 302 was condensed in condenser 303 via line 32 and continuously extracted from line 34 into storage tank 305 at the rate of about 165 g/hr. Liquid was continuously extracted from the bottom of the column through line 33 into storage tank 306 at the rate of about 39 g/hr.

The composition of the liquid extracted from line 34 consisted of about 500 ppm of 1-butanol, about 13% by weight of phenol, about 85% by weight of dibutyl carbonate and about 2% by weight of butylphenyl carbonate. The composition of the liquid extracted to storage tank 306 consisted of about 0.3% by weight of dibutyl carbonate, about 32% by weight of butylphenyl carbonate, and about 61% by weight of diphenyl carbonate, and the lead concentration was about 7% by weight.

[Recycling of Alcohol]

Figure 4:
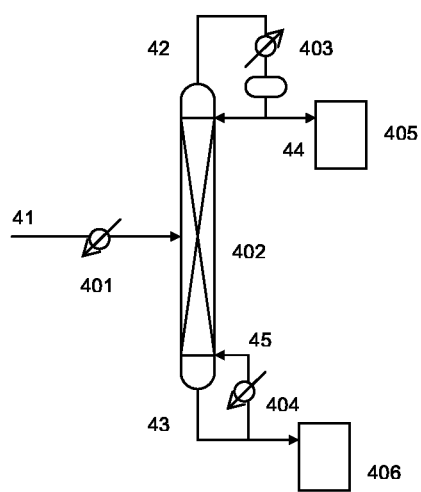
FIG. 4 is a conceptual drawing showing a low boiling point component distillation apparatus according to an embodiment of the present invention.

Alcohol was recycled using an apparatus like that shown in FIG. 4.

Liquid continuously extracted into storage tank 205 was continuously fed through a preheater 401 to a position of about 0.7 m from the bottom of continuous multistage distillation column 402 packed with Dickson packing (diameter: 6 mm) and having an inner diameter of 5 cm and column length of 2 m from line 41 at the rate of about 201 g/hr to carry out distillative separation. The amount of heat required for the distillative separation was supplied by circulating the liquid in the bottom of the column through line 43 and reboiler 404. The liquid temperature in the bottom of continuous multistage distillation column 402 was 145° C., the pressure at the top of the column was about 13 kPa, and the reflux ratio was set to be about 0.3. Gas distilled from the top of continuous multistage distillation column 402 was condensed in condenser 403 via line 42 and extracted from line 44 into storage tank 405 at the rate of about 68 g/hr. Liquid was continuously extracted from the bottom of the column through line 43 into storage tank 406 at the rate of about 133 g/hr.

The composition of the liquid extracted from line 44 contained about 99% by weight of 1-butanol and about 100 ppm of phenol. The composition of the liquid extracted to storage tank 406 consisted of about 2% by weight of dibutyl carbonate and about 98% by weight of phenol.

[Purification of Diaryl Carbonate]

Figure 5:
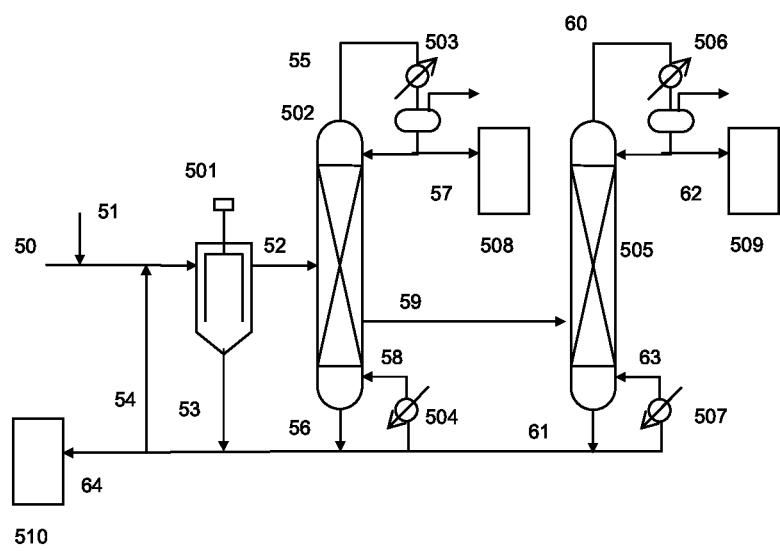
FIG. 5 is a conceptual drawing showing an isocyanate production apparatus according to an embodiment of the present invention.
Figure 6:
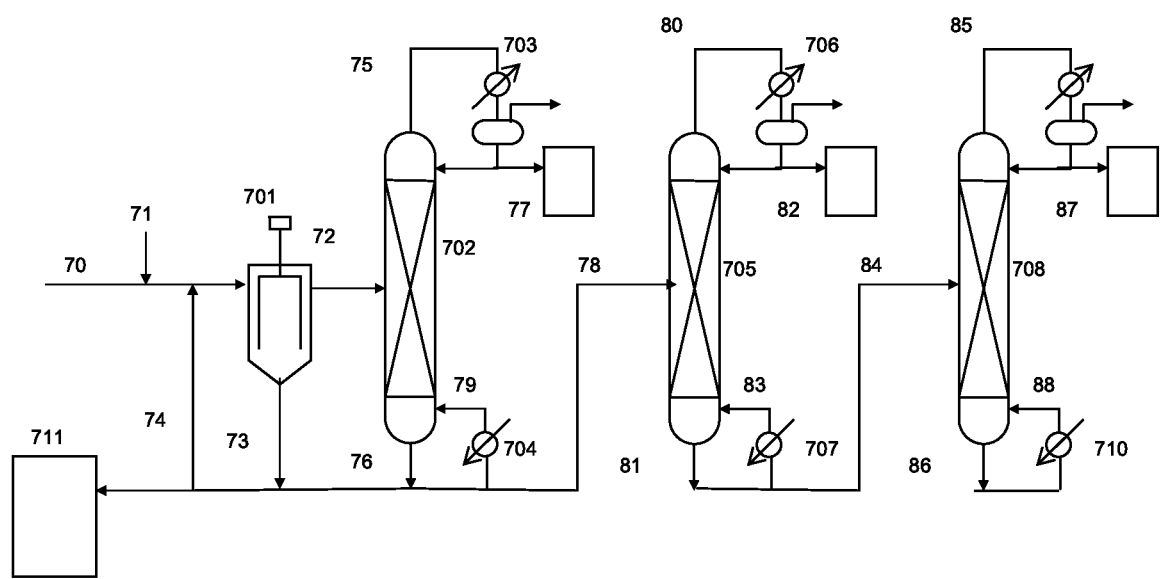
FIG. 6 is a conceptual drawing showing an isocyanate production apparatus according to an embodiment of the present invention.

Diaryl carbonate was purified using an apparatus like that shown in FIGS. 5 and 6.

Liquid extracted to storage tank 306 was continuously fed through preheater 501 to the middle stage of continuous multistage distillation column 502 packed with Dickson packing (diameter: 6 mm) and having an inner diameter of about 5 cm and column length of 2 m from line 51 at the rate of about 195 g/hr. The amount of heat required for distillative separation was supplied by circulating the liquid in the bottom of the column through line 53 and reboiler 504. The liquid temperature in the bottom of continuous multistage distillation column 502 was 210° C., the pressure at the top of the column was about 1.5 kPa, and the reflux ratio was set to be about 1. Gas distilled from the top of continuous multistage distillation column 502 was condensed in condenser 503 via line 52, and continuously extracted from line 54. Liquid was extracted from the bottom of the column through line 53 into storage tank 506 at the rate of about 14 g/hr.

The composition of the liquid extracted from line 54 contained about 0.3% by weight of dibutyl carbonate, about 34% by weight of butylphenyl carbonate and about 66% by weight of diphenyl carbonate.

Liquid extracted from line 54 was continuously fed through preheater 601 to the middle stage of continuous multistage distillation column 602 packed with Dickson packing (diameter: 6 mm) and having an inner diameter of 5 cm and column length of 2 m from line 61 at the rate of about 181 g/hr. The amount of heat required for distillative separation was supplied by circulating the liquid in the bottom of the column through line 63 and reboiler 604. The liquid temperature in the bottom of continuous multistage distillation column 602 was 232° C., the pressure at the top of the column was about 15 kPa, and the reflux ratio was set to be about 2. Gas distilled from the top of continuous multistage distillation column 602 was condensed in condenser 603 via line 62 and continuously extracted from line 64. Liquid was extracted from the bottom of the column through line 63 into storage tank 606 at the rate of about 119 g/hr.

The composition of the liquid extracted from line 64 contained about 0.6% by weight of dibutyl carbonate, about 99% by weight of butylphenyl carbonate and about 0.4% by weight of diphenyl carbonate. The composition of the liquid extracted to storage tank 606 contained about 0.1% by weight of butylphenyl carbonate and about 99.9% by weight of diphenyl carbonate. The diphenyl carbonate contained 8.2 ppm of a metal component in the form of iron.

Example 1

Step (1-1): Production of N,N'-hexanediyl-bis-carbamic Acid Bis(3-methylbutyl)Ester A reaction was carried out using an apparatus like that shown in FIG. 2.

3333 g (16.5 mol) of the bis(3-methylbutyl)carbonate of Reference Example 1 were supplied to a baffled reaction vessel 204 made of SUS and having an inner volume of 5 L from storage tank 201 via line 21 with line 24 closed, and 383.5 g (3.3 mol) of hexamethylene diamine (Aldrich Corp., USA) were supplied to the reaction vessel 204 from storage tank 202 via line 22. The liquid temperature inside the reaction vessel 204 was adjusted to be about 80° C., and 6.4 g of sodium methoxide (28% methanol solution, Wako Pure Chemical Industries, Ltd., Japan) were supplied to the SUS reaction vessel 204 from storage tank 203 via line 23 to carry out a reaction.

As a result of analyzing the solution following the reaction by liquid chromatography, N,N'-hexanediyl-bis-carbamic acid bis(3-methylbutyl)ester was found to have been formed at a yield of 99.7%.

Line 24 was opened and the reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (1-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of the continuous multistage distillation column 302 was condensed in condenser 303 via line 32 and continuously extracted into storage tank 305 from line 34 at the rate of about 43 g/hr. Liquid was continuously extracted from the bottom of the column through line 33 into storage tank 306 at the rate of about 237 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 237 g/hr. The amount of heat required for distillation was supplied by circulating the liquid in the bottom of the column through line 43 and reboiler 404. The liquid temperature in the bottom of continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 150 g/hr. Liquid was continuously extracted from the bottom of the column through line 43 into storage tank 406 at the rate of about 87 g/hr.

As a result of analyzing the mixture extracted into storage tank 406 by liquid chromatography, the mixture was found to contain about 98.2% by weight of N,N'-hexanediyl-bis-carbamic acid bis(3-methylbutyl)ester.

Step (1-3): Production of Isocyanate by Thermal Decomposition of N,N'-hexanediyl-bis-carbamic Acid Bis(3-methylbutyl)Ester A reaction was carried out using an apparatus like that shown in FIG. 5.

Thin film distillation apparatus 501 (Kobelco Eco-Solutions Co., Ltd., Japan) having a heat-conducting surface area of 0.1 m² was heated to 270° C. and the pressure within was set to to about 13 kPa. The mixture recovered into storage tank 406 in step (1-2) was heated to 160° C. and supplied to the top of thin film distillation apparatus 501 via line 50 at the rate of about 280 g/hr. In addition, dibutyl tin dilaurate (Wako Pure Chemical Industries, Ltd., Japan) was fed from line 51 at the rate of about 25.2 g/hr. A liquid phase component was extracted from the bottom of thin film distillation apparatus 501 via line 53, and circulated to the top of thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 150° C., and the pressure at the top of the column was about 50 kPa. Gas distilled from the top of the continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of continuous multistage distillation column 505 was 150° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 130 g/hr.

After operating for 40 hours, the liquid phase component was extracted into storage tank 510 from line 64 at the rate of about 11 g/hr.

The liquid extracted from line 62 was a solution that contained about 99.8% by weight of hexamethylene diisocyanate. The yield based on hexamethylene diamine was 96.7%.

Although continuous operation was carried out for 10 days, there was no accumulation of adhered substances observed on the walls of the thin film distillation apparatus 501.

Example 2

Step (2-1): Production of 3-((3-methylbutyloxy)carbonylamino-methyl-3,5,5-trimethylcyclohexylcarbamic Acid (3-methylbutyl)Ester A process was carried out in the same manner as step (1-1) of Example 1 with the exception of carrying out the reaction by supplying 3394 g (16.8 mol) of the bis(3-methylbutyl) carbonate of Reference Example 1, 596 g (3.5 mol) of 3-aminomethyl-3,5,5-trimethylcyclohexylamine (Aldrich Corp., USA) instead of hexamethylene diamine, and 6.8 g of sodium methoxide (28% methanol solution). As a result of analyzing the solution following the reaction by liquid chromatography, 3-((3-methylbutyloxy)carbonylamino-methyl-3,5,5-trimethylcyclohexylcarbamic acid (3-methylbutyl)ester was found to have been formed at a yield of 99.5%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (2-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of continuous multistage distillation column 302 was condensed in condenser 303 via line 32 and continuously extracted into storage tank 305 from line 34 at the rate of about 43 g/hr. Liquid was continuously extracted from the bottom of the column through line 33 into storage tank 306 at the rate of about 237 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 237 g/hr. The amount of heat required for distillation was supplied by circulating the liquid in the bottom of the column through line 43 and reboiler 404. The liquid temperature in the bottom of continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 138 g/hr. Liquid was continuously extracted from the bottom of the column through line 43 into storage tank 406 at the rate of about 98 g/hr.

As a result of analyzing the mixture extracted into storage tank 406 by liquid chromatography, the mixture was found to contain about 99.0% by weight of 3-((3-methylbutyloxy)carbonylamino-methyl-3,5,5-trimethylcyclohexylcarbamic acid (3-methylbutyl)ester.

Step (2-3): Production of Isocyanate by Thermal Decomposition of 3-((3-methylbutyloxy)carbonylamino-methyl-3,5,5-trimethylcyclohexylcarbamic Acid (3-methylbutyl)Ester A reaction was carried out using an apparatus like that shown in FIG. 5.

Thin film distillation apparatus 501 having a heat-conducting surface area of 0.1 m² was heated to 270° C. and the pressure within was set to be about 13 kPa. The mixture recovered into storage tank 406 in step (2-2) was heated to 170° C. and supplied to the top of thin film distillation apparatus 501 via line 50 at the rate of about 200 g/hr. In addition, dibutyl tin dilaurate (Wako Pure Chemical Industries, Ltd., Japan) was fed from line 51 at the rate of about 25.2 g/hr. A liquid phase component was extracted from the bottom of thin film distillation apparatus 501 via line 53, and circulated to the top of the thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 150° C., and the pressure at the top of the column was about 50 kPa. Gas distilled from the top of continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of continuous multistage distillation column 505 was 150° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 107 g/hr.

After operating for 40 hours, the liquid phase component was extracted into storage tank 510 from line 64 at the rate of about 9 g/hr.

The liquid extracted from line 62 was a solution that contained about 99.8% by weight of isophorone diisocyanate. The yield based on hexamethylene diamine was 96.5%.

Although continuous operation was carried out for 10 days, there was no accumulation of adhered substances observed on the walls of the thin film distillation apparatus 501.

Example 3

Step (3-1): Production of N,N'-(4,4'-methanediyl-diphenyl)-biscarbamic Acid Bis(3-methylbutyl)Ester Ferrous acetylacetonate was added to the bis(3-methylbutyl)carbonate of Reference Example 1 to prepare bis(3-methylbutyl)carbonate containing 7.4% of metal atoms in the form of iron. A process was carried out in the same manner as step (1-1) of Example 1 with the exception of carrying out the reaction by supplying 2917 g (14.4 mol) of the bis(3-methylbutyl)carbonate, 753 g (3.8 mol) of 4,4'-methylenedianiline (Aldrich Corp., USA) instead of hexamethylene diamine, and 7.3 g of sodium methoxide (28% methanol solution). As a result of analyzing the solution following the reaction by liquid chromatography, N,N'-(4,4'-methanediyl-diphenyl)-biscarbamic acid bis(3-methylbutyl)ester was found to have been formed at a yield of 99.1%. The reaction liquid was supplied to column 205 which packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (3-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 270 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of the continuous multistage distillation column 302 was condensed in condenser 303 via line 32 and continuously extracted into storage tank 305 from line 34 at the rate of about 48 g/hr. Liquid was continuously extracted from the bottom of the column through line 33 into storage tank 306 at the rate of about 222 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 237 g/hr. The amount of heat required for distillation was supplied by circulating the liquid in the bottom of the column through line 43 and reboiler 404. The liquid temperature in the bottom of continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 102 g/hr. Liquid was continuously extracted from the bottom of the column through line 43 into storage tank 406 at the rate of about 120 g/hr.

As a result of analyzing the mixture extracted into storage tank 406 by liquid chromatography, the mixture was found to contain about 98.5% by weight of N,N'-(4,4'-methanediyl-diphenyl)-biscarbamic acid bis(3-methylbutyl)ester.

Step (3-3): Production of Isocyanate by Thermal Decomposition of N,N'-(4,4'-methanediyl-diphenyl) biscarbamic Acid Bis(3-methylbutyl)Ester A reaction was carried out using an apparatus like that shown in FIG. 6.

Thin film distillation apparatus 701 having a heat-conducting surface area of 0.1 m$^2$ was heated to 270° C. and the pressure within was set to be about 1.3 kPa. The mixture recovered into storage tank 406 in step (3-2) was heated to 170° C. and supplied to the top of thin film distillation apparatus 701 via line 70 at the rate of about 190 g/hr. In addition, dibutyl tin dilaurate was fed from line 71 at the rate of about 14 g/hr. A liquid phase component was extracted from the bottom of thin film distillation apparatus 701 via line 73, and circulated to the top of thin film distillation apparatus 701 via line 74. A gaseous phase component was extracted from line 72.

The gaseous phase component extracted from thin film distillation apparatus 701 via line 72 was continuously fed to the middle stage of continuous multistage distillation column 702 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 76 and reboiler 704. The liquid temperature in the bottom of continuous multistage distillation column 702 was 200° C., and the pressure at the top of the column was 60 kPa. Gas distilled from the top of continuous multistage distillation column 702 was condensed in condenser 703 via line 75 and continuously extracted from line 77. A liquid phase component was extracted from line 78.

The liquid phase component extracted from line 78 was continuously fed to the middle stage of a continuous multistage distillation column 705 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 81 and reboiler 707. The liquid temperature in the bottom of continuous multistage distillation column 705 was 210° C., and the pressure at the top of the column was about 2.5 kPa. Gas distilled from the top of continuous multistage distillation column 705 was condensed in condenser 706 via line 80 and continuously extracted via line 82. A liquid component was extracted from line 84.

The liquid phase component extracted from line 84 was continuously fed to the middle stage of continuous multistage distillation column 708 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 86 and reboiler 710. The liquid temperature in the bottom of continuous multistage distillation column 708 was 220° C., and the pressure at the top of the column was about 0.5 kPa. Gas distilled from the top of continuous multistage distillation column 708 was condensed in condenser 709 via line 85 and continuously extracted via line 87 at the rate of about 105 g/hr. The liquid extracted from line 87 contained about 99.9% by weight of 4,4'-diphenylmethane diisocyanate. The yield based on 4,4'-methylenedianiline was 95.3%. Although continuous operation was carried out for 10 days, there was no accumulation of adhered substances observed on the walls of thin film distillation apparatus 701.

Example 4

Step (4-1): Production of Bis(3-methylbutyl)-4,4'-methylene-dicyclohexyl Carbamate A process was carried out in the same manner as step (1-1) of Example 1 with the exception of carrying out the reaction by supplying 3064 g (15.2 mol) of the bis(3-methylbutyl) carbonate of Reference Example 1, 778 g (3.7 mol) of 4,4'-methylenebis(cyclohexylamine) (Aldrich Corp., USA) instead of hexamethylene diamine, and 7.1 g of sodium methoxide (28% methanol solution). As a result of analyzing the solution following the reaction by liquid chromatography, bis(3-methylbutyl)-4,4'-methylene-dicyclohexyl carbamate was found to have been formed at a yield of 99.0%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (4-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 270 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of continuous multistage distillation column 302 was condensed in condenser 303 via line 32 and continuously extracted into storage tank 305 from line 34 at the rate of about 45 g/hr. Liquid was continuously extracted from the bottom of the column through line 33 into storage tank 306 at the rate of about 225 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 225 g/hr. The amount of heat required for distillation was supplied by circulating the liquid in the bottom of the column through line 43 and reboiler 404. The liquid temperature in the bottom of continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 111 g/hr. Liquid was continuously extracted from the bottom of the column through line 43 into storage tank 406 at the rate of about 114 g/hr.

As a result of analyzing the mixture extracted into storage tank 406 by liquid chromatography, the mixture was found to contain about 99.1% by weight of bis(3-methylbutyl)-4,4'-methylene-dicyclohexyl carbamate.

Step (4-3): Production of Isocyanate by Thermal Decomposition of N,N'-(4,4'-methanediyl-diphenyl) biscarbamic Acid Bis(3-methylbutyl)Ester A reaction was carried out using an apparatus like that shown in FIG. 6.

Thin film distillation apparatus 701 having a heat-conducting surface area of 0.1 m$^2$ was heated to 270° C. and the pressure within was set to about 1.3 kPa. The mixture recovered into storage tank 406 in step (4-2) was heated to 170° C. and supplied to the top of thin film distillation apparatus 701 via line 70 at the rate of about 200 g/hr. In addition, dibutyl tin dilaurate was fed from line 71 at the rate of about 14 g/hr. A liquid phase component was extracted from the bottom of thin film distillation apparatus 701 via line 73, and circulated to the top of the thin film distillation apparatus 701 via line 74. A gaseous phase component was extracted from line 72.

The gaseous phase component extracted from thin film distillation apparatus 701 via line 72 was continuously fed to the middle stage of continuous multistage distillation column 702 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 76 and reboiler 704. The liquid temperature in the bottom of continuous multistage distillation column 702 was 200° C., and the pressure at the top of the column was 60 kPa. Gas distilled from the top of continuous multistage distillation column 702 was condensed in condenser 703 via line 75 and continuously extracted from line 77. A liquid phase component was extracted from line 78.

The liquid phase component extracted from line 78 was continuously fed to the middle stage of continuous multistage distillation column 705 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 81 and reboiler 707. The liquid temperature in the bottom of continuous multistage distillation column 705 was 210° C., and the pressure at the top of the column was about 2.5 kPa. Gas distilled from the top of continuous multistage distillation column 705 was condensed in condenser 706 via line 80 and continuously extracted via line 82. A liquid component was extracted from line 84.

The liquid phase component extracted from line 84 was continuously fed to the middle stage of continuous multistage distillation column 708 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 86 and reboiler 710. The liquid temperature in the bottom of continuous multistage distillation column 708 was 220° C., and the pressure at the top of the column was about 0.5 kPa. Gas distilled from the top of continuous multistage distillation column 708 was condensed in condenser 709 via line 85 and continuously extracted via line 87 at the rate of about 105 g/hr. The liquid extracted from line 87 contained about 99.8% by weight of 4,4'-methylenebis(cyclohexylisocyanate). The yield based on 4,4'-methylenebis(cyclohexylamine) was 93.2%. Although continuous operation was carried out for 10 days, there was no accumulation of adhered substances observed on the walls of thin film distillation apparatus 701. When continuous operation was carried out for 30 days, accumulation of adhered substances was observed on the walls of thin film distillation apparatus 701.

Example 5

Step (5-1): Production of Toluene-2,4-dicarbamic Acid Bis(2-ethylbutyl)Ester

Bis(2-ethylbutyl)carbonate of Reference Example 3 was placed in pear-shaped flask having an internal volume of 10 L, a three-way valve, distillation column packed with Helipak No. 3, fractionating column equipped with a reflux condenser and coupled to a distillate collector, and thermometer were attached to the pear-shaped flask and the inside of the system was replaced with nitrogen in a vacuum to carry out distillative purification of the bis(2-ethylbutyl)carbonate. When $^1$H-NMR measurement was carried out on the distillative purification product, it was found to contain about 99.9% by weight of bis(2-ethylbutyl)carbonate. In addition, it also contained 0.003 ppm of metal atoms in the form of iron.

A process was carried out in the same manner as step (1-1) of Example 1 with the exception of carrying out the reaction by supplying 3589 g (15.6 mol) of the above bis(2-ethylbutyl) carbonate instead of bis(3-methylbutyl)carbonate, 464 g (3.8 mol) of 2,4-toluenediamine (Aldrich Corp., USA) instead of hexamethylene diamine, and 7.3 g of sodium methoxide (28% methanol solution). As a result of analyzing the solution following the reaction by liquid chromatography, toluene-2, 4-dicarbamic acid bis(2-ethylbutyl)ester was found to have been formed at a yield of 98.5%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (5-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 300 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 60 kPa. Gas distilled from the top of the continuous multistage distillation column 302 was condensed in condenser 303 via line 32 and continuously extracted into storage tank 305 from line 34 at the rate of about 56 g/hr. Liquid was continuously extracted from the bottom of the column through line 33 into storage tank 306 at the rate of about 244 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 244 g/hr. The amount of heat required for distillation was supplied by circulating the liquid in the bottom of the column through line 43 and reboiler 404. The liquid temperature in the bottom of the continuous multistage distillation column 402 was 160° C., and the pressure at the top of the column was about 0.7 kPa. Gas distilled from the top of continuous multistage distillation column 402 was condensed in condenser 403 via line 42 and continuously extracted into storage tank 405 from line 44 at the rate of about 138 g/hr. Liquid was continuously extracted from the bottom of the column through line 43 into storage tank 406 at the rate of about 106 g/hr.

As a result of analyzing the mixture extracted into storage tank 406 by liquid chromatography, the mixture was found to contain about 98.9% by weight of toluene-2,4-dicarbamic acid bis(2-ethylbutyl)ester.

Step (5-3): Production of Isocyanate by Thermal Decomposition of Toluene-2,4-dicarbamic Acid Bis(2-ethylbutyl)Ester A reaction was carried out using an apparatus like that shown in FIG. 5.

Thin film distillation apparatus 501 having a heat-conducting surface area of 0.1 m² was heated to 270° C. and the pressure within was set to be about 13 kPa. The mixture recovered into storage tank 406 in step (5-2) was heated to 170° C. and supplied to the top of thin film distillation apparatus 501 via line 50 at the rate of about 190 g/hr. In addition, dibutyl tin dilaurate was fed from line 51 at the rate of about 15.7 g/hr. A liquid phase component was extracted from the bottom of thin film distillation apparatus 501 via line 53, and circulated to the top of the thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of the continuous multistage distillation column 502 was 160° C., and the pressure at the top of the column was about 50 kPa. Gas distilled from the top of the continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of the continuous multistage distillation column 505 was 160° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 83 g/hr.

After operating for 40 hours, the liquid phase component was extracted into storage tank 510 from line 64 at the rate of about 16 g/hr.

The liquid extracted from line 62 was a solution that contained about 99.8% by weight of 2,4-tolylene diisocyanate. The yield based on 2,4-toluenediamine was 94.7%.

Although continuous operation was carried out for 10 days, there was no accumulation of adhered substances observed on the walls of the thin film distillation apparatus 501.

Example 6

Step (6-1): Production of N,N'-hexanediyl-bis-carbamic Acid Bis(2-ethylbutyl)Ester A process was carried out in the same manner as step (1-1) of Example 1 with the exception of carrying out the reaction by supplying 3483 g (15.1 mol) of the bis(2-ethylbutyl)carbonate of Reference Example 3 instead of bis(3-methylbutyl) carbonate, a mixture of 418 g (3.6 mol) of hexamethylene diamine and 368 g (3.8 mol) of 2-ethyl-1-butanol instead of hexamethylene diamine, and 6.9 g of sodium methoxide (28% methanol solution). As a result of analyzing the solution following the reaction by liquid chromatography, N,N'-hexanediyl-bis-carbamic acid bis(2-ethylbutyl)ester was found to have been formed at a yield of 99.5%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (6-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 270 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 60 kPa. Gas distilled from the top of continuous multistage distillation column 302 was condensed in condenser 303 via line 32 and continuously extracted into storage tank 305 from line 34 at the rate of about 69 g/hr. Liquid was continuously extracted from the bottom of the column through line 33 into storage tank 306 at the rate of about 201 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 201 g/hr. The amount of heat required for distillation was supplied by circulating the liquid in the bottom of the column through line 43 and reboiler 404. The liquid temperature in the bottom of continuous multistage distillation column 402 was 160° C., and the pressure at the top of the column was about 0.7 kPa. Gas distilled from the top of the continuous multistage distillation column 402 was condensed in condenser 403 via line 42 and continuously extracted into storage tank 405 from line 44 at the rate of about 115 g/hr. Liquid was continuously extracted from the bottom of the column through line 43 into storage tank 406 at the rate of about 86 g/hr.

As a result of analyzing the mixture extracted into storage tank 406 by liquid chromatography, the mixture was found to contain about 98.3% by weight of N,N'-hexanediyl-bis-carbamic acid bis(2-ethylbutyl)ester.

Step (6-3): Production of Isocyanate by Thermal Decomposition of N,N'-hexanediyl-bis-carbamic Acid Bis(2-ethylbutyl)Ester A reaction was carried out using an apparatus like that shown in FIG. 5.

Thin film distillation apparatus 501 having a heat-conducting surface area of 0.1 m² was heated to 270° C. and the pressure within was set to be about 13 kPa. The mixture recovered into storage tank 406 in step (6-2) was heated to 170° C. and supplied to the top of thin film distillation apparatus 501 via line 50 at the rate of about 270 g/hr. In addition, dibutyl tin dilaurate was fed from line 51 at the rate of about 22.7 g/hr. A liquid phase component was extracted from the bottom of thin film distillation apparatus 501 via line 53, and circulated to the top of the thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of the continuous multistage distillation column 502 was 160° C., and the pressure at the top of the column was about 50 kPa. Gas distilled from the top of the continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of the continuous multistage distillation column 505 was 160° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 116 g/hr.

After operating for 40 hours, the liquid phase component was extracted into storage tank 510 from line 64 at the rate of about 22 g/hr.

The liquid extracted from line 62 was a solution that contained about 99.8% by weight of hexamethylene diisocyanate. The yield based on hexamethylene diamine was 95.5%.

Although continuous operation was carried out for 10 days, there was no accumulation of adhered substances observed on the walls of the thin film distillation apparatus 501.

Example 7

Step (7-1): Production of 3-(phenoxycarbonylaminomethyl)-3,5,5-trimethylcyclohexylcarbamic Acid Phenyl Ester A reaction was carried out using an apparatus like that shown in FIG. 7.

1992 g (9.3 mol) of the diphenyl carbonate of Reference Example 6 were supplied to baffled reaction vessel 724 made of SUS and having an inner volume of 5 L from storage tank 721 via line A1 with line A4 closed, and 1311 g (14.0 mol) of phenol were supplied to the reaction vessel made of SUS from storage tank 722 via line A2. The liquid temperature inside reaction vessel 724 was adjusted to be about 50° C., and 528 g (3.1 mol) of 3-aminomethyl-3,5,5-trimethylcyclohexylamine were supplied to reaction vessel 724 from storage tank 723 via line A3 at the rate of about 250 g/hr.

As a result of analyzing the solution following the reaction by liquid chromatography, 3-(phenoxycarbonylaminomethyl)-3,5,5-trimethylcyclohexylcarbamic acid phenyl ester was found to have been formed at a yield of 99.3%.

Line A4 was opened and the reaction liquid was transferred to storage tank 725 via line A4.

Step (7-2): Removal of Low Boiling Point Component

Phenol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 300 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 60 kPa. Gas distilled from the top of continuous multistage distillation column 302 was condensed in condenser 303 via line 32 and continuously extracted into storage tank 305 from line 34 at the rate of about 155 g/hr. Liquid was continuously extracted from the bottom of the column through line 33 into storage tank 306 at the rate of about 145 g/hr.

Carbonic acid ester was removed using an apparatus like that shown in FIG. 4.

The mixture recovered into storage tank 306 was continuously fed in a liquid state through preheater 401 to middle stage of continuous multistage distillation column 402 packed with Dickson packing (diameter: 6 mm) and having an inner diameter of about 5 cm and column length of 2 m from line 41 at the rate of about 145 g/hr. The amount of heat required for distillation was supplied by circulating the liquid in the bottom of the column through line 43 and reboiler 404. The liquid temperature in the bottom of continuous multistage distillation column 402 was 160° C., and the pressure at the top of the column was about 0.4 kPa. Gas distilled from the top of continuous multistage distillation column 402 was condensed in condenser 403 via line 42 and continuously extracted into storage tank 405 from line 44 at the rate of about 55 g/hr. Liquid was continuously extracted from the bottom of the column through line 43 into storage tank 406 at the rate of about 90 g/hr.

As a result of analyzing the mixture extracted into storage tank 406 by liquid chromatography, the mixture was found to contain about 99.1% by weight of 3-(phenoxycarbonylaminomethyl)-3,5,5-trimethylcyclohexylcarbamic acid phenyl ester.

Step (7-3): Production of Isocyanate by Thermal Decomposition of 3-(phenoxycarbonylaminomethyl)-3,5,5-trimethylcyclohexylcarbamic Acid Phenyl Ester A reaction was carried out using an apparatus like that shown in FIG. 5.

Thin film distillation apparatus 501 having a heat-conducting surface area of 0.1 m² was heated to 220° C. and the pressure within was set to about 13 kPa. The mixture recovered into storage tank 406 in step (7-2) was heated to 170° C. and supplied to the top of thin film distillation apparatus 501 via line 50 at the rate of about 300 g/hr. A liquid phase component was extracted from the bottom of thin film distillation apparatus 501 via line 53, and circulated to the top of the thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 150° C., and the pressure at the top of the column was about 15 kPa. Gas distilled from the top of continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of continuous multistage distillation column 505 was 150° C., and the pressure at the top of the column was about 1.3 kPa. Gas distilled from the top of continuous multistage distillation column 505 was condensed in condenser 506 via line 60 and continuously extracted into storage tank 509 via line 62 at the rate of about 135 g/hr.

The liquid extracted from line 92 was a solution that contained about 99.8% by weight of isophorone diisocyanate. The yield based on 3-aminomethyl-3,5,5-trimethylcyclohexylamine was 95.3%. Although continuous operation was carried out for 10 days, there was no accumulation of adhered substances observed on the walls of the film distillation apparatus 501.

Example 8

Step (8-1): Production of N,N'-hexanediyl-bis-carbamic Acid Di(n-heptyl)Ester

A process was carried out in the same manner as step (1-1) of Example 1 with the exception of carrying out the reaction by supplying 3445 g (13.3 mol) of the diheptyl carbonate of Reference Example 4 instead of bis(3-methylbutyl)carbonate, 360 g (3.1 mol) of hexamethylene diamine and 6.0 g of sodium methoxide (28% methanol solution). As a result of analyzing the solution following the reaction by liquid chromatography, N,N'-hexanediyl-bis-carbamic acid di(n-heptyl) ester was found to have been formed at a yield of 98.9%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (8-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 13 kPa. Gas distilled from the top of continuous multistage distillation column 302 was condensed in condenser 303 via line 32 and continuously extracted into storage tank 305 from line 34 at the rate of about 52 g/hr. Liquid was continuously extracted from the bottom of the column through line 33 into storage tank 306 at the rate of about 228 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 228 g/hr. The amount of heat required for distillation was supplied by circulating the liquid in the bottom of the column through line 43 and reboiler 404. The liquid temperature in the bottom of continuous multistage distillation column 402 was 170° C., and the pressure at the top of the column was about 0.13 kPa. Gas distilled from the top of continuous multistage distillation column 402 was condensed in condenser 403 via line 42 and continuously extracted into storage tank 405 from line 44 at the rate of about 136 g/hr. Liquid was continuously extracted from the bottom of the column through line 43 into storage tank 406 at the rate of about 92 g/hr.

As a result of analyzing the mixture extracted into storage tank 406 by liquid chromatography, the mixture was found to contain about 98.6% by weight of N,N'-hexanediyl-bis-carbamic acid di(n-heptyl)ester.

Step (8-3): Production of Isocyanate by Thermal Decomposition of N,N'-hexanediyl-bis-carbamic Acid Di(n-heptyl)Ester A reaction was carried out using an apparatus like that shown in FIG. 5.

Thin film distillation apparatus 501 having a heat-conducting surface area of 0.1 m$^2$ was heated to 270° C. and the pressure within was set to be about 13 kPa. The mixture recovered into storage tank 406 in step (8-2) was heated to 170° C. and supplied to the top of thin film distillation apparatus 501 via line 50 at the rate of about 270 g/hr. In addition, dibutyl tin dilaurate was fed from line 51 at the rate of about 19.6 g/hr. A liquid phase component was extracted from the bottom of thin film distillation apparatus 501 via line 53, and circulated to the top of the thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 160° C., and the pressure at the top of the column was about 50 kPa. Gas distilled from the top of continuous multistage distillation column 502 was condensed in condenser 503 via line 55 and continuously extracted from line 57. A liquid phase component was extracted from line 59 of continuous multistage distillation column 502 at a location lower than line 52.

A gaseous phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 61 and reboiler 507. The liquid temperature in the bottom of continuous multistage distillation column 505 was 160° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 107 g/hr.

After operating for 40 hours, the liquid phase component was extracted into storage tank 510 from line 64 at the rate of about 21 g/hr.

The liquid extracted from line 62 was a solution that contained about 99.8% by weight of hexamethylene diisocyanate. The yield based on hexamethylene diamine was 94.9%.

Although continuous operation was carried out for 10 days, there was no accumulation of adhered substances observed on the walls of the thin film distillation apparatus 501.

Example 9

Step (9-1): Production of N,N'-hexanediyl-bis-carbamic Acid Bis(3-methylbutyl)Ester A process was carried out in the same manner as step (1-1) of Example 1 with the exception of carrying out the reaction by supplying 2687 g (13.3 mol) of the bis(3-methylbutyl) carbonate of Reference Example 1, 407 g (3.5 mol) of hexamethylene diamine and 6.8 g of sodium methoxide (28% methanol solution). As a result of analyzing the solution following the reaction by liquid chromatography, N,N'-hexanediyl-bis-carbamic acid bis(3-methylbutyl)ester was found to have been formed at a yield of 99.5%.

After opening line 24, the reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (9-2): Removal of Low Boiling Point Component

A process was carried out in the same manner as step (1-2) of Example 1 with the exception of continuously feeding the mixture recovered into storage tank 206 in a liquid state through preheater 301 to the middle stage of continuous multistage distillation column 302 from line 31 at the rate of about 300 g/hr, continuously extracting a liquid phase component from the bottom of the column to storage tank 306 via line 33 at the rate of about 241 g/hr, and continuously feeding the mixture recovered into storage tank 306 in a liquid state through preheater 401 to the middle stage of continuous multistage distillation column 402 from line 41 at the rate of about 241 g/hr. Gas distilled from the top of continuous multistage distillation column 402 was condensed in condenser 403 via line 42 and continuously extracted into storage tank 405 from line 44 at the rate of about 123 g/hr. Liquid was continuously extracted from the bottom of the column through line 43 into storage tank 406 at the rate of about 118 g/hr.

As a result of analyzing the mixture extracted into storage tank 406 by liquid chromatography, the mixture was found to contain about 98.5% by weight of N,N'-hexanediyl-bis-carbamic acid bis(3-methylbutyl)ester.

Step (9-3): Production of Isocyanate by Thermal Decomposition of N,N'-hexanediyl-bis-carbamic Acid Bis(3-methylbutyl)Ester A reaction was carried out using an apparatus like that shown in FIG. 5.

Thin film distillation apparatus 501 (Kobelco Eco-Solutions Co., Ltd., Japan) having a heat-conducting surface area of 0.1 m² was heated to 270° C. and the pressure within was set to be about 13 kPa. A process was carried out in the same manner as step (1-3) of Example 1 with the exception of heating the mixture recovered into storage tank 406 in step (9-2) to 200° C., supplying to the top of thin film distillation apparatus 501 via line 50 at the rate of about 280 g/hr, and feeding dibutyl tin dilaurate from line 51 at the rate of about 25.3 g/hr. A liquid was extracted into storage tank 509 via line 62 at the rate of about 107 g/hr.

After operating for 40 hours, the liquid phase component was extracted into storage tank 510 from line 64 at the rate of about 82 g/hr.

The liquid extracted from line 62 was a solution that contained about 99.8% by weight of hexamethylene diisocyanate. The yield based on hexamethylene diamine was 79.6%.

Although continuous operation was carried out for 10 days, there was no accumulation of adhered substances observed on the walls of thin film distillation apparatus 501.

Example 10

Step (10-1): Production of Bis(3-methylbutyl)-4,4'-methylene-dicyclohexyl Carbamate A process was carried out in the same manner as step (1-1) of Example 1 with the exception of carrying out the reaction by supplying 3272 g (16.2 mol) of the bis(3-methylbutyl) carbonate of Reference Example 1, 757 g (3.6 mol) of 4,4'-methylenebis(cyclohexylamine) instead of hexamethylene diamine, and 6.9 g of sodium methoxide (28% methanol solution). As a result of analyzing the solution following the reaction by liquid chromatography, bis(3-methylbutyl)-4,4'-methylene-dicyclohexyl carbamate was found to have been formed at a yield of 98.9%. The reaction liquid was supplied to column 205 which was packed with an acidic ion exchange resin (Amberlyst-15, spherical, Rohm and Haas Co., USA) adjusted by removing the moisture and was warmed to 80° C. by an external jacket so as to neutralize the sodium methoxide. The solution was then transferred to storage tank 206 via line 25.

Step (10-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of continuous multistage distillation column 302 was condensed in condenser 303 via line 32 and continuously extracted into storage tank 305 from line 34 at the rate of about 44 g/hr. Liquid was continuously extracted from the bottom of the column through line 33 into storage tank 306 at the rate of about 236 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 236 g/hr. The amount of heat required for distillation was supplied by circulating the liquid in the bottom of the column through line 43 and reboiler 404. The liquid temperature in the bottom of continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 127 g/hr. Liquid was continuously extracted from the bottom of the column through line 43 into storage tank 406 at the rate of about 109 g/hr.

As a result of analyzing the mixture extracted into storage tank 406 by liquid chromatography, the mixture was found to contain about 99.0% by weight of bis(3-methylbutyl)-4,4'-methylene-dicyclohexyl carbamate.

Step (10-3): Production of Isocyanate by Thermal Decomposition of Bis(3-methylbutyl)-4,4'-methylene-dicyclohexyl Carbamate A reaction was carried out using an apparatus like that shown in FIG. 8.

The mixture recovered into storage tank 406 in step (10-2) was heated to 170° C. and fed to the middle stage of continuous multistage distillation column 801 packed with Dickson packing (diameter: 6 mm) and having an inner diameter of about 5 cm and column length of 2 m via line B0 at the rate of about 220 g/hr, while at the same time dibutyl tin dilaurate was fed from line B1 at the rate of 15.7 g/hr to carry out a thermal decomposition reaction. The amount of heat required for the thermal decomposition reaction was supplied by circulating the liquid in the bottom of the column through line B3 and reboiler 803. The liquid temperature in the bottom of continuous multistage distillation column 801 was 280° C., and the pressure at the top of the column was about 15 kPa. Gas distilled from the top of continuous multistage distillation column 801 was condensed in condenser 802 via line B2 and continuously extracted from line B4. A liquid phase component was recovered from the bottom of continuous multistage distillation column 801 via line B3.

A liquid phase component extracted via line B6 was continuously fed to the middle stage of continuous multistage distillation column 804 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line B8 and reboiler 806. The liquid temperature in the bottom of continuous multistage distillation column 804 was 220° C., and the pressure at the top of the column was about 5.2 kPa. Gas distilled from the top of continuous multistage distillation column 804 was condensed in condenser 805 via line B7 and continuously extracted from line B9. A liquid phase component was recovered from the bottom of continuous multistage distillation column 804 via line B8 and line B11.

The liquid phase component extracted from line B8 was continuously fed to the middle stage of continuous multistage distillation column 807 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line B14 and reboiler 809. The liquid temperature in the bottom of continuous multistage distillation column 807 was 220° C., and the pressure at the top of the column was about 0.40 kPa. Gas distilled from the top of continuous multistage distillation column 807 was condensed in condenser 808 via line B12 and continuously extracted via line B13. The extracted amount in the steady state was about 108 g/hr.

The liquid extracted from line B13 was a solution that contained about 99.8% by weight of 4,4'-methylene-bis(cyclohexylisocyanate). The yield based on 4,4'-methylenebis(cyclohexylamine) was 82.2%. When continuous operation was carried out for 10 days, accumulation of adhered substances was observed inside continuous multistage distillation column 801.

Example 11

Step (11-1): Production of N,N'-hexanediyl-bis-carbamic Acid Bis(2-ethylbutyl)Ester A process was carried out in the same manner as step (1-1) of Example 1 with the exception of carrying out the reaction by supplying 3547 g (15.4 mol) of the bis(2-ethylbutyl)carbonate of Reference Example 3 instead of bis(3-methylbutyl) carbonate, 407 g (3.5 mol) of hexamethylene diamine and 6.8 g of sodium methoxide (28% methanol solution). As a result of analyzing the solution following the reaction by liquid chromatography, N,N'-hexanediyl-bis-carbamic acid bis(2-ethylbutyl)ester was found to have been formed at a yield of 99.1%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (11-2): Production of Isocyanate by Thermal Decomposition of N,N'-hexanediyl-bis-carbamic Acid Bis(2-ethylbutyl)Ester A reaction was carried out using an apparatus like that shown in FIG. 5.

Thin film distillation apparatus 501 having a heat-conducting surface area of 0.1 m² was heated to 270° C. and the pressure within was set to be about 13 kPa. The mixture recovered into storage tank 206 in step (11-1) was heated to 170° C. and supplied to the top of thin film distillation apparatus 501 via line 50 at the rate of about 790 g/hr. In addition, dibutyl tin dilaurate was fed from line 51 at the rate of about 21.9 g/hr. A liquid phase component was extracted from the bottom of thin film distillation apparatus 501 via line 53, and circulated to the top of the thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 160° C., and the pressure at the top of the column was about 50 kPa. Gas distilled from the top of continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of continuous multistage distillation column 505 was 160° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 112 g/hr.

After operating for 40 hours, the liquid phase component was extracted into storage tank 510 from line 64 at the rate of about 182 g/hr.

The liquid extracted from line 62 was a solution that contained about 99.8% by weight of hexamethylene diisocyanate. The yield based on hexamethylene diamine was 88.2%.

Although continuous operation was carried out for 10 days, there was no accumulation of adhered substances observed on the walls of the thin film distillation apparatus 501.

Example 12

Step (12-1): Production of 3-((3-methylbutyloxy) carbonylamino-methyl-3,5,5-trimethylcyclohexylcarbamic Acid (3-methyl butyl)Ester A process was carried out in the same manner as step (1-1) of Example 1 with the exception of carrying out the reaction by supplying 3224 g (16.0 mol) of the bis(3-methylbutyl) carbonate of Reference Example 1, 647 g (3.8 mol) of 3-aminomethyl-3,5,5-trimethylcyclohexylamine instead of hexamethylene diamine, and 7.3 g of sodium methoxide (28% methanol solution). As a result of analyzing the solution following the reaction by liquid chromatography, 3-((3-methylbutyloxy)carbonylamino-methyl-3,5,5-trimethylcyclohexylcarbamic acid (3-methylbutyl)ester was found to have been formed at a yield of 98.8%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (12-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of continuous multistage distillation column 302 was condensed in condenser 303 via line 32 and continuously extracted into storage tank 305 from line 34 at the rate of about 48 g/hr. Liquid was continuously extracted from the bottom of the column through line 33 into storage tank 306 at the rate of about 232 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 237 g/hr. The amount of heat required for distillation was supplied by circulating the liquid in the bottom of the column through line 43 and reboiler 404. The liquid temperature in the bottom of the continuous multistage distillation column 402 was 200° C., and the pressure at the top of the column was about 7.9 kPa. Gas distilled from the top of the continuous multistage distillation column 402 was condensed in condenser 403 via line 42 and continuously extracted into storage tank 405 from line 44 at the rate of about 123 g/hr. Liquid was continuously extracted from the bottom of the column through line 43 into storage tank 406 at the rate of about 109 g/hr.

As a result of analyzing the mixture extracted into storage tank 406 by liquid chromatography, the mixture was found to contain about 84.0% by weight of 3-((3-methylbutyloxy)carbonylamino-methyl-3,5,5-trimethylcyclohexylcarbamic acid (3-methylbutyl)ester.

Step (12-3): Production of Isocyanate by Thermal Decomposition of 3-((3-methylbutyloxy)carbonylamino-methyl-3,5,5-trimethylcyclohexylcarbamic Acid (3-methylbutyl)Ester A reaction was carried out using an apparatus like that shown in FIG. 5.

Thin film distillation apparatus 501 having a heat-conducting surface area of 0.1 m² was heated to 270° C. and the pressure within was set to be about 13 kPa. The mixture recovered into storage tank 406 in step (12-2) was heated to 170° C. and supplied to the top of thin film distillation apparatus 501 via line 50 at the rate of about 200 g/hr. In addition, dibutyl tin dilaurate (Wako Pure Chemical Industries, Ltd., Japan) was fed from line 51 at the rate of about 25.2 g/hr. A liquid phase component was extracted from the bottom of thin film distillation apparatus 501 via line 53, and circulated to the top of the thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 150° C., and the pressure at the top of the column was about 50 kPa. Gas distilled from the top of continuous multistage distillation column 502 was condensed in condenser 503 via line 55 and continuously extracted from line 57. A gaseous phase component was extracted from line 59 of continuous multistage distillation column 502 at a location lower than line 52.

The gaseous phase component extracted from line 59 was continuously fed to middle stage of continuous multistage distillation column 505 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 61 and reboiler 507. The liquid temperature in the bottom of continuous multistage distillation column 505 was 150° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 90.0 g/hr.

After operating for 40 hours, a liquid phase component was extracted into storage tank 510 from line 64 at the rate of about 44 g/hr.

The liquid extracted from line 62 was a solution that contained about 99.8% by weight of isophorone diisocyanate. The yield based on hexamethylene diamine was 81.5%.

Although continuous operation was carried out for 10 days, there was no accumulation of adhered substances observed on the walls of the thin film distillation apparatus 501.

Example 13

Step (13-1): Production of N,N'-hexanediyl-bis-carbamic Acid Bis(2-ethylhexyl)Ester A process was carried out in the same manner as step (1-1) of Example 1 with the exception of carrying out the reaction by supplying 3609 g (12.6 mol) of the bis(2-ethylhexyl)carbonate of Reference Example 5 instead of bis(3-methylbutyl) carbonate, 349 g (3.0 mol) of hexamethylene diamine and 5.8 g of sodium methoxide (28% methanol solution). As a result of analyzing the solution following the reaction by liquid chromatography, N,N'-hexanediyl-bis-carbamic acid bis(2-ethylhexyl)ester was found to have been formed at a yield of 98.5%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (13-2): Removal of Low Boiling Point Component

Alcohol was removed using an apparatus like that shown in FIG. 3.

The mixture recovered into storage tank 206 was continuously fed in a liquid state through preheater 301 to middle stage of continuous multistage distillation column 302 packed with Dickson packing (diameter: 6 mm) and having an inner diameter of about 5 cm and column length of 2 m from line 31 at the rate of about 300 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 13 kPa. Gas distilled from the top of continuous multistage distillation column 302 was condensed in condenser 303 via line 32 and continuously extracted into storage tank 305 from line 34 at the rate of about 58 g/hr. Liquid was continuously extracted from the bottom of the column through line 33 into storage tank 306 at the rate of about 242 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 219 g/hr. The amount of heat required for distillation was supplied by circulating the liquid in the bottom of the column through line 43 and reboiler 404. The liquid temperature in the bottom of continuous multistage distillation column 402 was 210° C., and the pressure at the top of the column was about 0.13 kPa. Gas distilled from the top of continuous multistage distillation column 402 was condensed in condenser 403 via line 42 and continuously extracted into storage tank 405 from line 44 at the rate of about 145 g/hr. Liquid was continuously extracted from the bottom of the column through line 43 into storage tank 406 at the rate of about 98 g/hr.

As a result of analyzing the mixture extracted into storage tank 406 by liquid chromatography, the mixture was found to contain about 73.9% by weight of N,N'-hexanediyl-bis-carbamic acid bis(2-ethylhexyl)ester.

Step (13-3): Production of Isocyanate by Thermal Decomposition of N,N'-hexanediyl-bis-carbamic Acid Bis(2-ethylhexyl)Ester A reaction was carried out using an apparatus like that shown in FIG. 5.

Thin film distillation apparatus 501 having a heat-conducting surface area of 0.1 m² was heated to 270° C. and the pressure within was set to be about 13 kPa. The mixture recovered into storage tank 406 in step (13-2) was heated to 170° C. and supplied to the top of thin film distillation apparatus 501 via line 50 at the rate of about 270 g/hr. In addition, dibutyl tin dilaurate was fed from line 51 at the rate of about 22.7 g/hr. A liquid phase component was extracted from the bottom of thin film distillation apparatus 501 via line 53, and circulated to the top of the thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of the continuous multistage distillation column 502 was 160° C., and the pressure at the top of the column was about 50 kPa. Gas distilled from the top of the continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of the continuous multistage distillation column 505 was 160° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 75.1 g/hr.

After operating for 40 hours, the liquid phase component was extracted into storage tank 510 from line 64 at the rate of about 82 g/hr.

The liquid extracted from line 62 was a solution that contained about 99.8% by weight of hexamethylene diisocyanate. The yield based on hexamethylene diamine was 70.9%.

Although continuous operation was carried out for 10 days, there was no accumulation of adhered substances observed on the walls of the thin film distillation apparatus 501.

Example 14

Step (14-1): Production of N,N'-hexanediyl-bis-carbamic Acid Dibutyl Ester

A process was carried out in the same manner as step (1-1) of Example 1 with the exception of carrying out the reaction by supplying 3293 g (18.9 mol) of the dibutyl carbonate of Reference Example 2 instead of bis(3-methylbutyl)carbonate, 523 g (4.5 mol) of hexamethylene diamine and 8.7 g of sodium methoxide (28% methanol solution). As a result of analyzing the solution following the reaction by liquid chromatography, N,N'-hexanediyl-bis-carbamic acid di(n-butyl) ester was found to have been formed at a yield of 98.8%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (14-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 290 g/hr. The amount of heat required for distillation was supplied by circulating the liquid in the bottom of the column through line 33 and reboiler 304. The liquid temperature in the bottom of continuous multistage distillation column 302 was 150° C., and the pressure at the top of the column was about 70 kPa. Gas distilled from the top of continuous multistage distillation column 302 was condensed in condenser 303 via line 32 and continuously extracted into storage tank 305 from line 34 at the rate of about 50 g/hr. Liquid was continuously extracted from the bottom of the column through line 33 into storage tank 306 at the rate of about 240 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 240 g/hr. The amount of heat required for distillation was supplied by circulating the liquid in the bottom of the column through line 43 and reboiler 404. The liquid temperature in the bottom of continuous multistage distillation column 402 was 150° C., and the pressure at the top of the column was about 1.3 kPa. Gas distilled from the top of continuous multistage distillation column 402 was condensed in condenser 403 via line 42 and continuously extracted into storage tank 405 from line 44 at the rate of about 132 g/hr. Liquid was continuously extracted from the bottom of the column through line 43 into storage tank 406 at the rate of about 108 g/hr.

As a result of analyzing the mixture extracted into storage tank 406 by liquid chromatography, the mixture was found to contain about 98.5% by weight of N,N'-hexanediyl-bis-carbamic acid di(n-butyl)ester.

Step (14-3): Production of Isocyanate by Thermal Decomposition of N,N'-hexanediyl-bis-carbamic Acid Di(n-butyl)Ester A reaction was carried out using an apparatus like that shown in FIG. 5.

Thin film distillation apparatus 501 having a heat-conducting surface area of 0.1 m² was heated to 270° C. and the pressure within was set to be about 13 kPa. The mixture recovered into storage tank 406 in step (14-2) was heated to 170° C. and supplied to the top of thin film distillation apparatus 501 via line 50 at the rate of about 260 g/hr. In addition, dibutyl tin dilaurate was fed from line 51 at the rate of about 25.6 g/hr. A liquid phase component was extracted from the bottom of thin film distillation apparatus 501 via line 53, and circulated to the top of thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 160° C., and the pressure at the top of the column was about 50 kPa. Gas distilled from the top of continuous multistage distillation column 502 was condensed in condenser 503 via line 55 and continuously extracted from line 57. A gaseous phase component was extracted from line 59 of continuous multistage distillation column 502 at a location lower than line 52.

The gaseous phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 61 and reboiler 507. The liquid temperature in the bottom of continuous multistage distillation column 505 was 160° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 75.1 g/hr.

After operating for 40 hours, the liquid phase component was extracted into storage tank 510 from line 64 at the rate of about 104 g/hr.

The liquid extracted from line 62 was a solution that contained about 99.8% by weight of hexamethylene diisocyanate. The yield based on hexamethylene diamine was 75.1%.

When continuous operation was carried out for 48 hours, there was accumulation of adhered substances observed on the walls of the top and sides of thin film distillation apparatus 501.

Example 15

Step (15-1): Production of N,N'-hexanediyl-bis-carbamic Acid Bis(3-methylbutyl)Ester An apparatus was used like that shown in FIG. 10.

A mixture of 639 g (5.5 mol) of hexamethylene diamine and 64 g of water was supplied to baffled reaction vessel 1004 made of SUS and having an inner volume of 5 L from storage tank 1001 via line D1 with line D4 closed. The liquid temperature inside reaction vessel 1004 was adjusted to be about 80° C., and the pressure inside reaction vessel 1004 was reduced to 30 kPa to distill off the water. The water was condensed in condenser 1007 and extracted via line D6.

3333 g (16.5 mol) of the bis(3-methylbutyl)carbonate of Reference Example 1 were supplied from storage tank 1002 to reaction vessel 1004 via line D2, and the liquid temperature inside reaction vessel 1004 was adjusted to about 80° C. 6.4 g of sodium methoxide (28% methanol solution, Wako Pure Chemical Industries, Ltd., Japan) were supplied from storage tank 1003 to SUS reaction vessel 1004 via line D3 to carry out a reaction.

As a result of analyzing the solution following the reaction by liquid chromatography, N,N'-hexanediyl-bis-carbamic acid bis(3-methylbutyl)ester was found to have been formed at a yield of 99.7%.

After opening line D4, the reaction liquid was supplied to column 1005 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 1006 via line D5.

Step (15-2): Removal of Low Boiling Point Component

Alcohol was removed using an apparatus like that shown in FIG. 3.

The mixture recovered into storage tank 1006 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of continuous multistage distillation column 302 was condensed in condenser 303 via line 32 and continuously extracted into storage tank 305 from line 34 at the rate of about 67 g/hr. Liquid was continuously extracted from the bottom of the column through line 33 into storage tank 306 at the rate of about 213 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 213 g/hr. The amount of heat required for distillation was supplied by circulating the liquid in the bottom of the column through line 43 and reboiler 404. The liquid temperature in the bottom of the continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 78 g/hr. Liquid was continuously extracted from the bottom of the column through line 43 into storage tank 406 at the rate of about 135 g/hr.

As a result of analyzing the mixture extracted into storage tank 406 by liquid chromatography, the mixture was found to contain about 98.2% by weight of N,N'-hexanediyl-bis-carbamic acid bis(3-methylbutyl)ester.

Step (15-3): Production of Isocyanate by Thermal Decomposition of N,N'-hexanediyl-bis-carbamic Acid Bis(3-methylbutyl)Ester A reaction was carried out using an apparatus like that shown in FIG. 5.

Thin film distillation apparatus 501 (Kobelco Eco-Solutions Co., Ltd., Japan) having a heat-conducting surface area of 0.1 m$^2$ was heated to 270° C. and the pressure within was set to be about 13 kPa. The mixture recovered into storage tank 406 in step (15-2) was heated to 160° C. and supplied to the top of thin film distillation apparatus 501 via line 50 at the rate of about 280 g/hr. In addition, dibutyl tin dilaurate (Wako Pure Chemical Industries, Ltd., Japan) was fed from line 51 at the rate of about 25.2 g/hr. A liquid phase component was extracted from the bottom of thin film distillation apparatus 501 via line 53, and circulated to the top of thin film distillation apparatus 501 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 150° C., and the pressure at the top of the column was about 50 kPa. Gas distilled from the top of continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of continuous multistage distillation column 505 was 150° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 131 g/hr.

After operating for 40 hours, the liquid phase component was extracted into storage tank 510 from line 64 at the rate of about 11 g/hr.

The liquid extracted from line 62 was a solution that contained about 99.8% by weight of hexamethylene diisocyanate. The yield based on hexamethylene diamine was 97.2%.

Although continuous operation was carried out for 10 days, there was no accumulation of adhered substances observed on the walls of thin film distillation apparatus 501.

Example 16

Step (16-1): Production of N,N'-hexanediyl-bis-carbamic Acid Bis(3-methylbutyl)Ester Bis(3-methylbutyl)carbonate of Reference Example 1 was placed in pear-shaped flask having an internal volume of 10 L, a three-way valve, distillation column packed with Helipak No. 3, fractionating column equipped with a reflux condenser and coupled to a distillate collector, and thermometer were attached to the pear-shaped flask and the inside of the system was replaced with nitrogen in a vacuum to carry out distillative purification of the bis(3-methylbutyl)carbonate. The flask was cooled to terminate distillative purification when distillate equal to about two-thirds the charged amount was obtained. When $^1$H-NMR measurement was carried out on the distillative purification product, it was found to contain about 99.9% by weight of bis(3-methylbutyl)carbonate. In addition, metal atoms in the form of iron, cobalt, nickel, zinc, tin, copper and titanium contained in the distillate were below the detection limit (0.001 ppm).

A process was carried out in the same manner as step (1-1) of Example 1 with the exception of carrying out the reaction by supplying 3535 g (17.5 mol) of the recovered distillate in the form of bis(3-methylbutyl)carbonate, 407 g (3.5 mol) of hexamethylene diamine, and 6.8 g of sodium methoxide (28% methanol solution). As a result of analyzing the solution following the reaction by liquid chromatography, N,N'-hexanediyl-bis carbamic acid bis(3-methylbutyl)ester was found to have been formed at a yield of 94.0%.

Line 24 was opened and the reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (16-2): Removal of Low Boiling Point Component

A process was carried out in the same manner as step (1-2) of Example 1 with the exception of continuously feeding the mixture recovered into storage tank 206 in a liquid state through preheater 301 to the middle stage of continuous multistage distillation column 302 from line 31 at the rate of about 280 g/hr, continuously extracting a liquid phase component from the bottom of the column to storage tank 306 via line 33 at the rate of about 239 g/hr, and continuously feeding the mixture recovered into storage tank 306 in a liquid state through preheater 401 to the middle stage of continuous multistage distillation column 402 from line 41 at the rate of about 239 g/hr. Gas distilled from the top of the continuous multistage distillation column 402 was condensed in condenser 403 via line 42 and continuously extracted into storage tank 405 from line 44 at the rate of about 157 g/hr. Liquid was continuously extracted from the bottom of the column through line 43 into storage tank 406 at the rate of about 82 g/hr.

As a result of analyzing the mixture extracted into storage tank 406 by liquid chromatography, the mixture was found to contain about 98.4% by weight of N,N'-hexanediyl-bis-carbamic acid bis(3-methylbutyl)ester.

Step (16-3): Production of Isocyanate by Thermal Decomposition of N,N'-hexanediyl-bis-carbamic Acid Bis(3-methylbutyl)Ester A reaction was carried out using an apparatus like that shown in FIG. 5.

Thin film distillation apparatus 501 (Kobelco Eco-Solutions Co., Ltd., Japan) having a heat-conducting surface area of 0.1 m$^2$ was heated to 270° C. and the pressure within was set to be about 13 kPa. A process was carried out in the same manner as step (1-3) of Example 1 with the exception of heating the mixture recovered into storage tank 406 in step (16-2) to 200° C., supplying to the top of thin film distillation apparatus 501 via line 50 at the rate of about 280 g/hr, and feeding dibutyl tin dilaurate from line 51 at the rate of about 25.3 g/hr. A liquid was extracted into storage tank 509 via line 62 at the rate of about 131 g/hr.

After operating for 40 hours, the liquid phase component was extracted into storage tank 510 from line 64 at the rate of about 77 g/hr.

The liquid extracted from line 62 was a solution that contained about 99.8% by weight of hexamethylene diisocyanate. The yield based on hexamethylene diamine was 91.7%.

Although continuous operation was carried out for 10 days, there was no accumulation of adhered substances observed on the walls of thin film distillation apparatus 501.

Example 17

Step (17-1): Production of N,N'-hexanediyl-bis-carbamic Acid Bis(3-methylbutyl)Ester Ferrous acetylacetonate was added to the bis(3-methylbutyl)carbonate of Reference Example 1 to prepare bis(3-methylbutyl)carbonate having a metal atom content in the form of iron of 11%. The same process as that of step (1-1) of Example 1 was carried out with the exception of supplying 3434 g (17.0 mol) of the bis(3-methylbutyl)carbonate, 395 g (3.5 mol) of hexamethylene diamine and 6.6 g of sodium methoxide (28% methanol solution). As a result of analyzing the solution following the reaction by liquid chromatography, N,N'-hexanediyl-bis-carbamic acid bis(3-methylbutyl)ester was found to have been formed at a yield of 92.0%.

Line 24 was opened and the reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (17-2): Removal of Low Boiling Point Component

A process was carried out in the same manner as step (1-2) of Example 1 with the exception of continuously feeding the mixture recovered into storage tank 206 in a liquid state through preheater 301 to the middle stage of continuous multistage distillation column 302 from line 31 at the rate of about 280 g/hr, continuously extracting a liquid phase component from the bottom of the column to storage tank 306 via line 33 at the rate of about 240 g/hr, and continuously feeding the mixture recovered into storage tank 306 in a liquid state through preheater 401 to the middle stage of continuous multistage distillation column 402 from line 41 at the rate of about 240 g/hr. Gas distilled from the top of continuous multistage distillation column 402 was condensed in condenser 403 via line 42 and continuously extracted into storage tank 405 from line 44 at the rate of about 160 g/hr. Liquid was continuously extracted from the bottom of the column through line 43 into storage tank 406 at the rate of about 80 g/hr.

As a result of analyzing the mixture extracted into storage tank 406 by liquid chromatography, the mixture was found to contain about 98.1% by weight of N,N'-hexanediyl-bis-carbamic acid bis(3-methylbutyl)ester.

Step (17-3): Production of Isocyanate by Thermal Decomposition of N,N'-hexanediyl-bis-carbamic Acid Bis(3-methylbutyl)Ester A reaction was carried out using an apparatus like that shown in FIG. 5.

Thin film distillation apparatus 501 (Kobelco Eco-Solutions Co., Ltd., Japan) having a heat-conducting surface area of 0.1 m$^2$ was heated to 270° C. and the pressure within was set to be about 13 kPa. A process was carried out in the same manner as step (1-3) of Example 1 with the exception of heating the mixture recovered into storage tank 406 in step (17-2) to 200° C., supplying to the top of thin film distillation apparatus 501 via line 50 at the rate of about 280 g/hr, and feeding dibutyl tin dilaurate from line 51 at the rate of about 25.2 g/hr. A liquid was extracted into storage tank 509 via line 62 at the rate of about 127 g/hr.

After operating for 40 hours, the liquid phase component was extracted into storage tank 510 from line 64 at the rate of about 85 g/hr.

The liquid extracted from line 62 was a solution that contained about 99.8% by weight of hexamethylene diisocyanate. The yield based on hexamethylene diamine was 87.5%.

Although continuous operation was carried out for 10 days, there was no accumulation of adhered substances observed on the walls of thin film distillation apparatus 501.

Example 18

Step (18-1): Production of N,N'-hexanediyl-bis-carbamic Acid Bis(3-methylbutyl)Ester The same process as that of step (1-1) of Example 1 was carried out with the exception of supplying 2969 g (14.7 mol) of the bis(3-methylbutyl)carbonate of Reference Example 1, 488 g (4.2 mol) of hexamethylene diamine and 8.1 g of sodium methoxide (28% methanol solution). As a result of analyzing the solution following the reaction by liquid chromatography, N,N'-hexanediyl-bis-carbamic acid bis(3-methylbutyl)ester was found to have been formed at a yield of 99.1%.

Line 24 was opened and the reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (18-2): Removal of Low Boiling Point Component

A process was carried out in the same manner as step (1-2) of Example 1 with the exception of continuously feeding the mixture recovered into storage tank 206 in a liquid state through preheater 301 to middle stage of continuous multistage distillation column 302 from line 31 at the rate of about 300 g/hr, continuously extracting a liquid phase component from the bottom of the column to storage tank 306 via line 33 at the rate of about 221 g/hr, and continuously feeding the mixture recovered into storage tank 306 in a liquid state through preheater 401 to the middle stage of continuous multistage distillation column 402 from line 41 at the rate of about 221 g/hr. Gas distilled from the top of continuous multistage distillation column 402 was condensed in condenser 403 via line 42 and continuously extracted into storage tank 405 from line 44 at the rate of about 104 g/hr. Liquid was continuously extracted from the bottom of the column through line 43 into storage tank 406 at the rate of about 117 g/hr.

As a result of analyzing the mixture extracted into storage tank 406 by liquid chromatography, the mixture was found to contain about 98.7% by weight of N,N'-hexanediyl-bis-carbamic acid bis(3-methylbutyl)ester.

Step (18-3): Production of Isocyanate by Thermal Decomposition of N,N'-hexanediyl-bis-carbamic Acid Diphenyl Ester A reaction was carried out using an apparatus like that shown in FIG. 11.

Reaction vessel 1104 made of SUS and having the same shape as SUS reaction vessel 202 of FIG. 2 was heated to 270° C. and the pressure within was set to be about 13 kPa. The N,N'-hexanediyl-bis-carbamic acid bis(3-methylbutyl)ester extracted into storage tank 406 in step (18-2) was supplied to reaction vessel 1104 at the rate of 280 g/hr, and dibutyl tin dilaurate was simultaneously supplied from storage tank via line E2 to reaction vessel 1104 at the rate of 25.3 g/hr. A gaseous phase component was extracted from line E4, and the gaseous phase component was continuously fed to the middle stage of continuous multistage distillation column 1105 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line E6 and reboiler 1108. The liquid temperature in the bottom of continuous multistage distillation column 1105 was 150° C., and the pressure at the top of the column was about 15 kPa. Gas distilled from the top of continuous multistage distillation column 1102 was condensed in condenser 1107 via line E5 and continuously extracted from line E7. A liquid phase component was extracted from line E9 of continuous multistage distillation column 1105 at a location lower than line E4.

The liquid phase component extracted from line E9 was continuously fed to the middle stage of continuous multistage distillation column 1106 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line E11 and reboiler 1112. The liquid temperature in the bottom of continuous multistage distillation column 1106 was 150° C., and the pressure at the top of the column was about 1.5 kPa. Gas distilled from the top of continuous multistage distillation column 1106 was condensed in condenser 1110 via line E10 and continuously extracted into storage tank 1111 via line E12 at the rate of about 88 g/hr. The liquid recovered into storage tank 1111 was a solution that contained about 99.8% by weight of hexanediyl diisocyanate. The yield based on hexamethylene diamine was 64.4%.

When continuous operation was carried out for 10 hours, there was accumulation of adhered substances observed on the walls of reaction vessel 1104.

Example 19

Cleaning of Reaction Vessel

A cleaning procedure was carried out on thin film distillation apparatus 701 in which accumulation of adhered substance was observed in Example 4. Thin film distillation apparatus 701 was heated to 180° C. and the inside of thin film distillation apparatus 701 was replaced with a nitrogen atmosphere at atmospheric pressure. Phenol was supplied from line 70 at the rate of about 1200 g/hr, extracted from line 83 and a liquid phase component was recovered from line 89 into storage tank 711. When this procedure was carried out for 1 hour, adhered substance was not observed on the inside of thin film distillation apparatus 701.

Examples 20 to 27

The procedure of Example 4 was carried out continuously and various cleaning solvents were used every 30 days to carry out the cleaning procedure using the same method as Example 19. Those results are shown in Table 1.

Comparative Example 1

Step (A-1): Production of N,N'-hexanediyl-bis-carbamic Acid Bis(3-methylbutyl)Ester A reaction was carried out using an apparatus like that shown in FIG. 9.

2909 g (14.4 mol) of bis(3-methylbutyl)carbonate of Reference Example 1 were supplied to baffled reaction vessel 904 made of SUS and having an inner volume of 5 L from storage tank 901 via line C1 with lines C4 and C6 closed, and 349 g (3.0 mol) of hexamethylene diamine were supplied to reaction vessel 904 from storage tank 902 via line C2. The liquid temperature inside reaction vessel 904 was adjusted to about 80° C., and 8.7 g of sodium methoxide (28% methanol solution) were supplied to reaction vessel 904 made of SUS from storage tank 903 via line C3 to carry out a reaction.

As a result of analyzing the solution following the reaction by liquid chromatography, N,N'-hexanediyl-bis-carbamic acid bis(3-methylbutyl)ester was found to have been formed at a yield of 99.0%.

Line C4 was opened and the reaction liquid was supplied to column 905 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 906 via line C5.

Step (A-2): Removal of Low Boiling Point Component

Alcohol was removed using an apparatus like that shown in FIG. 3.

The mixture recovered into storage tank 906 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for the reaction and distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of continuous multistage distillation column 302 was condensed in condenser 303 via line 32 and continuously extracted into storage tank 305 from line 34 at the rate of about 44 g/hr. Liquid was continuously extracted from the bottom of the column through line 33 into storage tank 306 at the rate of about 236 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 236 g/hr. The amount of heat required for the reaction and distillation was supplied by circulating the liquid in the bottom of the column through line 43 and reboiler 404. The liquid temperature in the bottom of continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 146 g/hr. Liquid was continuously extracted from the bottom of the column through line 43 into storage tank 406 at the rate of about 90 g/hr.

As a result of analyzing the mixture extracted into storage tank 406 by liquid chromatography, the mixture was found to contain about 97.6% by weight of N,N'-hexanediyl-bis-carbamic acid bis(3-methylbutyl)ester.

Step (A-3): Production of Isocyanate by Thermal Decomposition of N,N'-hexanediyl-bis-carbamic Acid Bis(3-methylbutyl)Ester A reaction was carried out using an apparatus like that shown in FIG. 5.

After closing line 54, thin film distillation apparatus 501 (Kobelco Eco-Solutions Co., Ltd., Japan) having a heat-conducting surface area of 0.1 m$^2$ was heated to 270° C. and the pressure within was set to be about 13 kPa. The mixture recovered into storage tank 406 in step (A-2) was heated to 160° C. and supplied to the top of thin film distillation apparatus 501 via line 50 at the rate of about 280 g/hr. In addition, dibutyl tin dilaurate (Wako Pure Chemical Industries, Ltd., Japan) was fed from line 51 at the rate of about 25.1 g/hr. A liquid phase component was extracted from the bottom of thin film distillation apparatus 501 via line 53, and recovered in storage tank 510 via line 54. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 150° C., and the pressure at the top of the column was about 50 kPa. Gas distilled from the top of continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of continuous multistage distillation column 505 was 150° C., and the pressure at the top of the column was about 1.5 kPa. Gas distilled from the top of the continuous multistage distillation column 505 was condensed in condenser 506 via line 60 and continuously extracted into storage tank 509 via line 62.

Step (A-4): Continuous Production of Carbamic Acid Ester

Figure 9:
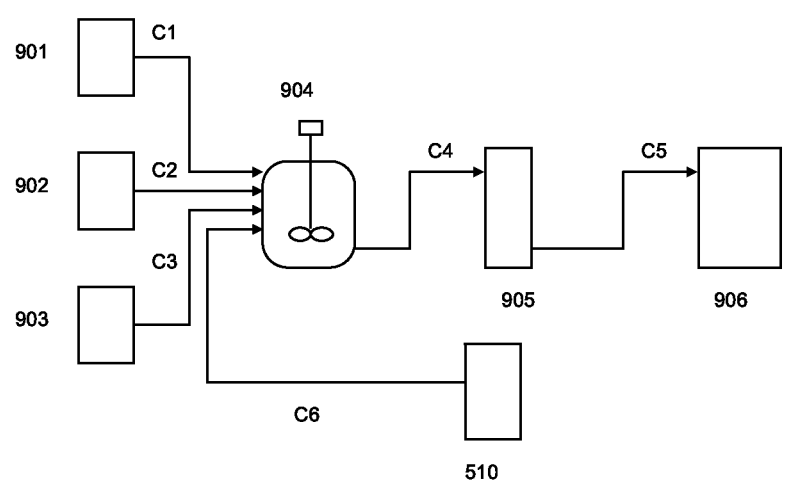
FIG. 9 is a conceptual drawing showing a carbamic acid ester production apparatus according to an embodiment of the present invention.

Production of carbamic acid ester was continuously carried out using an apparatus like that shown in FIG. 9.

About 220 g of the mixture extracted from storage tank 510 were supplied to reaction vessel 904 via line C5 with line C4 closed, 2909 g (14.4 mol) of bis(3-methylbutyl)carbonate were supplied to baffled reaction vessel 904 made of SUS and having an inner volume of 5 L from storage tank 901 via line C1, and 349 g (3.0 mol) of hexamethylene diamine were supplied to the reaction vessel 904 from storage tank 902 via line C2. The liquid temperature inside the reaction vessel 904 was adjusted to about 80° C., and 8.7 g of sodium methoxide (28% methanol solution) were supplied to reaction vessel 904 made of SUS from storage tank 903 via line C3 to carry out a reaction. As a result of analyzing the solution following the reaction by liquid chromatography, N,N'-hexanediyl-bis-carbamic acid bis(3-methylbutyl)ester was found to have been formed at a yield of 92.0% based on the supplied hexamethylene diamine.

Line C4 was opened and the reaction liquid was supplied to column 905 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 906 via line C5.

Step (A-5): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for the reaction and distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of continuous multistage distillation column 302 was condensed in condenser 303 via line 32 and continuously extracted into storage tank 305 from line 34 at the rate of about 39 g/hr. Liquid was continuously extracted from the bottom of the column through line 33 into storage tank 306 at the rate of about 241 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 241 g/hr. The amount of heat required for the reaction and distillation was supplied by circulating the liquid in the bottom of the column through line 43 and reboiler 404. The liquid temperature in the bottom of continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 144 g/hr. Liquid was continuously extracted from the bottom of the column through line 43 into storage tank 406 at the rate of about 97 g/hr.

As a result of analyzing the mixture extracted into storage tank 406 by liquid chromatography, the mixture was found to contain about 94.3% by weight of N,N'-hexanediyl-bis-carbamic acid bis(3-methylbutyl)ester.

Step (A-6): Production of Isocyanate by Thermal Decomposition of N,N'-hexanediyl-bis-carbamic Acid Bis(3-methylbutyl)Ester A reaction was carried out using an apparatus like that shown in FIG. 5.

After closing line 54, thin film distillation apparatus 501 having a heat-conducting surface area of 0.1 m² was heated to 270° C. and the pressure within was set to be about 13 kPa. The mixture recovered into storage tank 406 in step (A-5) was heated to 160° C. and supplied to the top of thin film distillation apparatus 501 via line 50 at the rate of about 280 g/hr. In addition, dibutyl tin dilaurate was fed from line 51 at the rate of about 24.2 g/hr. A liquid phase component was extracted from the bottom of thin film distillation apparatus 501 via line 53, and recovered in storage tank 510 via line 64. A gaseous phase component was extracted from line 52.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of the continuous multistage distillation column 502 was 150° C., and the pressure at the top of the column was about 50 kPa. Gas distilled from the top of continuous multistage distillation column 502 was condensed in condenser 503 via line 55 and continuously extracted from line 57. A liquid phase component was extracted from line 59 of continuous multistage distillation column 502 at a location lower than line 52.

The liquid phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the liquid phase component. The amount of heat required for distillative separation was supplied by circulating the liquid in the bottom of the column through line 61 and reboiler 507. The liquid temperature in the bottom of continuous multistage distillation column 505 was 150° C., and the pressure at the top of the column was about 1.5 kPa. Gas distilled from the top of continuous multistage distillation column 505 was condensed in condenser 506 via line 60 and continuously extracted into storage tank 509 via line 62. Liquid was recovered from line 62 at the rate of about 38.7 g/hr, and the liquid contained about 99.8% by weight of hexamethylene diisocyanate.

When operation was carried out continuously for 10 days by repeating steps (A-4) to (A-6) above, accumulation of adhered substances was observed on the walls of reaction vessel 904, column 905, storage tank 906, thin film distillation apparatus 501, storage tank 510 and lines connecting these components.

Comparative Example 2

Step (B-1): Production of 3-((3-methylbutyloxy) carbonylamino-methyl-3,5,5-trimethylcyclohexylcarbamic Acid (3-methylbutyl)Ester A process was carried out in the same manner as step (1-1) of Example 1 with the exception of carrying out the reaction by supplying 3394 g (16.8 mol) of bis(3-methylbutyl)carbonate of Reference Example 1, 596 g (3.5 mol) of 3-aminomethyl-3,5,5-trimethylcyclohexylamine instead of hexamethylene diamine and 6.8 g of sodium methoxide (28% methanol solution). As a result of analyzing the solution following the reaction by liquid chromatography, 3-((3-methylbutyloxy) carbonylamino-methyl-3,5,5-trimethylcyclohexylcarbamic acid (3-methylbutyl)ester was found to have been formed at a yield of 99.5%. The reaction liquid was supplied to column 205 which was packed with an acidic ion exchange resin (Amberlyst-15, spherical, Rohm and Haas Co., USA) adjusted by removing the moisture and which was warmed to 80° C. by an external jacket so as to neutralize the sodium methoxide. The solution was then transferred to storage tank 206 via line 25.

Step (B-2): Removal of Low Boiling Point Component

Alcohol was removed using an apparatus like that shown in FIG. 3.

The mixture recovered into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 280 g/hr. The amount of heat required for distillation was supplied by circulating the liquid in the bottom of the column through line 33 and reboiler 304. The liquid temperature in the bottom of continuous multistage distillation column 302 was 160° C., and the pressure at the top of the column was about 70 kPa. Gas distilled from the top of continuous multistage distillation column 302 was condensed in condenser 303 via line 32 and continuously extracted into storage tank 305 from line 34 at the rate of about 43 g/hr. Liquid was continuously extracted from the bottom of the column through line 33 into storage tank 306 at the rate of about 237 g/hr.

Carbonic acid ester was removed using an apparatus like that shown in FIG. 4.

The mixture recovered into storage tank 306 was continuously fed in a liquid state through preheater 401 to the middle stage of continuous multistage distillation column 402 packed with Dickson packing (diameter: 6 mm) and having an inner diameter of about 5 cm and column length of 2 m from line 41 at the rate of about 237 g/hr. The amount of heat required for distillation was supplied by circulating the liquid in the bottom of the column through line 43 and reboiler 404. The liquid temperature in the bottom of continuous multistage distillation column 402 was 160° C., and the pressure at the top of the column was about 2.6 kPa. Gas distilled from the top of continuous multistage distillation column 402 was condensed in condenser 403 via line 42 and continuously extracted into storage tank 405 from line 44 at the rate of about 138 g/hr. Liquid was continuously extracted from the bottom of the column through line 43 into storage tank 406 at the rate of about 98 g/hr.

As a result of analyzing the mixture extracted into storage tank 406 by liquid chromatography, the mixture was found to contain about 99.0% by weight of 3-((3-methylbutyloxy)carbonylamino-methyl-3,5,5-trimethylcyclohexylcarbamic acid (3-methylbutyl)ester.

Step (B-3): Production of Isocyanate by Thermal Decomposition of 3-((3-methylbutyloxy)carbonylamino-methyl-3,5,5-trimethylcyclohexylcarbamic Acid (3-methylbutyl)Ester A reaction was carried out using an apparatus like that shown in FIG. 5.

Thin film distillation apparatus 501 having a heat-conducting surface area of 0.1 m² was heated to 270° C. and the pressure within was set to be about 0.13 kPa. The mixture recovered into storage tank 406 in step (B-2) was heated to 170° C. and supplied to the top of thin film distillation apparatus 501 via line 50 at the rate of about 200 g/hr. In addition, dibutyl tin dilaurate was fed from line 51 at the rate of about 25.2 g/hr, and a gaseous phase component was extracted from line 52. Hardly any liquid phase component was recovered from the bottom of thin film distillation apparatus 501.

The gaseous phase component extracted from thin film distillation apparatus 501 via line 52 was continuously fed to the middle stage of continuous multistage distillation column 502 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 56 and reboiler 504. The liquid temperature in the bottom of continuous multistage distillation column 502 was 150° C., and the pressure at the top of the column was about 50 kPa. Gas distilled from the top of continuous multistage distillation column 502 was condensed in condenser 503 via line 55 and continuously extracted from line 57. A liquid phase component was extracted from line 59 of continuous multistage distillation column 502 at a location lower than line 52.

The gaseous phase component extracted from line 59 was continuously fed to the middle stage of continuous multistage distillation column 505 packed with Dickson packing (diameter: 6 mm) and having an inner diameter of 5 cm and column length of 2 m to carry out distillative separation of the gaseous phase component. The amount of heat required for distillative separation was supplied by circulating the liquid in the bottom of the column through line 61 and reboiler 507. The liquid temperature in the bottom of continuous multistage distillation column 505 was 150° C., and the pressure at the top of the column was about 1.5 kPa. Gas distilled from the top of continuous multistage distillation column 505 was condensed in condenser 506 via line 60 and continuously extracted into storage tank 509 via line 62. The extracted amount in the steady state was about 101 g/hr.

The liquid extracted from line 62 was a solution containing about 99.8% by weight of isophorone diisocyanate. The yield based on hexamethylene diamine was 91.5%.

When continuous operation was carried out for 24 hours, accumulation of an adhered substance was observed on the walls of thin film distillation apparatus 501.

Comparative Examples 3 to 5

The procedure of Example 4 was carried out continuously and various cleaning solvents were used every 30 days to carry out the cleaning procedure using the same method as Example 15. Those results are shown in Table 1.

[Table 1]

TABLE 1

Results of Carrying Out Cleaning Procedure

| | Temperature in thin film distillation apparatus | Cleaning solvent | Cleaning solvent supply rate | Cleaning time | Results |
|---|---|---|---|---|---|
| Example 20 | 200° C. | 2,6-dimethylphenol | 1000 g/hr | 2 hr | ○ |
| Example 21 | 210° C. | 2,4,6-trimethylphenol | 800 g/hr | 2 hr | ○ |

TABLE 1-continued

Results of Carrying Out Cleaning Procedure

| | Temperature in thin film distillation apparatus | Cleaning solvent | Cleaning solvent supply rate | Cleaning time | Results |
|---|---|---|---|---|---|
| Example 22 | 250° C. | 2-phenylphenol | 1000 g/hr | 3 hr | o |
| Example 23 | 280° C. | 2,4(α,α-dimethylbenzyl)phenol | 1200 g/hr | 1 hr | o |
| Example 24 | 200° C. | 4-ethoxyphenol | 1100 g/hr | 2 hr | o |
| Example 25 | 270° C. | 4-dodecylphenol | 1300 g/hr | 1 hr | o |
| Example 26 | 200° C. | Salicylic acid | 800 g/hr | 2 hr | o |
| Example 27 | 220° C. | Benzoic acid | 800 g/hr | 4 hr | o |
| Comp. Ex. 3 | 200° C. | n-dodecane | 1000 g/hr | 4 hr | x |
| Comp. Ex. 4 | 200° C. | Naphthalene | 1000 g/hr | 4 hr | x |
| Comp. Ex. 5 | 180° C. | 1-phenyl ethanol | 1000 g/hr | 4 hr | x | o: Adhered substances not observed after cleaning procedure
x: Adhered substances observed after cleaning procedure
Industrial Applicability Since the isocyanate production process according to the present invention enables isocyanate to be efficiently produced without using highly toxic phosgene, the production process of the present invention is highly useful industrially and has high commercial value.

We claim:

1. A process for producing an isocyanate by subjecting a carbamic acid ester to a thermal decomposition reaction, comprising the steps of:
    recovering a low boiling point component by distillation in a thermal decomposition reaction vessel in a form of a gaseous phase component from the thermal decomposition reaction vessel in which the thermal decomposition reaction is carried out;
    recovering a liquid phase component containing the carbamic acid ester from a bottom of the thermal decomposition reaction vessel; and
    supplying all or a portion of the liquid phase component to an upper portion of the thermal decomposition reaction vessel;
    wherein the thermal decomposition reaction is carried out in a liquid phase, and
    the step for recovering the low boiling component is carried out in the thermal decomposition reaction vessel in which the thermal decomposition reaction is carried out.

2. The process according to claim 1, wherein the carbamic acid ester is supplied to the thermal decomposition reaction vessel within a temperature range of from 50 to 180° C.

3. The process according to claim 1, wherein the carbamic acid ester is supplied to the thermal decomposition reaction vessel in a form of a liquid.

4. The process according to claim 1, wherein the carbamic acid ester is a carbamic acid ester produced by reacting a carbonic acid ester with an amine compound.

5. The process according to claim 4, wherein the reaction vessel for producing the carbamic acid ester and the thermal decomposition reaction vessel may be the same or different, and the reaction vessel for producing the carbamic acid ester and the thermal decomposition reaction vessel are at least one reaction vessel selected from the group consisting of a column-type reaction vessel and a tank-type reaction vessel.

6. The process according to claim 1, wherein the thermal decomposition reaction vessel is composed of at least one reaction vessel selected from the group consisting of an evaporator, a continuous multistage distillation column, a packed column, a thin film evaporator and a falling film evaporator.

7. The process according to claim 4, wherein a mixture, in which all or a portion of a hydroxy compound and/or all or a portion of the carbonic acid ester has been separated from a mixture containing the carbamic acid ester produced by reacting a carbonic acid ester and an amine compound, is supplied to a thermal decomposition reaction apparatus.

8. The process according to claim 7, wherein the separation is carried out by distillative separation, and the distillative separation is carried out at 180° C. or lower.

9. The process according to claim 1, wherein all or a portion of the liquid phase component recovered from the bottom of the thermal decomposition reaction vessel is supplied to the upper portion of the thermal decomposition reaction vessel within a temperature range of from 50 to 180° C.

10. The process according to claim 4, wherein the carbonic acid ester is used at a stoichiometric ratio of 1 time or more based on amino groups constituting the amine compound.

11. The process according to claim 1, further comprising cleaning a high boiling point by-product adhered to the thermal decomposition reaction vessel, with an acid.

12. The process according to claim 11, wherein the acid is an aromatic hydroxy compound.

13. The process according to claim 4, wherein the carbamic acid ester is a compound represented by the following formula (1):

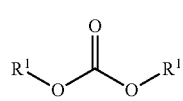

(1)

(wherein $R^1$ represents an aliphatic group having 1 to 12 carbon atoms or an aromatic group having 6 to 12 carbon atoms).

14. The process according to claim 13, wherein the carbonic acid ester contains a metal atom at from 0.001 ppm to 10%.

15. The process according to claim 14, wherein the metal atom is one type or a plurality of types of metal atoms selected from the group consisting of iron, nickel, cobalt, zinc, tin, copper and titanium atoms.

16. The process according to claim 13, wherein $R^1$ in the carbonic acid ester represents an aliphatic group having 5 to 7 carbon atoms or an aromatic group having 6 to 7 carbon atoms.

17. The process according to claim 4, wherein the amine compound is a compound represented by the following formula (2):

(wherein $R^2$ represents a group selected from the group consisting of an aliphatic group having 1 to 20 carbon atoms and an aromatic group having 6 to 20 carbon atoms, the above group containing an atom selected from carbon and oxygen atoms, and having a valence equal to n, and n represents an integer of from 2 to 10).

18. The process according to claim 17, wherein the amine compound is a diamine compound represented by formula (2) in which n is 2.

19. The process according to claim 1, wherein a low boiling point component is supplied to a distillation column in a form of a gaseous component from the low boiling point component formed by the thermal decomposition reaction and recovered in a form of a gaseous phase component, and a hydroxy compound originating from the carbamic acid ester and an isocyanate originating from the carbamic acid ester are separated in the distillation column.

20. The process according to claim 1, wherein a hydroxy compound originating from the carbamic acid ester and an isocyanate originating from the carbamic acid ester are recovered separately from a low boiling point component formed by the thermal decomposition reaction and recovered in a form of a gaseous component by a thin film evaporator.

21. The process according to claim 1, wherein the isocyanate is recovered from the liquid phase component by distillative separation.

22. The process according to claim 13, wherein $R^1$ in the carbonic acid ester in formula (1) represents an aliphatic group having 1 to 12 carbon atoms, and the carbonic acid ester is produced according to a process which comprises the following steps (1) and (2):

step (1): obtaining a reaction mixture containing a dialkyl carbonate by reacting an organic tin compound having a tin-oxygen-carbon bond and carbon dioxide; and step (2): obtaining a dialkyl carbonate and a residue liquid by separating the reaction mixture.

23. The process according to claim 13, wherein $R^1$ in the carbonic acid ester in formula (1) represents an aromatic group having 6 to 12 carbon atoms, and the carbonic acid ester is produced according to a process which comprises the following step (3) in addition to the steps (1) and (2):

step (3): obtaining a diaryl carbonate by reacting the dialkyl carbonate separated in step (2) and an aromatic hydroxy compound A followed by recovering a by-product alcohol.

24. The process according to claim 22 or 23, wherein the carbonic acid ester is a carbonic acid ester produced by a process which comprises the following steps (4) and (5) in addition to the steps (1) and (2) or the steps (1) to (3):

step (4): forming an organic tin compound having a tin-oxygen-carbon bond and water by reacting the residue liquid obtained in step (2) with an alcohol followed by removing the water from a reaction system; and step (5): reusing the organic tin compound having the tin-oxygen-carbon bond obtained in step (4) as the organic tin compound having the tin-oxygen-carbon bond of step (1).

25. The process according to claim 24, wherein the alcohol recovered in step (3) is reused as the alcohol of step (4).

26. The process according to claim 24, wherein in the case the hydroxy compound is an alcohol, it is used as the alcohol of step (4), while in the case the hydroxy compound is an aromatic hydroxy compound, it is used as the aromatic hydroxy compound A of step (3).

27. The process according to claim 7, wherein the separated carbonic acid ester is reused as a carbonic acid ester.

28. The process according to claim 1, wherein the thermal decomposition reaction of the carbamic acid ester is carried out in the absence of a solvent.

29. The process according to claim 4, wherein supply of the amine compound to the reaction vessel in which the carbonic acid ester and the amine compound are reacted is carried out in a liquid state.

30. The process according to claim 4, wherein supply of the amine compound to the reaction vessel in which the carbonic acid ester and the amine compound are reacted is carried out in a form of a mixture with alcohol, water or carbonic acid ester.

* * * * *